United States Patent [19]
Stewart et al.

[11] Patent Number: 6,051,403
[45] Date of Patent: Apr. 18, 2000

[54] NSP MOLECULES

[75] Inventors: Timothy A. Stewart, San Francisco; Yanmei Lu, Belmont, both of Calif.

[73] Assignee: Genentech, Inc., South San Francisco, Calif.

[21] Appl. No.: 09/369,028

[22] Filed: Aug. 4, 1999

Related U.S. Application Data

[62] Division of application No. 09/065,275, Apr. 23, 1998.

[51] Int. Cl.$^7$ .............................. C12P 21/06; C12N 1/20; C12N 1/14; C12N 5/08; C07H 21/04
[52] U.S. Cl. ................ 435/69.1; 435/252.3; 435/252.33; 435/254.2; 435/254.21; 435/320.1; 435/325; 435/358; 435/366; 536/23.5
[58] Field of Search ................................ 435/69.1, 252.3, 435/252.33, 254.2, 254.21, 320.1, 325, 358, 366; 536/23.5

[56] References Cited

FOREIGN PATENT DOCUMENTS

WO 98/06841   2/1998   WIPO .

OTHER PUBLICATIONS

Araki et al., "Human skeletal muscle insulin receptor substrate–1. Characterization of the cDNA, gene, and chromosomal localization" *Diabetes* 42(7):1041–10154 (Jul. 1993).
Blast Results A–1—A–3 (GenBank accession U92715, Jun. 19, 1998).
Casamassima and Rozengurt, "Tyrosine phosphorylation of p130$^{cas}$ by bombosin, lysophosphatidic acid, phorbol esters, and platelet–derived growth factor, Signaling pathways and formation of a p130$^{cas}$–Crk complex" *Journal of Biological Chemistry* 272(14):9363–9370 (Apr. 4, 1997).
Chen et al., "Osmotic shock stimulates GLUT4 translocation in 3T3L1 adipocytes by a novel tyrosine kinase pathway" *Journal of Biological Chemistry* 272(43):27401–27410 (Oct. 24, 1997).
Daniel and Reynolds, "The tyrosine kinase substrate p120$^{cas}$ binds directly to E–cadherin but not to the adenomatous polyposis coli protein or α–catonin" *Molecular & Cellular Biology* 15(9):4819–4824 (Sep. 1995).
Doerr and Jones, "The roles of integrins and extracellular matrix proteins in the insulin–like growth factor I–stimulated chemotaxis of human breast cancer cells" *Journal of Biological Chemistry* 271(5):2443–2447 (Feb. 2, 1996).
Frantz et al., "Human GRB–IRβ/GRB10. Splice varients of an insulin and growth factor receptor–binding protein with PH and SH2 domains" *Journal of Biological Chemistry* 272(5):2659–2667 (Jan. 31, 1997).
Hotamisligil et al., "Tumor necrosis factor α inhibits signaling from the insulin receptor" *Proc. Natl. Acad. Sci. USA* 91(11):4854–4858 (May 24, 1994).
Jones et al., "Ligand occupancy of the αVβ3 integrin is necessary for smooth muscle cells to migrate in response to insulin like growth factor I" *Proc. Natl. Acad. Sci. USA* 93(6):2482–2487 (Mar. 19, 1996).
Kanety et al., "Tumor necrosis factor α–induced phosphorylation of insulin receptor substrate–1 (IRS–1), Possible mechanism for suppression of insulin–stimulated tyrosine phosphorylation of 1RS–1" *Journal of Biological Chemistry* 270(40):23780–23784 (Oct. 6, 1995).
Knight et al., "Divergent insulin and platelet–derived growth factor regulation of focal adhesion kinase (pp125$^{FAK}$) tyrosine phosphorylation, and rearrangement of actin stress fibers" *Journal of Biological Chemistry* 270(17):10199–10203 (Apr. 28, 1995).
Kulik et al., "Antiapoplotic signalling by the insulin–like growth factor I receptor, phosphatidylinositol 3–kinase, and Akt" *Molecular & Cellular Biology* 17(3):1595–1606 (Mar. 1997).
Leventhal et al., "Tyrosine phosphorylation of paxillin and focal adhesion kinase during insulin–like growth factor–T––stimulated lamellipodial advance" *Journal of Biological Chemistry* 272(8):5214–5218 (Feb. 21, 1997).
Liu and Roth, "Grb–IR: a SH2–domain–containing protein that binds to the insulin receptor and inhibits its function" *Proc. Natl. Acad. Sci. USA* 92(22):10287–10291 (Oct. 24, 1995).
Luttrell et al., "Gβγ subunits mediate Src–dependent phosphorylation of the epidermal growth factor receptor. A scaffold for G protein–coupled receptor–mediated Ras activation" *Journal of Biological Chemistry* 272(7):4637–4644 (Feb. 14, 1997).
Matsumoto et al., "Growth factor regulation of integrin–mediated cell motility" *Cancer and Motastasis Reviews* 14(3):205–217 (Sep. 1995).
Mo and Reynolds, "Identification of murine p120$^{cas}$ isoforms and heterogeneous expression of p120$^{cas}$ isoforms in human tumor cell lines" *Cancer Research* 56(11):2633 2640 (Jun. 1, 1996).
Nakamoto et al., "Requirements for localization of p130$^{cas}$ to focal adhesions" *Molecular & Cellular Biology* 17(7):3884–3897 (Jul. 1997).
Hillier et al., "aa13a07.r1 Soares NhHMPu S1 Homo sapiens cDNA clone 813108 5'" (Database EMBL –EMEST11 Online Accession No. AA456485) (Jun. 7, 1997).
Hillier et al., "z186b01.s1 Stratagene colon (#937204) Homo sapiens cDNA clone 511465 3'" (Database EMBL EMEST15 Online Accession No. AA126234) (Nov. 30, 1996).
Lu et al., "Nsp1 defines a member of a family of novel adaptor proteins linking RTK and integrin signalling pathways" *Diabetes* (abstract no. 1305) 47 (Suppl. 1) :A337 (May 1998).

(List continued on next page.)

*Primary Examiner*—Ponnathapu Achutamurthy
*Assistant Examiner*—Elizabeth Slobodyansky
*Attorney, Agent, or Firm*—Craig G. Svoboda

[57] ABSTRACT

The present invention relates to nucleotide sequences, including expressed sequence tags (ESTs), oligonucleotide probes, polypeptides, antagonists and agonists vectors and host cells expressing, and immunoadhesions and antibodies to Nsp1, Nsp2 and Nsp3.

25 Claims, 24 Drawing Sheets

OTHER PUBLICATIONS

Lu et al., "NSP1 defines a novel family of adaptor proteins linking integrin and tyrosine kinase receptors to the c–Jun N–terminal kinase/stress–activated protein kinase signaling pathway" *Journal of Biological Chemistry* 274 (15):10047–10052 (Apr. 9, 1999).

Strausberg, R., "nn22g07.s1 NCI_CGAP_Co12 Homo sapiens cDNA clone IMAGE:1084668 similar to contains Alu repetitive element; contains element MER22 repetitive element" (Database EMBL –EMEST1 Online Accession No. AA577688) (Sep. 11, 1997).

Nakamura et al., "NShc: a neural–specific adapter molecule that mediates signaling from neurotrophin/Trk to Ras/MAPK pathway" *Oncogene* 13(6):1111–1121 (Sep. 19, 1996).

Nojima et al., "Integrin–mediated cell adhesion promotes tyrosine phosphorylation of p130$^{cas}$, a Src homology 3–containing molecule having multiple Src homology 2–binding motifs" *Journal of Biological Chemistry* 270(25):15398–15402 (Jun. 23, 1995).

Ojaniemi and Vuori, "Epidermal growth factor modulates tyrosine phosphorylation of p130$^{cas}$, Involvement of phosphatidylinositol 3' kinase and actin cytoskeleton" *Journal of Biological Chemistry* 272(41):25993–25998 (Oct. 10, 1997).

Parrizas et al., "Insulin–like growth factor 1 inhibits apoptosis using the phosphatidylinositol 3'–kinase and mitogen–activated protein kinase pathways" *Journal of Biological Chemistry* 272(1):154–161 (Jan. 3, 1997).

Pawson and Scott, "Signaling through scaffold, anchoring, and adaptor proteins" *Science* 278(5346):2075–2080 (Dec. 19, 1997).

Polte and Hanks, "Interaction between focal adhesion kinase and Crk–associated tyrosine kinase substrate p130$^{Cas}$" *Proc. Natl. Acad. Sci. USA* 92(23):10678–10682 (Nov. 7, 1995).

Sakai et al., "A novel signaling molecule, p130, forms stable complexes in vivo with v–Crk and v–Src in a tyrosine phosphorylation–dependent manner" *EMBO Journal* 13(16):3748–3756 (Aug. 15, 1994).

Sakai et al., "Characterization of the kinase activity essential for tyrosine phosphorylation of p130$^{Cas}$ in fibroblasts" *Oncogene* 14(12):1419–1426 (May 27, 1997).

Vemuri and McMorris, "Oligodendrocytes and their precursors require phosphatidylinositol 3–kinase signaling for survival" *Development* 122(8):2529–2537 (Aug. 1996).

FIG. 1A

```
 901 CCCAGAGCCA GAGGCCCCAT GGTGGGAGGC CGAGGAGGAT GAGGAGAAG AGAATAGATG TTTTACAAGA CCACAGGCTG AGATCTCTTT CTGCCCCCAT
     GGGTCTCGGT CTCCGGGGTA CCACCCTCCG GCTCCTCCTA CTCCTCCTTC TCTTATCTAC AAAATGTTCT GGTGTCCGAC TCTAGAGAAA GACGGGGTA
 251 P  E  P    E  A  P  W    W  E  A    E  E  D    E  E  E  E    N  R  C    F  T  R    P  Q  A  E    I  S  F    C  P  H

1001 GATGCCCCCT CCTGCCTGCT GGGCCCCCAG AATCGGCCCC TGGAACCCCA AGTCCTGCAT ACCCTCCGTG GCCTGTTCCT GGAGCACCAT CCTGGAGCA
     CTACGGGGGA GGACGGACGA CCCGGGGGTC TTAGCCGGGG ACCTTGGGGT TCAGGACGTA TGGGAGGCAC CGGACAAGGA CCTCGTGGTA GGACCCTCGT
 284 D  A  P  S    C  L  L    G  P  Q    N  R  P  L    E  P  Q    V  L  H    T  L  R  G    L  F  L    E  H  H    P  G  S  T

1101 CCGCCCTTCA CCTGCTATTG GTAGACTGCC AGGCCACAGG CCTCCCTGGA GTGACCAGAG ATCAGCGGGG CAACATGGGA GTCTCATCTG GCCTGGAGCT
     GGCGGGAAGT GGACGATAAC CATCTGACGG TCCGGTGTCC GGAGGACCCT CACTGGTCTC TAGTCGCCCC GTTGTACCCT CAGAGTAGAC CGGACCTTGA
 318 A  L  H    L  L  L    V  D  C  Q    A  T  G    L  L  G    V  T  R  D    Q  R  G    N  M  G    V  S  S  G    L  E  L

1201 GCTCACTCTT CCCCATGGAC ACCACTTGAG GTTGGAACTG CTGGAGAGGC ATCAGACACT GGGCGCTGCC CCAGGGGCGG CGGGGACCT GCTGCAGTCA
     CGAGTGAGAA GGGGTACCTG TGGTGAACTC CAACCTTGAC GACCTCTCCG TAGTCTGTGA CCCGCGACGG GGTCCCCGCC GCCCCCTGGA CGACGTCAGT
 351 L  T  L    P  H  G  H    H  L  R    L  E  L    L  E  R  H    Q  T  L    A  L  A    G  A  L  A    V  L  G    C  S  G

1301 CCGCTGGAGG AGCGCGCAGC CGCACTGAGG GGACTGGTAG AGCTGGCGCT GGGCGCGCT GGGCGCTGCG CCAGGGGCGG CCGGGGACCT GCCCGGGCTG GCTGCAGTCA
     GGCGACCTCC TCGCGCGTCG GCGTGACTCC CCTGACCATC TCGACCGCGA CCCGCGCGA CCCGCGACGC GGTCCCCGCC GGCCCCTGGA CGGGCCCGAC CGACGTCAGT
 384 P  L  E  E    R  A  A    A  L  R    G  L  V  E    L  A  L    A  L  R    P  G  A  A    G  D  L    P  G  L    A  A  V  M

1401 TGGGCGCCCT GCTCATGCCC CAGGTGTCCC GGTTTGAGCA CAGCTCCCAA GGAGCCACAC GGAGCCACAC CTGGCCTTTG AGCAGGAGCT
     ACCCGCGGGA CGAGTACGGG GTCCACAGGG CCAAACGTCGT GTCGAGGCTT GTCGAGCTT GACCTCGTGTG GACCGGAAAC TCGTCCTGA
 418 G  A  L    L  M  P    Q  V  S  R    L  E  H    T  W  R    Q  L  R  R    S  H  T    E  A  A    L  A  F  E    Q  E  L

1501 GAAGCCGCTG ATGCGGGCTC TGGATGAGGG CGCTGGACCC TGCCACCCCG ACGCTGGGGC CGTGAGGTGG CACCGTGGGT CACCGTGGGT TGGTTCGCCT ACTGGAGGGC
     CTTCGGCGAC TACGCCCGAG ACCTACTCCC GCGACCTGGG ACGGTGGGGC TGCGACCCCG GCACTCCACC GTGGCACCCA CACCGTGGT GTGCAGGGAC TGACCTCCCG
 451 K  P  L    M  R  A  L    D  E  G    A  G  P    C  D  P  G    E  V  A    L  P  H    V  A  P  M    V  R  L    L  E  G

1601 GAGGAAGTCG CGGGGCCGCT GGACGAGAGC CCTGCTCTCG TGTGAGCGGC TGTTGCGCAC ACAACGCGTG GCGGTCACA CCAGGCCCCT CGGGGTCACT CGGCCACTGT
     CTCCTTCAGC GCCCCGGCGA CCTGCTCTCG GGACGAGAGC ACACTCGCCG ACAACGCGTG TGTTGCGCAC CGCCAGTGT GGTCCGGGGA AAGGCCGTTCC
 484 E  E  V  A    G  P  L    D  E  S    C  E  R  L    L  R  T    L  H  G    A  R  H  M    V  R  D    A  P  K    F  R  K  V

1701 TGGCAGCCCA CGGGCCTGCGA GGATTCCGGC CTAACCCCGA GCTGAGGGAG CCCTGACCA CCGGCTTCGT GCGAGGCTG CTCTGGGGTA GCCGGGGCGC
     ACCGTCGGGT GCCCGGACGCT CCTAAGGCCT GATTGGGCT CGACTCCCTC GGGACTGGT GGCGAAGCA CGCTCCGACG GAGACCCCAT CGGCCCCGCG
 518 A  A  Q    R  L  R    G  F  R  P    N  P  E    L  R  E    A  L  T  T    G  F  V    R  R  L    L  W  G  S    R  G  A
```

FIG. 1B

```
1801 GGGAGCTCCG CGGCCTGAAC GCTTTGAGAA GTTCCAGCGC TCCTGTCGCA GGCCTGGAG CCTGACCGCT GAGAGCGCAG ACACCCTTCT
     CCCTCGAGGC GCGGACTTG CGAAACTCTT CAAGGTCGCG AGGACAGCGT CGGGACCTC GGACTGGCA CTCTCGCGTC TGTGGGAAGA
551      G  A  P   R  A  E  R   F  E  K  F   Q  R  V  L   G  V  R  L   E  P  D  R   Q

1901 TCACACCCGG GACCCCCAGG TTTTTGCGAA CCCCAGAAGA GTCGTCCCAG GCTCCTCGCG CCTCAGGTGG AATCCTGCCC TGTGCCTCAC
     AGTGTGGGCC CTGGGGGTCC AAAAACGCTT GGGGTCTTCT CAGCAGGGTC CGAGGAGCGC GGAGTCCACC TTAGGACGGG ACACGGAGTG

2001 AGAAGAGGTG GGGACCGCAG TCAGGGTCAC CTGGACCATG GTGAACATGT GACCTGCAGA TCTGGCATCA GAGGCCAGAG TTCAAATGTG ACTCCACCTC
     TCTTCTCCAC CCCTGGCGTC AGTCCCAGTG GACCTGGTAC CACTTGTACA CTGGACGTCT AGACCGTAGT CTCCGGTCTC AAGTTACAC TGAGGTGGAG

2101 TTAAAGCCG TGATTTCTAG CAGTTGACTT CACCTCTGTG TCGGCCTTTA ACAAAATCAT AGCCATACAG CAGCTCAGGC CTGTAATCTC AGCACTTTGG
     AATTTTCGGC ACTAAAGATC GTCAACTGAA GTGGAGACAC AGCCGGAAAT TGTTTTAGTA TCGGTATGTC GTCGAGTCCG GACATTAGAG TCGTGAAACC

2201 GAGGCCGAGG CGGAAGGAAG GCTTGAGGCC AGGAGTTCAA GACCAGCCAG GGCAACATGG CCGTTGTACC ACTCTGGAGT AGAGATGTTT TTGACTTTTT ATTTTTTGAA
     CTCCGGCTCC GCCTTCCTTC CGAACTCCGG TCCTCAAGTT CTGGTCGGTC CCGTTGTACC TGAGACCTCA TCTCTACAAA AACTGAAAA TAAAAAACTT

2301 TTAAAAAATG TAAAAAAAAA AAAAAAAGGG CGGCCGCGAC TCTAGAGTCG ACCTGCAGAA GCTTGGCCGC CATGGCCCGC GTACCGGCGG GTACCGGCGG GTACCGGCGG CTTGTTTATT GCAGCTTATA
     AATTTTTAC ATTTTTTTTT TTTTTTTCCC GCCGGCGCTG AGATCTCAGC TGGACGTCTT CGAACCGGCG GTACCGGGCG GAACAAATAA CGTCGAATAT

2401 ATGGTTACAA ATA
     TACCAATGTT TAT
```

FIG. 1C (SEQ ID NO: 4)

(SEQ ID NO: 3)

```
  1 GGCCCTGGA GTCCAGCCGC AGTGGTCACT GCTTAAATAT CACTTCTCGG GAGATATTTC CTTTTGTAAT TGCCCTCGG TCTTGTCTTA TCTTCGAAAG
    CCGGGACCT CAGGTCGGCG TCACCAGTGA CGAATTTATA GTGAAGAGCC CTCTATAAAG GAAACATTA AACGGGAGCC AGAACAGAAT AGAAGCTTTC
    ^insert starts here 101 GTTGCTGGAA TTTCTCTGTT CCTTGGAGTT TTGATTTGTT TTTTCTTTGG TGCTTGTAAA GAAACAAAGA AAAGAGTGGT AGCCAGCCCG
    CAACGACCTT AAAGAGACAA GGAACCTCAA ACCCCAAAA AACTAAACAA ACGAACATTT CTTTGTTTCT TTTCTCACCA TCGGTCGGGC
  1                                                                       M Q 201 CCTGCCTGA TCACATGCAG GACAGAAGAG CCTTGTCCCT CAAAGCCCAC CAGTCAGAGA GCTACCTGCC GATTGGCTGC CTCAGTCCTC
    GGACGGACCT AGTGTACGTC CTGTCTTCTC GGAACAGGGA GTTTCGGGTG GTCAGTCTCT CGATGGACGG CTAACCGACG TTCAGCAGAG
                 D R R A L S L K A H Q S E S Y L P I G C K L P P Q S S 301 GGGTGTGGAC ACAAGCCCCT GCCCAAACTC ACCTGTGTTC AGGACGGGAA TCCTGCCCTT CCCTGAGCCCA GCGAGCCTGC GGAGGGTCTC CTCAGACGCC
    CCCACACCTG TGTTCGGGGA CGGGTTTGAG TGGACACAAG TCCTGCCCTT AGGACGGGAA GGGACTCGGGT CGCTCGGACG CCTCCCAGAG GAGTCTGCGG
 30  G V D T S P C P N S P V F R T G S E P A L S P A V V R V S D A 401 AGGGCTGGGG AGGGCTGAGT GGGATCAGAC AGTCAACTGA CCCGCTAAGC CCCTGCAAGG TGCCGTTCCT CAAGGTTCCC TCGTCTCCCT
    TCCCGACCCC TCCCGACTC CCCTAGTCTG TCAGTTGACT GGGCGATTCG GGGACGTTCC ACGGCAAGGA GTTCCAAGGG AGCAGAGGGA
 63  R A G E A L R G S D S Q L C P K P P P K P C K V P F L K V P S S P S 501 CTGCCTGGCT CAACTCAGAG GCCAACTACT GTGAACTGAA GCCACAGGCT GCGGCAGGGG AGCAAAGCTA CCCTCATGTG CCCAGGGAAG
    GACGGACCGA GTTGAGTCTC CGGTTGATGA CACTTGACTT CGGTGTCCGA CGCCGTCCCC TCGTTTCGAT GGGAGTACAC GGGTCCCTTC
 97  A W L N S E A N Y C E L N P A F A T G C G R G A K L P S C A Q G S 601 CCACACAGAA CTGCTCACAG CCAAGCAGAA TGAGGCGCCA GGTTCCCCGA ACTCTGGCGT CAACTACTTG ATCCTTGATG ATGATGACAG GGAAAGACCT
    GGTGTGTCTT GACGAGTGTC GGTTCGTCTT GGTTCGTCTT CCAGGGGCCT CCAGGGGCT TGAGACCGCA GTTGATGAAC TAGGAACTAC TACTACTGTC CCTTTCTGA
130  H T E L L T A K Q N E A P G P R N S G V N Y L I L D D D D R E R P 701 TGGGAACCTG CGGCAGCTCA GATGAGAAG CTACCTCTTC CCGTCACCC GTTCCCGCT ACAAGGGCGA GGGCAGTGGG GTTGTGACG AGACTGTCTC CTCCTTCAGG CCCAACGAGT
    ACCCTTGGAC GCCGTCGAGT CTACTCTTTC GATGGAGAAG GGCAGTGGG CAATTCCCGCT TGTTCCCGCT ACAACACTGC TCTGACAGAG GAGGAAGTCC GGGTTGCTCA
163  W E P A A Q M E K G Q W D K G E F V T P L L E T V S S F R P N E F 801 TTGAGTCAAA GTTCCTTCCC CCTGAGAATA AGCCCCTTGA AACAGCAATG TTGCGTTAC AACTTTCTTGA CAAAAGAACT GTTCACCAAC GTTCACGCTG CAAGTGGTT TGCTGGGGT TCCAGTAGCC
    AACTCAGTTT CAAGGAAGGG GGACTCTTAT TCGGGGACTT TGTCGTTAC AACGCAATTG TTGAAACGTG AACTTTCTTGA CAAAAGAACT GTTCACCAAC GTTCACGCTG CAAGTGGTT TGCTGGGGT TCCAGTAGCC
197  E S K F L P P E N K P L E T A M L K R A K E L F T N D P K V I A
```

FIG. 2A

```
 901 CCAGCACGTA CTGAGCATGG ACTGCAGGGT TGCTAGGATA CTTGGAGTCT CTGAAGAGAT GAGGAGGAAC ATGGGGGTGA GCTCAGGCCT GGAACTCATT
     GGTCGTGCAT GACTCGTACC TGACGTCCCA ACGATCCTAT GAACCTCAGA GACTTCTCTA CTCCTCCTTG TACCCCCACT CGAGTCCGGA CCTTGAGTAA
 230  Q  H  V  L  S  M  D  C  R  V  A  R  I  L  G  V  S  E  E  M  R  R  N  M  G  V  S  G  L  E  L  I

1001 ACCTTGCCTC ACGGACACCA GCTGCGCCTG GACATAATTG AAAGACACAA CACAATGGCC ATCGGCATTG CAGTGGACAT TCTGGGATGC ACGGGCACTT
     TGGAACGGAG TGCCTGTGGT CGACGCGGAC CTGTATTAAC TTTCTGTGTT GTGTTACCGG TAGCCGTAAC GTCACCTGTA AGACCCTACG TGCCCGTGAA
 263  T  L  P  H  G  H  Q  L  R  L  D  I  I  E  R  H  N  T  M  A  I  G  I  A  V  D  I  L  G  C  T  G  T  L

1101 TGGAGGACCG AGCGGCCACT CTGAGTAAGA TCATCCAGGT GGCGGTGGAA CTGAAGGATT CCATGGGGGA CCCTCTATTCC TTTCTCAGCTC TCATGAAAGC
     ACCTCCTGGC TCGCCGGTGA GACTCATTCT AGTAGGTCCA CCGCCACCTT GACTTCCTAA GGTACCCCCT GGAGATAAGG AAGAGTCGAG AGTACTTTCG
 297  E  D  R  A  A  T  L  S  K  I  I  Q  V  A  V  E  L  K  D  S  M  G  D  L  Y  S  F  S  A  L  M  K  A

1201 CCTGAAATG CCACAGATCA CAAGGTTAGA AAAGACGTGG ACTGCTCTGC GGCACCAGTA CACCCAAACT GCCATTCTCT ATGAGAAACA GCTGAAGCCC
     GGACTTTAC GGTGTCTAGT GTTCCAATCT TTTCTGCACC TGACGAGACG CCGTGGTCAT GTGGGTTTGA CGGTAAGAGA TACTCTTTGT CGACTTCGGG
 330  L  E  M  P  Q  I  T  R  L  E  K  T  W  T  A  L  R  H  Q  Y  T  Q  T  A  I  L  Y  E  K  Q  L  K  P

1301 TTCAGCAAAC TCCTGCATGA AGGCAGAGAG TCCACACATGTG GTCCCACTGC CAGGGTGACG ACTACGGCGA ACACTGCAAT TACCTCGCGG
     AAGTCGTTTG AGGACGTACT TCCGTCTCTC AGGTGTACAC CAGGGTGTAC GTTACATAGT GGGTGACGAC GTGACGTTGA TGGAGCGCC
 363  F  S  K  L  H  E  G  R  E  S  T  C  V  P  P  N  V  S  V  P  L  L  M  P  L  V  T  L  M  E  R  Q

1401 AGGCTGTGAC TTTTGAAGGA ACCGACATGT GGGAAAAAAA CCCCTTTTTT GCTGGTCTCG TGTGAAATCA TGCTGAACCA TTTGCAACA GCGCGATTCA TGGCCGAGGC
     TCCGACACTG AAAACTTCCT TGGCTGTACA CCCTTTTTTT CGACCAGAGC ACACTTTAGT ACGACTTGGT AAACGGTTGT CGCGCTAAGT ACCGGCTCCG
 397  A  V  T  F  E  G  T  D  M  W  E  K  N  D  Q  S  C  E  I  M  L  N  H  L  A  T  A  R  F  M  A  E  A

1501 TGCAGACAGC TACCGGATGA ATGCTGAGAG GATCCTGGCA CAGACAGAGA GATATGAGAA AATTCAACCAG ATTCTGACAG CTGAATTTCA AATGCGATTG
     ACGTCTGTCG ATGGCCTACT TACGACTCTC CTAGGACCGT GTCTGTCTCT CTATACTCTT TTAAGTTGGTC TAAGACTGTC GACTTAAAGT TTACGCTAAC
 430  A  D  S  Y  R  M  N  A  E  R  I  L  A  Q  T  E  R  Y  E  K  I  Q  P  D  E  E  M  N  E  I  C  K  T  E  F  Q  M  R  L

1601 CTATGGGGCA GCAAAGGTGC ACAAGTCAAT CAGACAGAGA GTCTGTCTCT CTATACTCTT TAAAATTGAC GGGAGAGCGC ATTTAACCTT GGAGGAGGAC
     GATACCCCGT CGTTTCCACG TGTTCAGTTA GTCTGTCTCT AGATACTCTT TTAAAATTGAC CCTCCTCCTG
 463  L  W  G  S  K  G  A  Q  V  N  Q  T  E  R  V  S  L  S  L  Y  T  L  S  R  K  L  E  P  P  P  V

1701 TAAAGCAGGC AGAGCTTTGA TAACTCTCCA GAGAACCCTT TCAAGTTTC AGAATATCTT AGAATATCTT TCCAGCTTCA TCTTTGGGAA AGCTTACTGT TTTTGATAAA
     ATTTCGTCCG TCTCGAAACT ATTGAGAGGT AGAAACCTT AGAAACCCTT AGTTCAAAG TCTTATAGAA TCTTATAGAA GGTCGAAGT AGAAACCCTT TCGAATGACA AAAACTATTT
 497  K  Q  A  E  L  O
```

FIG. 2B

```
1801  GTAATAATGT GCAAATCTGA CAATATACAA GCTTTTAGTA TCCACAGGAT ATTAAACGTG TAAATTGCAC AGAGCACACT TATTTATGAA TTGTCTAAAG
      CATTATTACA CGTTTAGACT GTTATATGTT CGAAAATCAT AGGTGTCCTA TAATTTGCAC ATTTAACGTG TCTCGTGTGA ATAAATACTT AACAGATTTC

1901  TTACTACTGA TTTTAAAATG AATAATTTAT TATTAAGGTA ACTACTGCTA ATGTTGATCA GCAAATTTAA GAGAAGACCT AGCTATGTTG GCTGGTTGCT
      AATGATGACT AAAATTTTAC TTATTAAATA ATAATTCCAT TGATGACGAT TACAACTAGT CGTTTAAATT CTCTTCTGGA TCGATACAAC CGACCAACGA

2001  TTCTATTATC ATGGTATTTG ACCATTTTAG TTTTAATTCC ATGTCAGATA AGTGTAAATA GAAGAGTTTA AAAGCATGAA ACATTTCAGA AGGTATCAGT
      AAGATAATAG TACCATAAAC TGGTAAAATC AAAATTAAGG TACAGTCTAT TCACATTTAT CTTCTCAAAT TTTCGTACTT TGTAAAGTCT TCCATAGTCA

2101  TATATGATAT TCTTTAAACA AATATGAAAA ATGTAAATAC TCATGAATGA AAATACATCT TTTTGTGAAA CAGT
      ATATACTATA AGAAATTTGT TTATACTTTT TACATTTATG AGTACTTACT TTTATGTAGA AAAACACTTT GTCA
```

```
801  TCGAGAGCC  CTAGTCCCC  TGCTACAGC  ACTGTAACCC  GTGTCCATGC  GCCCCTTCTG  CCACAGCATT  GCCTGCCTCC  CCTGTCGCCC
     AGGCTCTCG  GATCGAGGG  ACGATGTCG  TGACATTGGG  CACAGGTACG  CGGGGAAGAC  GGTGTCGTAA  CGGACGGAGG  GGACAGCGGG
254   S  E  S  P  S  S  P  A  Y  S  T  V  T  R  V  H  A  A  P  A  A  P  S  A  P  P  L  P  A  S  P  V  A  R

901  GCTGTTCCAG  TGAGCCCAG  CTGTGTCCCG  GAAGTGCCCC  AAAGACCCAT  GGGGAGTCAG  ACAAGGGCCC  CCACACCAGC  CCCTTGGCAA
     CGACAAGGTC  ACTCGGGGTC  GACACAGGGC  CTTCACGGGG  TTTCTGGGTA  CCCCTCAGTC  TGTTCCCGGG  GGTGGTGGTCG  GGGAACCGTT
288   C  S  S  E  P  Q  L  C  P  G  S  A  P  K  T  H  G  E  S  D  K  G  P  H  T  S  P  S  H  T  L  G  K

1001 GGCTCCCCG  TCACCATCAC  TCAGCAGCTA  CAGTGACCCG  GCTCCAGCCT  CCCGTGCTG  GCAGCCGAGA  GTGGGCAGCG
     CCGGAGGGGC  AGTGGTAGTG  AGTCGTCGAT  GTCACTGGGC  CGAGACGCAC  GGGCACGCAC  CGTCGGCTCT  CACCCGTCGC
321   A  S  P  S  P  S  L  S  S  Y  S  D  P  D  S  G  H  Y  C  Q  L  Q  P  P  V  R  G  S  R  E  W  A  A

1101 ACTGAGACCT  CCAGCAGCA  GGCCAGGAGC  TATGGGAGA  GGCTAAAGGA  ACTGTCAGAA  AATGGGGCCC  CTGAAGGGA  ACCTTCACAG
     TGACTCTGGA  GGTCGGTCGT  CCGGTCCTCG  ATACCCCTCT  CCGATTTCCT  TGACAGTCTT  TTACCCCGGG  GACTTCCCT  TGGAAGTGTC
354   T  E  T  S  S  Q  Q  A  R  S  Y  G  E  R  L  K  E  L  S  E  N  G  A  P  E  G  D  W  G  K  T  F  T  V

1201 TCCCCATCGT  GGAAGTCACT  TCTTCCTTCA  ACCGGGCAC  CTACTGATCC  CCAGGGATAA  CCGGCCACTG  GAGGTGGGCC  TTTCTGCGCAA
     AGGGGTAGCA  CCTTCAGTGA  AGAAGGAAGT  TGGGCCGGTG  GAAGGTCAGT  GGTCCCTATT  GGCCGGTGAC  CTCCACCCGG  AAGAGCGTT
388   P  I  V  E  V  T  S  S  F  N  R  P  A  T  F  Q  S  L  L  I  P  R  D  N  R  P  L  E  V  G  L  R  K

1301 GGTCAAGGAG  CTGCTGGCAG  AAGTGGATGC  CCGGACGCTG  TCACCAAGGT  GGACTGCCTG  GTTGCTAGGA  TACCAAGGAG
     CCAGTTCCTC  GACGACCGTC  TTCACCTACG  GGCCTGCGAC  AGTGGTTCCA  CCTGACGGAC  CAACGATCCT  ATGGTTCCTC
421   V  K  E  L  L  A  E  V  D  A  R  T  L  A  R  H  V  T  K  V  D  C  L  V  A  R  I  L  G  V  T  K  E

1401 ATGCAGACCC  TAATGGGAGT  CCGCTGGGGC  ATGAACTGC  TCACCCTCCC  CCATGCCGG  TAGACCTGCT  GGAAAGGTTC  CACACCATGT
     TACGTCTGGG  ATTACCCTCA  GGCGACCCCG  TACCTTGACG  AGTGGGAGGG  GGTACGGCC  ATCTGGACGA  CCTTTCCAAG  GTGTGGTACA
454   M  Q  T  L  M  G  V  R  W  G  M  E  L  L  T  L  P  H  G  R  Q  L  R  L  D  L  L  E  R  F  H  T  M  S

1501 CCATCATGCT  GGCCGTGGAC  ATCCTGGGCT  TGCTGCACAA  GACCATTCAG  CTGGTAAGTC  ACGACGTGTT  CTGGCCCCG  AGTACGGGG
     GGTAGTACGA  CCGGCACCTG  TAGGACCCGA  ACGACGTGTT  CTGGTAAGTC  GACCATTCAG  TGCTGCACAA  GACCGGGGC  TCGATGCCC
488   I  M  L  A  V  D  I  L  G  C  T  G  S  A  E  E  R  A  A  L  L  H  K  T  I  Q  L  A  A  E  L  R  G

1601 GACTATGGGC  AACATGTTCA  GCTTCGCGGC  GGTCATGGGT  GCCCTGGACA  TGGCTCAGAT  TTCTCGGCTG  GAGCAGACAT  GGGTGACCCT
     CTGATACCCG  TTGTACAAGT  CGAAGCGCCG  CCAGTACCCA  CGGGACCTGT  ACCGAGTCTA  AAGAGCCGAC  CTCGTCTGTA  CCCACTGGGA
521   T  M  G  N  M  F  S  F  A  A  V  M  G  A  L  D  M  A  Q  I  S  R  L  E  Q  T  W  V  T  L  R  Q  R
```

```
1701 CACACAGAGG GTGCCATCCT GTACGAGAAG AAGCTCAAGC CTTTTCTCAA GAGCCTCAAC GAGGGCAAAG AAGGCCCGCC GCTGAGCAAC ACCACGTTTC
     GTGTGTCTCC CACGGTAGGA CATGCTCTTC TTCGAGTTCG GAAAAGAGTT CTCGGAGTTG CTCCCGTTTC TTCCGGGCGG CGACTCGTTG TGGTGCAAAG
554   H  T  E  G   A  I  L   Y  E  K   K  L  K  P   F  L  K   S  L  N   E  G  K  E   G  P  P   L  S  N   T  T  F  P

1801 CTCATGTGCT GCCCCTCATC ACCCTGCTGG AGTGTGACTC GGCCCCACCA GAGGGCCCTG AGCCCTGGGG CACGACGGAG CAGGCGGTGG AGGTGGTGCT
     GAGTACACGA CGGGGAGTAG TGGGACGACC TCACACTGAG CCGGGGTGGT CTCCCGGGAC TCGGGACCCC GTGCTGCCTC GTCCGCCACC TCCACCACGA
588   H  V  L   P  L  I   T  L  L  E   C  D  S   A  P  P   E  G  P  E   P  W  G   S  T  E   H  G  V  E   V  V  L

1901 GGCTCACCTG GAGGCCGCCC GCACAGTGGC ACACCACGGA GGCCTGTACC TGAAGTCAAG CTGCAGGGGT TCCAGGCCCG GCCGGAGCTC
     CCGAGTGGAC CTCCGGCGGG CGTGTCACCG TGTGGTGCCT CCGGACATGG ACTTCAGTTC GACGTCCCCA AGGTCCGGGC CGGCCTCGAG
621   A  H  L   E  A  A  R   T  V  A   H  H  G   G  L  Y  H   T  N  A   E  V  K   L  Q  G  F   Q  A  R   P  E  L

2001 CTGGAGGTGT TCAGCACGGA GTTCCAGATG CGGCTTCTGT CAAGGTCGCT CCACGTCAGT GGGGCAGTCA GGGTGCCAGC CCCGGCCAGG TGAGAAGTTC GACAAGGTCC
     GACCTCCACA AGTCGTGCCT CAAGGTCTAC GCCGAAGAGA GGTTCCAGGC GGTGCAGTCA CCCCGTCAGT CCCACGGTCG GGGCCGGCGCGAT ACTCTTCAAG CTGTTCCAGG
654   L  E  V  F   S  T  E   F  Q  M   R  L  L  W   G  S  Q   G  A  S   S  S  Q  A   R  R  Y   E  K  F   D  K  V  L

2101 TCACTGCCCT GTCCCACAAG CTGGAACCTG CTGTCCGCTC CAGCGAGCTG TGA
     AGTGACGGGA CAGGGTGTTC GACCTTGGAC GACAGGCGAG GTCGCTCGAC ACT
688   T  A  L   S  H  K   L  E  P  A   V  R  S   E  L  Q
```

FIG. 3C (SEQ ID NO: 13)

GTGGAGGGCGGGGGTGACAGCAGCCCGGAGCCGCGGAGCCTCAGCTTCCGCCTGGACCCA
GCCTCGTGGGAGCCCCGCGGGTCCTGCCCAGATGTGGAAGACTGAGGCCTGTTGAAAGTG
CAGAGCTCAGCCCTGGCACCCTCTGTTCCCAAGAGCTCCATGCAGGTGCCACAGGATGGA
GAAGACCTTGCTGGCCAACCTTGGTACCACGGCCTCCTGTCCCGCCAGAAGGCTGAAGCT
CTTCTTCAGCAAAA

FIG. 4A (SEQ ID NO: 14)

CATCGCCCAGCACGTACTGAGCATGGACTGCAGGGTTGCTAGGATACTTGGAGTCTCTNA
AGAGATGAGGAGGAACATGGGGGTGAGCTCAGGCCTGGAACTCATTACCTTGCCTCACGG
ACACCAGCTGCGCCTGGACATAATTGAAAGACACAACACAATGGCCATCGGCATTCGCGT
GGACATTCTGGGATGCACGGGCACTTTGGAGG

FIG. 4B (SEQ ID NO: 15)

GCTGGCAGAAGTGGATGCCCGGACGCTGGCCCGGCATGTCACCAAGGTGGACTGCCTGGT
TGCTAGGATACTGGGCGTTACCAAGGAGATGCAGACCCTAATGGGAGTCCGCTGGGGCAT
GGAACTGCTCACCCTCCCCCATGGCCGGCAGCTACGCCTAGACCTGCTGGAAAGGTTCCA
CACCATGTCCATCATGCTGGCCGNGGACATCCTGGGCTGCACCGGCTCTGCGGAGGAGCG
GG

FIG. 4C (SEQ ID NO: 7)
Probe for Cloning NSP1:     ACTGAGGCCTGTTGAAAGTGCAGAGCTCAG (SEQ ID NO: 8)
Enrichment Primer for NSP1:   GCTGAAGAAGAGCTTCAG

FIG. 5A

(SEQ ID NO: 9)
Probe for Cloning NSP2:

CAATGCCGATGGCCATTGTGTTGTGTCTTTCAATTATGTCCAGGCGCA (SEQ ID NO: 10)
Enrichment Primer for NSP2:ATCCCAGAATGTCCACTG

FIG. 5B

(SEQ ID NO: 11)
Probe for cloning nsp3:

GGCCAGCATGATGGACATGGTGTGGAACCTTTCCAGCAGGTCTAGGCGTA (SEQ ID NO: 12)
enrichment primer for nsp3: GGTGCAGCCCAGGATGTC

FIG. 5C

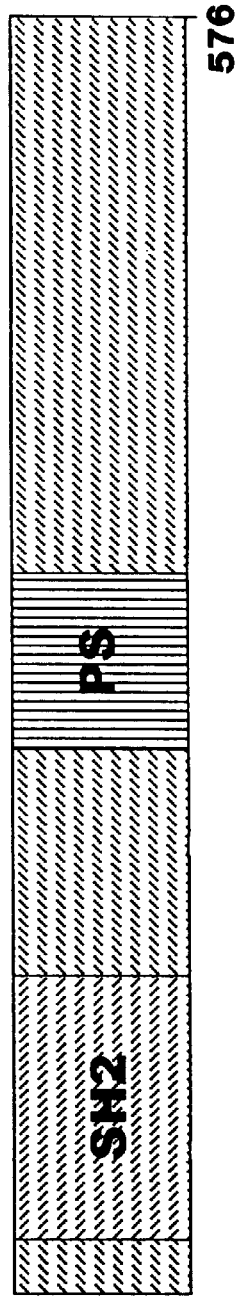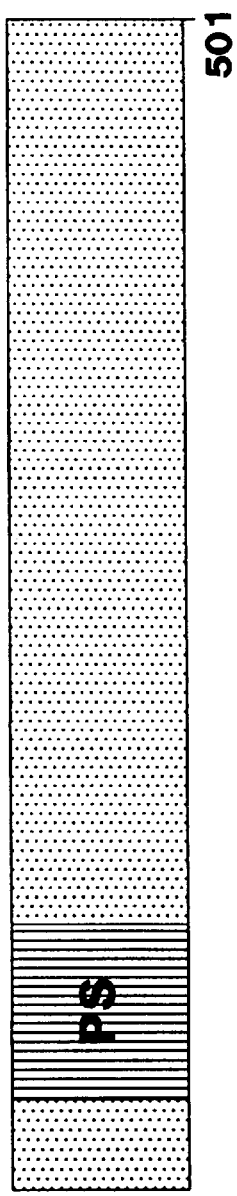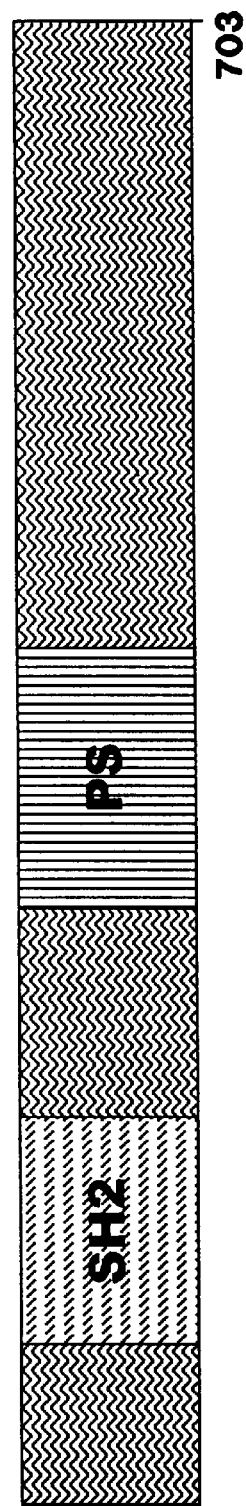
FIG. 6A

```
nsp1    1                                            MQ
nsp3    1  MTAVGRRCPALGSRGAAGEPEAGSDYVKFSKEKYILDSSPEKLHKELEEE nsp1    3  VPQDGEDLAGQPWYHGLLSRQKAEALLQQDGDFLVRASGSRGGNPVISCR
nsp3   51  LKLSSTDLRSHAWYHGRIPREVSETLVQRNGDFLIRDSLTSLGDYVLTCR nsp1   53  WRGSALHFEVFRVALRPRPGRPTALFQLEDEQFPSIPALVHSYMTGRRPL
nsp3  101  WRNQALHFKINKVVVKAGESYTHIQYLFEQESFDHVPALVRYHVGSRKAV
nsp2    1                                         MQDRRALS nsp1  103  SQATGAVVSRPVTWQGPLRRSFSEDTLMDGPARIEPLRARKWSNSQPADL
nsp3  151  SEQSGAIIYCPVNRTFPLRYLEASYGLGQGSSKPASPVSPSGPKGSHMKR
nsp2    9  LKAHQSESYLPIGCKLPPQSSGVDTSPCPNS--PVFRTGSEPALSPAVVR nsp1  153  AHMGRSREDPAGMEASTMPISALPRTSS
nsp3  201  RSVTMTDGLTADKVTRSDGCPTSTSLPRPRDSIRSCALSMDQIPDLHSPM
nsp2   57  RVSSDARAGEALRGSDSQLCPKPPPKP-----------CKVPFLKVPS nsp1  181            DPVLKAPAPLGTVADSLRASDGQLQAKAPTKPPRTPS
nsp3  251  SPISESPSSPAYSTVTRVHAAPAAPSATALPASPVARCSSEPQLCPGSAP
nsp2   94  SPS----------AWLNSEANYCELNPAFATGCGRGAKLPSCAQGSHTE nsp1  219  FELPDASE-------------------------RPPTYCEL
nsp3  301  KTHGESDKGPHTSPSHTLGKASPSPSLSSYSDPDSGHYCQLQPPVRGSRE
nsp2  133  LLTAKQNE--------------------------APGPRNSGV nsp1  235  VPRVPSVQGTSPSQSCPEPEAPWWEAEEDEEEENRCFTRPQAEISFCPHD
nsp3  351  WAATETSSQQARSYGERLKELSENGAPEGDWGKTFTVPIVEVTSSFNPAT
nsp2  150  NYLILDDDDRERPWEPAAAQMEKGQWDKG----EFVTPLLETVSSFRPNE nsp1  285  APSCLLGPQNRPLEPQVLHTLRGLFLEHHPGSTALHLLLVDCQATGLLGV
nsp3  401  FQSLLIPRDNRPLEVGLLRKVKELLAEVDARTLARHVTKVDCLVARILGV
nsp2  196  FESKFLPPENKPLETAMLKRAKELFTNNDPKVIAQHVLSMDCRVARILGV nsp1  335  TRDQRGNMGVSSGLELLTLPHGHHLRLELLERHQTLALAGALAVLGCSGP
nsp3  451  TKEMQTLMGVRWGMELLTLPHGRQLRLDLLERFHTMSIMLAVDILGCTGS
nsp2  246  SEEMRRNMGVSSGLELITLPHGHQLRLDIIERHNTMAIGIAVDILGCTGT nsp1  385  LEERAAALRGLVELALALRPGAAGDLPGLAAVMGALLMPQVSRLEHTWRQ
nsp3  501  AEERAALLHKTIQLAAELRGTMG-NMFSFAAVMGALDMAQISRLEQTWVT
nsp2  296  LEDRAATLSKIIQVAVELKDSMG-DLYSFSALMKALEMPQITRLEKTWTA nsp1  435  LRSHTEAALAFEQELKPLMRALDEGAG--PCDPGEVALPHVAPMVRLLE
nsp3  550  LRQRHTEGAILYEKKLKPFLKSLNEGKE--GPPLSNTTFPHVLPLITLLE
nsp2  345  LRHQYTQTAILYEKQLKPFSKLLHEGRESTCVPPNNVSVPLLMPLVTLME nsp1  483  GEEVAG-------PLDESCERLLRTLHGARHMVRDAPKFRKVAAQRLRGF
nsp3  598  CDSAPPEGPEPWGSTEHGVEVVLAHLEAARTVAHHGGLYHTNAEVKLQGF
nsp2  395  RQAVTFEGTDMWEKNDQSCEIMLNHLATARFMAEAADSYRMNAERILAGF nsp1  526  RPNPELREALTTGFVRRLLWGSRGAGAPRAERFEKFQRVLGVLSQRLEPD
nsp3  648  QARPELLEVFSTEFQMRLLWGSQGASSSQARRYEKFDKVLTALSHKLEPA
nsp2  445  QPDEEMNEICKTEFQMRLLWGSKGAQVNQTERYEKFNQILTALSRKLEPP nsp1  576  R
nsp3  698  VRSSEL
nsp2  495  PVKQAEL
```

FIG. 6B

SH2 domain

PS domain

MQVPQDGEDLAGQPWYHGLLSRQKAEALLQQDGDFLVRASGSRGGNPVISCRWRGSALHF
EVFRVALRPRPGRPTALFQLEDEQFPSIPALVHSYMTGRRPLSQATGAVVSRPVTWQGPL
RRSFSEDTLMDGPARIEPLRARKWSNSQPADLAHMGRSREDPAGMEASTMPISALPRTSS
DPVLLKAPAPLGTVADSLRASDGQLQAKAPTKPPRTPSFELPDASERPPTYCELVPRVPS
VQGTSPSQSCPEPEAPWWEAEEDEEEENRCFTRPQAEISFCPHDAPSCLLGPQNRPLEPQ
VLHTLRGLFLEHHPGSTALHLLLVDCQATGLLGVTRDQRGNMGVSSGLELLTLPHGHHLR
LELLERHQTLALAGALAVLGCSGPLEERAAALRGLVELALALRPGAAGDLPGLAAVMGAL
LMPQVSRLEHTWRQLRRSHTEAALAFEQELKPLMRALDEGAGPCDPGEVALPHVAPMVRL
LEGEEVAGPLDESCERLLRTLHGARHMVRDAPKFRKVAAQRLRGFRPNPELREALTTGFV
RRLLWGSRGAGAPRAERFEKFQRVLGVLSQRLEPDR

FIG. 7

```
nsp1.SH2      1 MQVPQDGEDLAGQPWYHGLLSRQKAEALLQQDGDFLVRASGSRGGNPV
HuShc.SH2     1 -------EQLRGEPWFHGKLSRREAEALLQLNGDFLVRESTTTPGQYV
HuSCK.SH2     1 -------EQLRQEPWYHGRMSRRAAERMLRADGDFLVRDSVTNPGQYV
HuFes.SH2     1 ----KPLHEQLWYHGAIPRAEVAELLVHSGDFLVRESQGKQ-EYV nsp1.SH2     51 CRWRGSALHFEVFRVALRPRPGRPTALFQLEDEQFPSIPALVHSYMTG
HuShc.SH2    44 GLQSGQPKHLLLVDPEG------VVRTKDHRFESVSHLTSYHMDN
HuSCK.SH2    44 GMHAGQPKHLLLVDPEG------VVRTKDVLFESTSHLIDHHHLQN
HuFes.SH2    43 VLWDGLPRHFIIQSLDN------LYRLEGEGFPSIPLLIDHLLST nsp1.SH2    101 PLSQATGAVSRPVTWQG--------------
HuShc.SH2    85 PIISAGSELCLQQPVERKL-------------
HuSCK.SH2    85 PIVAAESELHLRGVSREP-------------
HuFes.SH2    84 PLTKKSGVVLHRAVPKDKWVLNHEDLVLGEQIGRGN
```

FIG. 8

SEQUENCE LISTING

<160> NUMBER OF SEQ ID NOS: 19

<210> SEQ ID NO 1
<211> LENGTH: 576
<212> TYPE: PRT
<213> ORGANISM: Homo sapiens

<400> SEQUENCE: 1

```
Met Gln Val Pro Gln Asp Gly Glu Asp Leu Ala Gly Gln Pro Trp
 1               5                  10                  15

Tyr His Gly Leu Leu Ser Arg Gln Lys Ala Glu Ala Leu Leu Gln
                20                  25                  30

Gln Asp Gly Asp Phe Leu Val Arg Ala Ser Gly Ser Arg Gly Gly
                35                  40                  45

Asn Pro Val Ile Ser Cys Arg Trp Arg Gly Ser Ala Leu His Phe
                50                  55                  60

Glu Val Phe Arg Val Ala Leu Arg Pro Arg Pro Gly Arg Pro Thr
                65                  70                  75

Ala Leu Phe Gln Leu Glu Asp Glu Gln Phe Pro Ser Ile Pro Ala
                80                  85                  90

Leu Val His Ser Tyr Met Thr Gly Arg Arg Pro Leu Ser Gln Ala
                95                 100                 105
```

-continued

```
Thr Gly Ala Val Val Ser Arg Pro Val Thr Trp Gln Gly Pro Leu
            110                 115                 120

Arg Arg Ser Phe Ser Glu Asp Thr Leu Met Asp Gly Pro Ala Arg
            125                 130                 135

Ile Glu Pro Leu Arg Ala Arg Lys Trp Ser Asn Ser Gln Pro Ala
            140                 145                 150

Asp Leu Ala His Met Gly Arg Ser Arg Glu Asp Pro Ala Gly Met
            155                 160                 165

Glu Ala Ser Thr Met Pro Ile Ser Ala Leu Pro Arg Thr Ser Ser
            170                 175                 180

Asp Pro Val Leu Leu Lys Ala Pro Ala Pro Leu Gly Thr Val Ala
            185                 190                 195

Asp Ser Leu Arg Ala Ser Asp Gly Gln Leu Gln Ala Lys Ala Pro
            200                 205                 210

Thr Lys Pro Pro Arg Thr Pro Ser Phe Glu Leu Pro Asp Ala Ser
            215                 220                 225

Glu Arg Pro Pro Thr Tyr Cys Glu Leu Val Pro Arg Val Pro Ser
            230                 235                 240

Val Gln Gly Thr Ser Pro Ser Gln Ser Cys Pro Glu Pro Glu Ala
            245                 250                 255

Pro Trp Trp Glu Ala Glu Asp Glu Glu Glu Asn Arg Cys
            260                 265                 270

Phe Thr Arg Pro Gln Ala Glu Ile Ser Phe Cys Pro His Asp Ala
            275                 280                 285

Pro Ser Cys Leu Leu Gly Pro Gln Asn Arg Pro Leu Glu Pro Gln
            290                 295                 300

Val Leu His Thr Leu Arg Gly Leu Phe Leu Glu His His Pro Gly
            305                 310                 315

Ser Thr Ala Leu His Leu Leu Leu Val Asp Cys Gln Ala Thr Gly
            320                 325                 330

Leu Leu Gly Val Thr Arg Asp Gln Arg Gly Asn Met Gly Val Ser
            335                 340                 345

Ser Gly Leu Glu Leu Leu Thr Leu Pro His Gly His His Leu Arg
            350                 355                 360

Leu Glu Leu Leu Glu Arg His Gln Thr Leu Ala Leu Ala Gly Ala
            365                 370                 375

Leu Ala Val Leu Gly Cys Ser Gly Pro Leu Glu Glu Arg Ala Ala
            380                 385                 390

Ala Leu Arg Gly Leu Val Glu Leu Ala Leu Ala Leu Arg Pro Gly
            395                 400                 405

Ala Ala Gly Asp Leu Pro Gly Leu Ala Ala Val Met Gly Ala Leu
            410                 415                 420

Leu Met Pro Gln Val Ser Arg Leu Glu His Thr Trp Arg Gln Leu
            425                 430                 435

Arg Arg Ser His Thr Glu Ala Ala Leu Ala Phe Glu Gln Glu Leu
            440                 445                 450

Lys Pro Leu Met Arg Ala Leu Asp Glu Gly Ala Gly Pro Cys Asp
            455                 460                 465

Pro Gly Glu Val Ala Leu Pro His Val Ala Pro Met Val Arg Leu
            470                 475                 480

Leu Glu Gly Glu Glu Val Ala Gly Pro Leu Asp Glu Ser Cys Glu
            485                 490                 495
```

```
Arg Leu Leu Arg Thr Leu His Gly Ala Arg His Met Val Arg Asp
                500                 505                 510

Ala Pro Lys Phe Arg Lys Val Ala Ala Gln Arg Leu Arg Gly Phe
                515                 520                 525

Arg Pro Asn Pro Glu Leu Arg Glu Ala Leu Thr Thr Gly Phe Val
                530                 535                 540

Arg Arg Leu Leu Trp Gly Ser Arg Gly Ala Gly Ala Pro Arg Ala
                545                 550                 555

Glu Arg Phe Glu Lys Phe Gln Arg Val Leu Gly Val Leu Ser Gln
                560                 565                 570

Arg Leu Glu Pro Asp Arg
                575 576

<210> SEQ ID NO 2
<211> LENGTH: 2413
<212> TYPE: DNA
<213> ORGANISM: Homo sapiens

<400> SEQUENCE: 2
cgggggtgac agcagcccgg agccgcggag cctcagcttc cgcctggacc           50
cagcctcgtg ggagccccgc gggtcctgcc cagatgtgga agactgaggc          100
ctgttgaaag tgcagagctc agccctggca ccctctgttc ccaagagctc          150 c   atg cag gtg cca cag gat gga gaa gac ctt gct ggc             187
    Met Gln Val Pro Gln Asp Gly Glu Asp Leu Ala Gly
    1               5                   10 caa ccc tgg tac cac ggc ctc ctg tcc cgc cag aag gct             226
Gln Pro Trp Tyr His Gly Leu Leu Ser Arg Gln Lys Ala
            15                  20                  25 gaa gct ctt ctt cag caa gat ggc gac ttc ctg gtt cgc             265
Glu Ala Leu Leu Gln Gln Asp Gly Asp Phe Leu Val Arg
                30                  35 gcc tct ggg tcc cgt ggg ggc aac ccc gtg atc tcc tgc             304
Ala Ser Gly Ser Arg Gly Gly Asn Pro Val Ile Ser Cys
        40                  45                  50 cgc tgg cgg ggc tca gcc ctc cat ttt gag gtg ttc cgt             343
Arg Trp Arg Gly Ser Ala Leu His Phe Glu Val Phe Arg
                55                  60 gtg gcc ctg cgt ccc cgg cca ggc cga ccc aca gcc ctc             382
Val Ala Leu Arg Pro Arg Pro Gly Arg Pro Thr Ala Leu
65                  70                  75 ttt caa ctg gag gat gag caa ttc ccc agc ata ccg gct             421
Phe Gln Leu Glu Asp Glu Gln Phe Pro Ser Ile Pro Ala
            80                  85                  90 ctg gtt cac agt tat atg aca ggc agg cgc cca ctg tcc             460
Leu Val His Ser Tyr Met Thr Gly Arg Arg Pro Leu Ser
                95                  100 cag gcc aca ggg gct gtg gtc tcc agg cct gtg act tgg             499
Gln Ala Thr Gly Ala Val Val Ser Arg Pro Val Thr Trp
    105                 110                 115 cag ggg cct ctg cga cgc agc ttt agc gag gac acc ctg             538
Gln Gly Pro Leu Arg Arg Ser Phe Ser Glu Asp Thr Leu
                120                 125 atg gat ggc cca gct cgg ata gag cct ctc agg gca agg             577
Met Asp Gly Pro Ala Arg Ile Glu Pro Leu Arg Ala Arg
130                 135                 140 aag tgg agc aac agt cag cct gca gat ttg gca cat atg             616
Lys Trp Ser Asn Ser Gln Pro Ala Asp Leu Ala His Met
            145                 150                 155
```

```
ggg cgg tca aga gaa gac ccc gct ggg atg gaa gcc tcc          655
Gly Arg Ser Arg Glu Asp Pro Ala Gly Met Glu Ala Ser
            160                 165 acc atg ccc ata tct gcc ttg ccc cga acg agc agt gac          694
Thr Met Pro Ile Ser Ala Leu Pro Arg Thr Ser Ser Asp
    170                 175                 180 ccg gtg ttg ctg aag gcc cct gct ccc ctg gga act gtt          733
Pro Val Leu Leu Lys Ala Pro Ala Pro Leu Gly Thr Val
                185                 190 gcc gac agt ctc agg gcc tcc gat ggg cag ctt caa gcc          772
Ala Asp Ser Leu Arg Ala Ser Asp Gly Gln Leu Gln Ala
195             200                 205 aag gca cca acg aag ccc ccc cgg aca ccc tcc ttc gaa          811
Lys Ala Pro Thr Lys Pro Pro Arg Thr Pro Ser Phe Glu
        210                 215                 220 ctg cct gat gcc tct gaa cgt ccc ccg acg tac tgc gag          850
Leu Pro Asp Ala Ser Glu Arg Pro Pro Thr Tyr Cys Glu
                225                 230 ctg gtg ccc cga gtg ccc agt gtc cag gga aca tcc ccg          889
Leu Val Pro Arg Val Pro Ser Val Gln Gly Thr Ser Pro
    235                 240                 245 agc caa agc tgc cca gag cca gag gcc cca tgg tgg gag          928
Ser Gln Ser Cys Pro Glu Pro Glu Ala Pro Trp Trp Glu
                250                 255 gcc gag gag gat gag gag gaa gag aat aga tgt ttt aca          967
Ala Glu Glu Asp Glu Glu Glu Glu Asn Arg Cys Phe Thr
260             265                 270 aga cca cag gct gag atc tct ttc tgc ccc cat gat gcc         1006
Arg Pro Gln Ala Glu Ile Ser Phe Cys Pro His Asp Ala
        275                 280                 285 ccc tcc tgc ctg ctg ggc ccc cag aat cgg ccc ctg gaa         1045
Pro Ser Cys Leu Leu Gly Pro Gln Asn Arg Pro Leu Glu
                290                 295 ccc caa gtc ctg cat acc ctc cgt ggc ctg ttc ctg gag         1084
Pro Gln Val Leu His Thr Leu Arg Gly Leu Phe Leu Glu
    300                 305                 310 cac cat cct ggg agc acc gcc ctt cac ctg cta ttg gta         1123
His His Pro Gly Ser Thr Ala Leu His Leu Leu Leu Val
                315                 320 gac tgc cag gcc aca ggc ctc ctg gga gtg acc aga gat         1162
Asp Cys Gln Ala Thr Gly Leu Leu Gly Val Thr Arg Asp
325             330                 335 cag cgg ggc aac atg gga gtc tca tct ggc ctg gag ctg         1201
Gln Arg Gly Asn Met Gly Val Ser Ser Gly Leu Glu Leu
        340                 345                 350 ctc act ctt ccc cat gga cac cac ttg agg ttg gaa ctg         1240
Leu Thr Leu Pro His Gly His His Leu Arg Leu Glu Leu
                355                 360 ctg gag agg cat cag aca ctg gcg ctg gcc ggg gcg ctg         1279
Leu Glu Arg His Gln Thr Leu Ala Leu Ala Gly Ala Leu
    365                 370                 375 gcg gtg ctg ggc tgc tcg ggg ccg ctg gag gag cgc gca         1318
Ala Val Leu Gly Cys Ser Gly Pro Leu Glu Glu Arg Ala
                380                 385 gcc gca ctg agg gga ctg gta gag ctg gcg ctg gcg ctg         1357
Ala Ala Leu Arg Gly Leu Val Glu Leu Ala Leu Ala Leu
390             395                 400 cgg cca ggg gcg gcg ggg gac ctg ccc ggg ctg gct gca         1396
Arg Pro Gly Ala Ala Gly Asp Leu Pro Gly Leu Ala Ala
```

```
                405                 410                 415
gtc atg ggc gcc ctg ctc atg ccc cag gtg tcc cgg ttg          1435
Val Met Gly Ala Leu Leu Met Pro Gln Val Ser Arg Leu
                    420                 425 gag cac acg tgg cgc cag ctc cga agg agc cac acg gag          1474
Glu His Thr Trp Arg Gln Leu Arg Arg Ser His Thr Glu
430                 435                 440 gct gcg ctg gcc ttt gag cag gag ctg aag ccg ctg atg          1513
Ala Ala Leu Ala Phe Glu Gln Glu Leu Lys Pro Leu Met
                445                 450 cgg gct ctg gat gag ggc gct gga ccc tgc gac ccc ggc          1552
Arg Ala Leu Asp Glu Gly Ala Gly Pro Cys Asp Pro Gly
455                 460                 465 gag gtg gcg ctg ccg cac gtg gca ccc atg gtt cgc cta          1591
Glu Val Ala Leu Pro His Val Ala Pro Met Val Arg Leu
                470                 475                 480 ctg gag ggc gag gaa gtc gcg ggg ccg ctg gac gag agc          1630
Leu Glu Gly Glu Glu Val Ala Gly Pro Leu Asp Glu Ser
                    485                 490 tgt gag cgg ctg ttg cgc acc ctg cac ggg gcg cgt cac          1669
Cys Glu Arg Leu Leu Arg Thr Leu His Gly Ala Arg His
495                 500                 505 atg gtc cgg gac gca ccc aaa ttc cgc aag gtg gca gcc          1708
Met Val Arg Asp Ala Pro Lys Phe Arg Lys Val Ala Ala
                510                 515 cag cgc ctg cga gga ttc cgg cct aac ccg gag ctg agg          1747
Gln Arg Leu Arg Gly Phe Arg Pro Asn Pro Glu Leu Arg
520                 525                 530 gag gcc ctg acc acc ggc ttc gtg cgg agg ctg ctc tgg          1786
Glu Ala Leu Thr Thr Gly Phe Val Arg Arg Leu Leu Trp
                535                 540                 545 ggt agc cgg ggc gcg gga gct ccg cgc gct gaa cgc ttt          1825
Gly Ser Arg Gly Ala Gly Ala Pro Arg Ala Glu Arg Phe
                    550                 555 gag aag ttc cag cgc gtc ctc ggc gtc ctg tcg cag cgc          1864
Glu Lys Phe Gln Arg Val Leu Gly Val Leu Ser Gln Arg
                560                 565                 570 ctg gag cct gac cgc t gagagcgcag acaccttct tcacacccgg        1910
Leu Glu Pro Asp Arg
                575 576 gaccccagg tttttgcgaa ccccagaaga gaccaaagga gtcgtcccag         1960
gctcctcgcg cctcaggtgg aatcctgccc tgtgcctcac agaagaggtg        2010
gggaccgcag tcagggtcac ctggaccatg gtgaacatgt gacctgcaga        2060
tctggcatca gaggccagag ttcaaatgtg actccacctc ttaaaagccg        2110
tgatttctag cagttgactt cacctctgtg tcggcccttta acaaaatcat       2160 agccatacag cagctcaggc ctgtaatctc agcactttgg gaggccgagg        2210
cggaaggaag gcttgaggcc aggagttcaa gaccagccag gcaacatgg         2260 tgagacctca tctctacaaa aactgaaaaa taaaaaactt ttaaaaatg         2310 taaaaaaaaa aaaaaagg cggccgcgac tctagagtcg acctgcagaa          2360
gcttggccgc catggcccaa cttgtttatt gcagcttata atggttacaa        2410
ata                                                           2413

<210> SEQ ID NO 3
<211> LENGTH: 501
```

-continued

```
<212> TYPE: PRT
<213> ORGANISM: Homo sapiens

<400> SEQUENCE: 3

Met Gln Asp Arg Arg Ala Leu Ser Leu Lys Ala His Gln Ser Glu
 1               5                  10                  15

Ser Tyr Leu Pro Ile Gly Cys Lys Leu Pro Gln Ser Ser Gly
                20                  25                  30

Val Asp Thr Ser Pro Cys Pro Asn Ser Pro Val Phe Arg Thr Gly
                35                  40                  45

Ser Glu Pro Ala Leu Ser Pro Ala Val Val Arg Val Ser Ser
                50                  55                  60

Asp Ala Arg Ala Gly Glu Ala Leu Arg Gly Ser Asp Ser Gln Leu
                65                  70                  75

Cys Pro Lys Pro Pro Lys Pro Cys Lys Val Pro Phe Leu Lys
                80                  85                  90

Val Pro Ser Ser Pro Ser Ala Trp Leu Asn Ser Glu Ala Asn Tyr
                95                 100                 105

Cys Glu Leu Asn Pro Ala Phe Ala Thr Gly Cys Gly Arg Gly Ala
               110                 115                 120

Lys Leu Pro Ser Cys Ala Gln Gly Ser His Thr Glu Leu Leu Thr
               125                 130                 135

Ala Lys Gln Asn Glu Ala Pro Gly Pro Arg Asn Ser Gly Val Asn
               140                 145                 150

Tyr Leu Ile Leu Asp Asp Asp Arg Glu Arg Pro Trp Glu Pro
               155                 160                 165

Ala Ala Ala Gln Met Glu Lys Gly Gln Trp Asp Lys Gly Glu Phe
               170                 175                 180

Val Thr Pro Leu Leu Glu Thr Val Ser Ser Phe Arg Pro Asn Glu
               185                 190                 195

Phe Glu Ser Lys Phe Leu Pro Pro Glu Asn Lys Pro Leu Glu Thr
               200                 205                 210

Ala Met Leu Lys Arg Ala Lys Glu Leu Phe Thr Asn Asn Asp Pro
               215                 220                 225

Lys Val Ile Ala Gln His Val Leu Ser Met Asp Cys Arg Val Ala
               230                 235                 240

Arg Ile Leu Gly Val Ser Glu Glu Met Arg Arg Asn Met Gly Val
               245                 250                 255

Ser Ser Gly Leu Glu Leu Ile Thr Leu Pro His Gly His Gln Leu
               260                 265                 270

Arg Leu Asp Ile Ile Glu Arg His Asn Thr Met Ala Ile Gly Ile
               275                 280                 285

Ala Val Asp Ile Leu Gly Cys Thr Gly Thr Leu Glu Asp Arg Ala
               290                 295                 300

Ala Thr Leu Ser Lys Ile Ile Gln Val Ala Val Glu Leu Lys Asp
               305                 310                 315

Ser Met Gly Asp Leu Tyr Ser Phe Ser Ala Leu Met Lys Ala Leu
               320                 325                 330

Glu Met Pro Gln Ile Thr Arg Leu Glu Lys Thr Trp Thr Ala Leu
               335                 340                 345

Arg His Gln Tyr Thr Gln Thr Ala Ile Leu Tyr Glu Lys Gln Leu
               350                 355                 360

Lys Pro Phe Ser Lys Leu Leu His Glu Gly Arg Glu Ser Thr Cys
               365                 370                 375
```

-continued

```
Val Pro Pro Asn Asn Val Ser Val Pro Leu Leu Met Pro Leu Val
            380                 385                 390

Thr Leu Met Glu Arg Gln Ala Val Thr Phe Glu Gly Thr Asp Met
        395                 400                 405

Trp Glu Lys Asn Asp Gln Ser Cys Glu Ile Met Leu Asn His Leu
        410                 415                 420

Ala Thr Ala Arg Phe Met Ala Glu Ala Asp Ser Tyr Arg Met
        425                 430                 435

Asn Ala Glu Arg Ile Leu Ala Gly Phe Gln Pro Asp Glu Glu Met
        440                 445                 450

Asn Glu Ile Cys Lys Thr Glu Phe Gln Met Arg Leu Leu Trp Gly
        455                 460                 465

Ser Lys Gly Ala Gln Val Asn Gln Thr Glu Arg Tyr Glu Lys Phe
        470                 475                 480

Asn Gln Ile Leu Thr Ala Leu Ser Arg Lys Leu Glu Pro Pro Pro
        485                 490                 495

Val Lys Gln Ala Glu Leu
        500 501
```

<210> SEQ ID NO 4
<211> LENGTH: 2174
<212> TYPE: DNA
<213> ORGANISM: Homo sapiens

<400> SEQUENCE: 4

```
ggcccctgga gtccagccgc agtggtcact gcttaaatat cacttctcgg              50
gagatatttc cttttgtaat ttgccctcgg tcttgtctta tcttcgaaag             100
gttgctggaa tttctctgtt ccttggagtt tgggggtttt ttgatttgtt             150
ttttctttgg tgcttgtaaa gaaacaaaga aaagagtggt agccagcccg             200
cctgcctgga tcac atg cag gac aga aga gcc ttg tcc ctc                241
              Met Gln Asp Arg Arg Ala Leu Ser Leu
                1               5 aaa gcc cac cag tca gag agc tac ctg ccg att ggc tgc                280
Lys Ala His Gln Ser Glu Ser Tyr Leu Pro Ile Gly Cys
 10              15                  20 aag ctg cca cct cag tcc tcg ggt gtg gac aca agc ccc                319
Lys Leu Pro Pro Gln Ser Ser Gly Val Asp Thr Ser Pro
     25              30                  35 tgc cca aac tca cct gtg ttc agg acg gga agc gag cct                358
Cys Pro Asn Ser Pro Val Phe Arg Thr Gly Ser Glu Pro
             40              45 gcc ctg agc cca gca gtg gtt cgg agg gtc tcc tca gac                397
Ala Leu Ser Pro Ala Val Val Arg Arg Val Ser Ser Asp
 50              55                  60 gcc agg gct ggg gag gcg ctg agg gga tca gac agt caa                436
Ala Arg Ala Gly Glu Ala Leu Arg Gly Ser Asp Ser Gln
         65                  70 ctg tgc cct aag ccc ccg cct aag ccc tgc aag gtg ccg                475
Leu Cys Pro Lys Pro Pro Pro Lys Pro Cys Lys Val Pro
 75              80                  85 ttc ctc aag gtt ccc tcg tct ccc tct gcc tgg ctc aac                514
Phe Leu Lys Val Pro Ser Ser Pro Ser Ala Trp Leu Asn
         90              95                 100 tca gag gcc aac tac tgt gaa ctg aac cca gcg ttt gcc                553
Ser Glu Ala Asn Tyr Cys Glu Leu Asn Pro Ala Phe Ala
                105                 110
```

-continued

| | |
|---|---|
| aca ggc tgc ggc agg gga gca aag cta ccc tca tgt gcc<br>Thr Gly Cys Gly Arg Gly Ala Lys Leu Pro Ser Cys Ala<br>115                        120                  125 | 592 |
| cag gga agc cac aca gaa ctg ctc aca gcc aag cag aat<br>Gln Gly Ser His Thr Glu Leu Leu Thr Ala Lys Gln Asn<br>                130                       135 | 631 |
| gag gcg cca ggt ccc cgg aac tct ggc gtc aac tac ttg<br>Glu Ala Pro Gly Pro Arg Asn Ser Gly Val Asn Tyr Leu<br>140                       145                  150 | 670 |
| atc ctt gat gat gat gac agg gaa aga cct tgg gaa cct<br>Ile Leu Asp Asp Asp Asp Arg Glu Arg Pro Trp Glu Pro<br>               155                   160              165 | 709 |
| gcg gca gct cag atg gag aag ggg cag tgg gac aag ggc<br>Ala Ala Ala Gln Met Glu Lys Gly Gln Trp Asp Lys Gly<br>                     170                     175 | 748 |
| gag ttt gtg acg ccc ctc ctg gag act gtc tcc tcc ttc<br>Glu Phe Val Thr Pro Leu Leu Glu Thr Val Ser Ser Phe<br>180                       185                  190 | 787 |
| agg ccc aac gag ttt gag tca aag ttc ctt ccc cct gag<br>Arg Pro Asn Glu Phe Glu Ser Lys Phe Leu Pro Pro Glu<br>               195                   200 | 826 |
| aat aag ccc ctg gaa aca gca atg ttg aaa cgt gca aaa<br>Asn Lys Pro Leu Glu Thr Ala Met Leu Lys Arg Ala Lys<br>205                       210                  215 | 865 |
| gaa ctg ttc acc aac aac gac ccc aag gtc atc gcc cag<br>Glu Leu Phe Thr Asn Asn Asp Pro Lys Val Ile Ala Gln<br>               220                   225              230 | 904 |
| cac gta ctg agc atg gac tgc agg gtt gct agg ata ctt<br>His Val Leu Ser Met Asp Cys Arg Val Ala Arg Ile Leu<br>                       235                  240 | 943 |
| gga gtc tct gaa gag atg agg agg aac atg ggg gtg agc<br>Gly Val Ser Glu Glu Met Arg Arg Asn Met Gly Val Ser<br>             245                   250              255 | 982 |
| tca ggc ctg gaa ctc att acc ttg cct cac gga cac cag<br>Ser Gly Leu Glu Leu Ile Thr Leu Pro His Gly His Gln<br>                     260                  265 | 1021 |
| ctg cgc ctg gac ata att gaa aga cac aac aca atg gcc<br>Leu Arg Leu Asp Ile Ile Glu Arg His Asn Thr Met Ala<br>270                       275                  280 | 1060 |
| atc ggc att gca gtg gac att ctg gga tgc acg ggc act<br>Ile Gly Ile Ala Val Asp Ile Leu Gly Cys Thr Gly Thr<br>               285                   290              295 | 1099 |
| ttg gag gac cga gcg gcc act ctg agt aag atc atc cag<br>Leu Glu Asp Arg Ala Ala Thr Leu Ser Lys Ile Ile Gln<br>                     300                  305 | 1138 |
| gtg gcg gtg gaa ctg aag gat tcc atg ggg gac ctc tat<br>Val Ala Val Glu Leu Lys Asp Ser Met Gly Asp Leu Tyr<br>310                       315                  320 | 1177 |
| tcc ttc tca gct ctc atg aaa gcc ctg gaa atg cca cag<br>Ser Phe Ser Ala Leu Met Lys Ala Leu Glu Met Pro Gln<br>               325                   330 | 1216 |
| atc aca agg tta gaa aag acg tgg act gct ctg cgg cac<br>Ile Thr Arg Leu Glu Lys Thr Trp Thr Ala Leu Arg His<br>335                       340                  345 | 1255 |
| cag tac acc caa act gcc att ctc tat gag aaa cag ctg<br>Gln Tyr Thr Gln Thr Ala Ile Leu Tyr Glu Lys Gln Leu<br>                     350                   355              360 | 1294 |
| aag ccc ttc agc aaa ctc ctg cat gaa ggc aga gag tcc<br>Lys Pro Phe Ser Lys Leu Leu His Glu Gly Arg Glu Ser | 1333 |

```
                         365                 370
aca tgt gtt ccc cca aac aat gta tca gtc cca ctg ctg              1372
Thr Cys Val Pro Pro Asn Asn Val Ser Val Pro Leu Leu
    375                 380                 385 atg ccg ctt gtg acg tta atg gag cgc cag gct gtg act              1411
Met Pro Leu Val Thr Leu Met Glu Arg Gln Ala Val Thr
            390                 395 ttt gaa gga acc gac atg tgg gaa aaa aac gac cag agc              1450
Phe Glu Gly Thr Asp Met Trp Glu Lys Asn Asp Gln Ser
400                 405                 410 tgt gaa atc atg ctg aac cat ttg gca aca gcg cga ttc              1489
Cys Glu Ile Met Leu Asn His Leu Ala Thr Ala Arg Phe
                415                 420                 425 atg gcc gag gct gca gac agc tac cgg atg aat gct gag              1528
Met Ala Glu Ala Ala Asp Ser Tyr Arg Met Asn Ala Glu
                    430                 435 agg atc ctg gca ggt ttt caa cca gat gaa gaa atg aat              1567
Arg Ile Leu Ala Gly Phe Gln Pro Asp Glu Glu Met Asn
        440                 445                 450 gaa atc tgc aag act gaa ttt caa atg cga ttg cta tgg              1606
Glu Ile Cys Lys Thr Glu Phe Gln Met Arg Leu Leu Trp
                455                 460 ggc agc aaa ggt gca caa gtc aat cag aca gag aga tat              1645
Gly Ser Lys Gly Ala Gln Val Asn Gln Thr Glu Arg Tyr
465                 470                 475 gag aaa ttc aac cag att tta act gcc ctc tcg cgt aaa              1684
Glu Lys Phe Asn Gln Ile Leu Thr Ala Leu Ser Arg Lys
                480                 485                 490 ttg gaa cct cct cct gta aag cag gca gag ctt tga                  1720
Leu Glu Pro Pro Pro Val Lys Gln Ala Glu Leu
                        495                 500 501 taactctcca gagaaccttt agaatatctt ttcaagtttc cccagcttca           1770
tctttgggaa agcttactgt ttttgataaa gtaataatgt gcaaatctga           1820
caatatacaa gcttttagta tccacaggat attaaacgtg taaattgcac           1870
agagcacact tatttatgaa ttgtctaaag ttactactga ttttaaaatg           1920
aataatttat tattaaggta actactgcta atgttgatca gcaaatttaa           1970
gagaagacct agctatgttg gctggttgct ttctattatc atggtatttg           2020
accattttag ttttaattcc atgtcagata agtgtaaata gaaagagttta          2070 aaagcatgaa acatttcaga aggtatcagt tatatgatat tctttaaaca           2120
aatatgaaaa atgtaaatac tcatgaatga aaatacatct ttttgtgaaa           2170
cagt                                                             2174

<210> SEQ ID NO 5
<211> LENGTH: 703
<212> TYPE: PRT
<213> ORGANISM: Homo sapiens

<400> SEQUENCE: 5

Met Thr Ala Val Gly Arg Arg Cys Pro Ala Leu Gly Ser Arg Gly
1               5                   10                  15

Ala Ala Gly Glu Pro Glu Ala Gly Ser Asp Tyr Val Lys Phe Ser
                20                  25                  30

Lys Glu Lys Tyr Ile Leu Asp Ser Ser Pro Glu Lys Leu His Lys
            35                  40                  45
```

```
Glu Leu Glu Glu Glu Leu Lys Leu Ser Ser Thr Asp Leu Arg Ser
             50                  55                  60

His Ala Trp Tyr His Gly Arg Ile Pro Arg Glu Val Ser Glu Thr
             65                  70                  75

Leu Val Gln Arg Asn Gly Asp Phe Leu Ile Arg Asp Ser Leu Thr
             80                  85                  90

Ser Leu Gly Asp Tyr Val Leu Thr Cys Arg Trp Arg Asn Gln Ala
             95                 100                 105

Leu His Phe Lys Ile Asn Lys Val Val Lys Ala Gly Glu Ser
            110                 115                 120

Tyr Thr His Ile Gln Tyr Leu Phe Glu Gln Glu Ser Phe Asp His
            125                 130                 135

Val Pro Ala Leu Val Arg Tyr His Val Gly Ser Arg Lys Ala Val
            140                 145                 150

Ser Glu Gln Ser Gly Ala Ile Ile Tyr Cys Pro Val Asn Arg Thr
            155                 160                 165

Phe Pro Leu Arg Tyr Leu Glu Ala Ser Tyr Gly Leu Gly Gln Gly
            170                 175                 180

Ser Ser Lys Pro Ala Ser Pro Val Ser Pro Ser Gly Pro Lys Gly
            185                 190                 195

Ser His Met Lys Arg Ser Val Thr Met Thr Asp Gly Leu Thr
            200                 205                 210

Ala Asp Lys Val Thr Arg Ser Asp Gly Cys Pro Thr Ser Thr Ser
            215                 220                 225

Leu Pro Arg Pro Arg Asp Ser Ile Arg Ser Cys Ala Leu Ser Met
            230                 235                 240

Asp Gln Ile Pro Asp Leu His Ser Pro Met Ser Pro Ile Ser Glu
            245                 250                 255

Ser Pro Ser Ser Pro Ala Tyr Ser Thr Val Thr Arg Val His Ala
            260                 265                 270

Ala Pro Ala Ala Pro Ser Ala Thr Ala Leu Pro Ala Ser Pro Val
            275                 280                 285

Ala Arg Cys Ser Ser Glu Pro Gln Leu Cys Pro Gly Ser Ala Pro
            290                 295                 300

Lys Thr His Gly Glu Ser Asp Lys Gly Pro His Thr Ser Pro Ser
            305                 310                 315

His Thr Leu Gly Lys Ala Ser Pro Ser Pro Ser Leu Ser Ser Tyr
            320                 325                 330

Ser Asp Pro Asp Ser Gly His Tyr Cys Gln Leu Gln Pro Pro Val
            335                 340                 345

Arg Gly Ser Arg Glu Trp Ala Ala Thr Glu Thr Ser Ser Gln Gln
            350                 355                 360

Ala Arg Ser Tyr Gly Glu Arg Leu Lys Glu Leu Ser Glu Asn Gly
            365                 370                 375

Ala Pro Glu Gly Asp Trp Gly Lys Thr Phe Thr Val Pro Ile Val
            380                 385                 390

Glu Val Thr Ser Ser Phe Asn Pro Ala Thr Phe Gln Ser Leu Leu
            395                 400                 405

Ile Pro Arg Asp Asn Arg Pro Leu Glu Val Gly Leu Leu Arg Lys
            410                 415                 420

Val Lys Glu Leu Leu Ala Glu Val Asp Ala Arg Thr Leu Ala Arg
            425                 430                 435

His Val Thr Lys Val Asp Cys Leu Val Ala Arg Ile Leu Gly Val
```

```
                    440                 445                 450
Thr Lys Glu Met Gln Thr Leu Met Gly Val Arg Trp Gly Met Glu
                    455                 460                 465

Leu Leu Thr Leu Pro His Gly Arg Gln Leu Arg Leu Asp Leu Leu
                    470                 475                 480

Glu Arg Phe His Thr Met Ser Ile Met Leu Ala Val Asp Ile Leu
                    485                 490                 495

Gly Cys Thr Gly Ser Ala Glu Arg Ala Ala Leu Leu His Lys
                    500                 505                 510

Thr Ile Gln Leu Ala Ala Glu Leu Arg Gly Thr Met Gly Asn Met
                    515                 520                 525

Phe Ser Phe Ala Ala Val Met Gly Ala Leu Asp Met Ala Gln Ile
                    530                 535                 540

Ser Arg Leu Glu Gln Thr Trp Val Thr Leu Arg Gln Arg His Thr
                    545                 550                 555

Glu Gly Ala Ile Leu Tyr Glu Lys Lys Leu Lys Pro Phe Leu Lys
                    560                 565                 570

Ser Leu Asn Glu Gly Lys Glu Gly Pro Pro Leu Ser Asn Thr Thr
                    575                 580                 585

Phe Pro His Val Leu Pro Leu Ile Thr Leu Leu Glu Cys Asp Ser
                    590                 595                 600

Ala Pro Pro Glu Gly Pro Glu Pro Trp Gly Ser Thr Glu His Gly
                    605                 610                 615

Val Glu Val Val Leu Ala His Leu Glu Ala Ala Arg Thr Val Ala
                    620                 625                 630

His His Gly Gly Leu Tyr His Thr Asn Ala Glu Val Lys Leu Gln
                    635                 640                 645

Gly Phe Gln Ala Arg Pro Glu Leu Leu Glu Val Phe Ser Thr Glu
                    650                 655                 660

Phe Gln Met Arg Leu Leu Trp Gly Ser Gln Gly Ala Ser Ser Ser
                    665                 670                 675

Gln Ala Arg Arg Tyr Glu Lys Phe Asp Lys Val Leu Thr Ala Leu
                    680                 685                 690

Ser His Lys Leu Glu Pro Ala Val Arg Ser Ser Glu Leu
                    695                 700             703

<210> SEQ ID NO 6
<211> LENGTH: 2153
<212> TYPE: DNA
<213> ORGANISM: Homo sapiens

<400> SEQUENCE: 6
taggaggtcc ccgggttgcc ggcggcgaca gcgggggaag c   atg                    44
                                              Met
                                               1 act gct gtg ggc cga agg tgc ccc gcg ctg ggg tcc cga                    83
Thr Ala Val Gly Arg Arg Cys Pro Ala Leu Gly Ser Arg
          5                  10 ggg gct gct gga gag cca gag gct ggc agc gac tat gtg                   122
Gly Ala Ala Gly Glu Pro Glu Ala Gly Ser Asp Tyr Val
 15                  20                  25 aag ttc tcc aag gag aag tac atc ctg gac tca tcg cca                   161
Lys Phe Ser Lys Glu Lys Tyr Ile Leu Asp Ser Ser Pro
             30                  35                  40 gag aaa ctc cac aag gaa ttg gag gag gag ctc aaa ctc                   200
Glu Lys Leu His Lys Glu Leu Glu Glu Glu Leu Lys Leu
```

```
                      45                  50
agc agc acg gat ctc cgc agc cat gcc tgg tac cat ggc              239
Ser Ser Thr Asp Leu Arg Ser His Ala Trp Tyr His Gly
     55              60                  65 cgc atc ccc cga gag gtc tcg gag acc ttg gta caa cgc              278
Arg Ile Pro Arg Glu Val Ser Glu Thr Leu Val Gln Arg
             70              75 aac ggc gac ttc ctc atc cgg gac tcg ctc acc agc ctg              317
Asn Gly Asp Phe Leu Ile Arg Asp Ser Leu Thr Ser Leu
 80              85                  90 ggc gac tat gtg ctc acg tgc cgc tgg cgc aac cag gcc              356
Gly Asp Tyr Val Leu Thr Cys Arg Trp Arg Asn Gln Ala
             95              100                 105 ttg cac ttc aag atc aac aag gtg gtg gtg aag gca ggc              395
Leu His Phe Lys Ile Asn Lys Val Val Val Lys Ala Gly
                 110             115 gag agc tac aca cac atc cag tac ctg ttt gag cag gag              434
Glu Ser Tyr Thr His Ile Gln Tyr Leu Phe Glu Gln Glu
    120             125             130 agc ttt gac cac gtg ccc gcc ctc gtg cgc tat cat gtg              473
Ser Phe Asp His Val Pro Ala Leu Val Arg Tyr His Val
            135             140 ggc agc cgc aag gct gtg tca gag cag agt ggt gcc atc              512
Gly Ser Arg Lys Ala Val Ser Glu Gln Ser Gly Ala Ile
145             150             155 atc tac tgc ccg gtg aac cgc acc ttc cca ctg cgc tac              551
Ile Tyr Cys Pro Val Asn Arg Thr Phe Pro Leu Arg Tyr
            160             165             170 ctc gag gcc agc tat ggc ctg gga cag ggg agt agc aag              590
Leu Glu Ala Ser Tyr Gly Leu Gly Gln Gly Ser Ser Lys
                175             180 cct gct agc ccc gtc agc ccc tca ggc ccc aag ggc agc              629
Pro Ala Ser Pro Val Ser Pro Ser Gly Pro Lys Gly Ser
    185             190             195 cac atg aag cgg cgc agc gtc acc atg acc gat ggg ctc              668
His Met Lys Arg Arg Ser Val Thr Met Thr Asp Gly Leu
            200             205 act gct gac aag gtc acc cgc agc gat ggc tgc ccc acc              707
Thr Ala Asp Lys Val Thr Arg Ser Asp Gly Cys Pro Thr
210             215             220 agt acg tcg ctg ccc cgc cct cgg gac tcc atc cgc agc              746
Ser Thr Ser Leu Pro Arg Pro Arg Asp Ser Ile Arg Ser
        225             230             235 tgt gcc ctc agc atg gac cag atc cca gac ctg cac tca              785
Cys Ala Leu Ser Met Asp Gln Ile Pro Asp Leu His Ser
            240             245 ccc atg tcg ccc atc tcc gag agc cct agc tcc cct gcc              824
Pro Met Ser Pro Ile Ser Glu Ser Pro Ser Ser Pro Ala
    250             255             260 tac agc act gta acc cgt gtc cat gcc gcc cct gca gcc              863
Tyr Ser Thr Val Thr Arg Val His Ala Ala Pro Ala Ala
            265             270 cct tct gcc aca gca ttg cct gcc tcc cct gtc gcc cgc              902
Pro Ser Ala Thr Ala Leu Pro Ala Ser Pro Val Ala Arg
275             280             285 tgt tcc agt gag ccc cag ctg tgt ccc gga agt gcc cca              941
Cys Ser Ser Glu Pro Gln Leu Cys Pro Gly Ser Ala Pro
        290             295             300 aag acc cat ggg gag tca gac aag ggc ccc cac acc agc              980
Lys Thr His Gly Glu Ser Asp Lys Gly Pro His Thr Ser
```

```
                Lys Thr His Gly Glu Ser Asp Lys Gly Pro His Thr Ser
                                305                 310 ccc tcc cac acc ctt ggc aag gcc tcc ccg tca cca tca                   1019
Pro Ser His Thr Leu Gly Lys Ala Ser Pro Ser Pro Ser
315                 320                 325 ctc agc agc tac agt gac ccg gac tct ggc cac tac tgc                   1058
Leu Ser Ser Tyr Ser Asp Pro Asp Ser Gly His Tyr Cys
                330                 335 cag ctc cag cct ccc gtg cgt ggc agc cga gag tgg gca                   1097
Gln Leu Gln Pro Pro Val Arg Gly Ser Arg Glu Trp Ala
340                 345                 350 gcg act gag acc tcc agc cag cag gcc agg agc tat ggg                   1136
Ala Thr Glu Thr Ser Ser Gln Gln Ala Arg Ser Tyr Gly
                355                 360                 365 gag agg cta aag gaa ctg tca gaa aat ggg gcc cct gaa                   1175
Glu Arg Leu Lys Glu Leu Ser Glu Asn Gly Ala Pro Glu
                    370                 375 ggg gac tgg ggc aag acc ttc aca gtc ccc atc gtg gaa                   1214
Gly Asp Trp Gly Lys Thr Phe Thr Val Pro Ile Val Glu
380                 385                 390 gtc act tct tcc ttc aac ccg gcc acc ttc cag tca cta                   1253
Val Thr Ser Ser Phe Asn Pro Ala Thr Phe Gln Ser Leu
                395                 400 ctg atc ccc agg gat aac cgg cca ctg gag gtg ggc ctt                   1292
Leu Ile Pro Arg Asp Asn Arg Pro Leu Glu Val Gly Leu
405                 410                 415 ctg cgc aag gtc aag gag ctg ctg gca gaa gtg gat gcc                   1331
Leu Arg Lys Val Lys Glu Leu Leu Ala Glu Val Asp Ala
                420                 425                 430 cgg acg ctg gcc cgg cat gtc acc aag gtg gac tgc ctg                   1370
Arg Thr Leu Ala Arg His Val Thr Lys Val Asp Cys Leu
                    435                 440 gtt gct agg ata ctg ggc gtt acc aag gag atg cag acc                   1409
Val Ala Arg Ile Leu Gly Val Thr Lys Glu Met Gln Thr
445                 450                 455 cta atg gga gtc cgc tgg ggc atg gaa ctg ctc acc ctc                   1448
Leu Met Gly Val Arg Trp Gly Met Glu Leu Leu Thr Leu
                460                 465 ccc cat ggc cgg cag cta cgc cta gac ctg ctg gaa agg                   1487
Pro His Gly Arg Gln Leu Arg Leu Asp Leu Leu Glu Arg
470                 475                 480 ttc cac acc atg tcc atc atg ctg gcc gtg gac atc ctg                   1526
Phe His Thr Met Ser Ile Met Leu Ala Val Asp Ile Leu
                485                 490                 495 ggc tgc acc ggc tct gcg gag gag cgg gca gcg ctg ctg                   1565
Gly Cys Thr Gly Ser Ala Glu Glu Arg Ala Ala Leu Leu
                    500                 505 cac aag acc att cag ctg gcg gcc gag cta cgg ggg act                   1604
His Lys Thr Ile Gln Leu Ala Ala Glu Leu Arg Gly Thr
                510                 515                 520 atg ggc aac atg ttc agc ttc gcg gcg gtc atg ggt gcc                   1643
Met Gly Asn Met Phe Ser Phe Ala Ala Val Met Gly Ala
                    525                 530 ctg gac atg gct cag att tct cgg ctg gag cag aca tgg                   1682
Leu Asp Met Ala Gln Ile Ser Arg Leu Glu Gln Thr Trp
535                 540                 545 gtg acc ctg cgg cag cga cac aca gag ggt gcc atc ctg                   1721
Val Thr Leu Arg Gln Arg His Thr Glu Gly Ala Ile Leu
                550                 555                 560
```

-continued

| | | |
|---|---|---|
| tac gag aag aag ctc aag cct ttt ctc aag agc ctc aac<br>Tyr Glu Lys Lys Leu Lys Pro Phe Leu Lys Ser Leu Asn<br>565                           570 | | 1760 |
| gag ggc aaa gaa ggc ccg ccg ctg agc aac acc acg ttt<br>Glu Gly Lys Glu Gly Pro Pro Leu Ser Asn Thr Thr Phe<br>575                    580                  585 | | 1799 |
| cct cat gtg ctg ccc ctc atc acc ctg ctg gag tgt gac<br>Pro His Val Leu Pro Leu Ile Thr Leu Leu Glu Cys Asp<br>590                           595 | | 1838 |
| tcg gcc cca cca gag ggc cct gag ccc tgg ggc agc acg<br>Ser Ala Pro Pro Glu Gly Pro Glu Pro Trp Gly Ser Thr<br>600                    605                  610 | | 1877 |
| gag cac ggc gtg gag gtg gtg ctg gct cac ctg gag gcc<br>Glu His Gly Val Glu Val Val Leu Ala His Leu Glu Ala<br>615                      620                  625 | | 1916 |
| gcc cgc aca gtg gca cac cac gga ggc ctg tac cac acc<br>Ala Arg Thr Val Ala His His Gly Gly Leu Tyr His Thr<br>                       630                  635 | | 1955 |
| aat gct gaa gtc aag ctg cag ggg ttc cag gcc cgg ccg<br>Asn Ala Glu Val Lys Leu Gln Gly Phe Gln Ala Arg Pro<br>640                         645                  650 | | 1994 |
| gag ctc ctg gag gtg ttc agc acg gag ttc cag atg cgc<br>Glu Leu Leu Glu Val Phe Ser Thr Glu Phe Gln Met Arg<br>655                        660 | | 2033 |
| ctt ctc tgg ggc agt cag ggt gcc agc agc agc cag gcc<br>Leu Leu Trp Gly Ser Gln Gly Ala Ser Ser Ser Gln Ala<br>665                    670                  675 | | 2072 |
| cgg cgc tat gag aag ttc gac aag gtc ctc act gcc ctg<br>Arg Arg Tyr Glu Lys Phe Asp Lys Val Leu Thr Ala Leu<br>                       680                  685                  690 | | 2111 |
| tcc cac aag ctg gaa cct gct gtc cgc tcc agc gag ctg<br>Ser His Lys Leu Glu Pro Ala Val Arg Ser Ser Glu Leu<br>                       695                           700                  703 | | 2150 |
| tga | | 2153 |

<210> SEQ ID NO 7
<211> LENGTH: 30
<212> TYPE: DNA
<213> ORGANISM: artificial
<220> FEATURE:
<221> NAME/KEY: artificial sequence
<222> LOCATION: 1-30
<223> OTHER INFORMATION: artificial sequence

<400> SEQUENCE: 7
actgaggcct gttgaaagtg cagagctcag                                              30

<210> SEQ ID NO 8
<211> LENGTH: 18
<212> TYPE: DNA
<213> ORGANISM: artifical
<220> FEATURE:
<221> NAME/KEY: artificial sequence
<222> LOCATION: 1-18
<223> OTHER INFORMATION: artificial sequence

<400> SEQUENCE: 8 ctgaagaag agcttcag                                                            18

<210> SEQ ID NO 9
<211> LENGTH: 48
<212> TYPE: DNA
<213> ORGANISM: artificial

```
<220> FEATURE:
<221> NAME/KEY: artificial sequence
<222> LOCATION: 1-48
<223> OTHER INFORMATION: artificial sequence

<400> SEQUENCE: 9
caatgccgat ggccattgtg ttgtgtcttt caattatgtc caggcgca        48

<210> SEQ ID NO 10
<211> LENGTH: 18
<212> TYPE: DNA
<213> ORGANISM: artificial
<220> FEATURE:
<221> NAME/KEY: artificial sequence
<222> LOCATION: 1-18
<223> OTHER INFORMATION: artificial sequence

<400> SEQUENCE: 10
atcccagaat gtccactg        18

<210> SEQ ID NO 11
<211> LENGTH: 50
<212> TYPE: DNA
<213> ORGANISM: artificial
<220> FEATURE:
<221> NAME/KEY: artificial sequence
<222> LOCATION: 1-50
<223> OTHER INFORMATION: artificial sequence

<400> SEQUENCE: 11
ggccagcatg atggacatgg tgtggaacct ttccagcagg tctaggcgta        50

<210> SEQ ID NO 12
<211> LENGTH: 18
<212> TYPE: DNA
<213> ORGANISM: artificial
<220> FEATURE:
<221> NAME/KEY: artificial sequence
<222> LOCATION: 1-18
<223> OTHER INFORMATION: artificial sequence

<400> SEQUENCE: 12
ggtgcagccc aggatgtc        18

<210> SEQ ID NO 13
<211> LENGTH: 254
<212> TYPE: DNA
<213> ORGANISM: unknown
<220> FEATURE:
<221> NAME/KEY: unknown source
<222> LOCATION: 1-254
<223> OTHER INFORMATION:

<400> SEQUENCE: 13
gtggagggcg ggggtgacag cagcccggag ccgcggagcc tcagcttccg        50
cctggaccca gcctcgtggg agcccgcgg gtcctgccca gatgtggaag        100
actgaggcct gttgaaagtg cagagctcag ccctggcacc ctctgttccc        150
aagagctcca tgcaggtgcc acaggatgga gaagaccttg ctggccaacc        200
ttggtaccac ggcctcctgt cccgccagaa ggctgaagct cttcttcagc        250
aaaa        254

<210> SEQ ID NO 14
<211> LENGTH: 212
<212> TYPE: DNA
```

```
<213> ORGANISM: unknown
<220> FEATURE:
<221> NAME/KEY: unknown N
<222> LOCATION: 59
<223> OTHER INFORMATION:
<220> FEATURE:
<221> NAME/KEY: unknown source
<222> LOCATION: 1-212
<223> OTHER INFORMATION:

<400> SEQUENCE: 14
catcgcccag cacgtactga gcatggactg cagggttgct aggatacttg         50
gagtctctna agagatgagg aggaacatgg gggtgagctc aggcctggaa        100
ctcattacct tgcctcacgg acaccagctg cgcctggaca taattgaaag        150
acacaacaca atggccatcg gcattgcagt ggacattctg ggatgcacgg        200
gcactttgga gg                                                 212

<210> SEQ ID NO 15
<211> LENGTH: 242
<212> TYPE: DNA
<213> ORGANISM: unknown source
<220> FEATURE:
<221> NAME/KEY: unknown N
<222> LOCATION: 204
<223> OTHER INFORMATION:
<220> FEATURE:
<221> NAME/KEY: unknown source
<222> LOCATION: 1-242
<223> OTHER INFORMATION:

<400> SEQUENCE: 15
gctggcagaa gtggatgccc ggacgctggc ccggcatgtc accaaggtgg         50
actgcctggt tgctaggata ctgggcgtta ccaaggagat gcagacccta        100
atgggagtcc gctggggcat ggaactgctc accctccccc atggccggca        150
gctacgccta gacctgctgg aaaggttcca caccatgtcc atcatgctgg        200
ccgnggacat cctgggctgc accggctctg cggaggagcg gg               242

<210> SEQ ID NO 16
<211> LENGTH: 99
<212> TYPE: PRT
<213> ORGANISM: Homo sapiens

<400> SEQUENCE: 16

Glu Gln Leu Arg Gly Glu Pro Trp Phe His Gly Lys Leu Ser Arg
  1               5                  10                  15

Arg Glu Ala Glu Ala Leu Leu Gln Leu Asn Gly Asp Phe Leu Val
                 20                  25                  30

Arg Glu Ser Thr Thr Thr Pro Gly Gln Tyr Val Gly Leu Gln Ser
                 35                  40                  45

Gly Gln Pro Lys His Leu Leu Leu Val Asp Pro Glu Gly Val Val
                 50                  55                  60

Arg Thr Lys Asp His Arg Phe Glu Ser Val Ser His Leu Ile Ser
                 65                  70                  75

Tyr His Met Asp Asn Pro Ile Ile Ser Ala Gly Ser Glu Leu Cys
                 80                  85                  90

Leu Gln Gln Pro Val Glu Arg Lys Leu
                 95              99

<210> SEQ ID NO 17
```

```
<211> LENGTH: 99
<212> TYPE: PRT
<213> ORGANISM: Homo sapiens

<400> SEQUENCE: 17

Glu Gln Leu Arg Gln Glu Pro Trp Tyr His Gly Arg Met Ser Arg
 1               5                  10                  15

Arg Ala Ala Glu Arg Met Leu Arg Ala Asp Gly Asp Phe Leu Val
                20                  25                  30

Arg Asp Ser Val Thr Asn Pro Gly Gln Tyr Val Gly Met His Ala
                35                  40                  45

Gly Gln Pro Lys His Leu Leu Leu Val Asp Pro Glu Gly Val Val
                50                  55                  60

Arg Thr Lys Asp Val Leu Phe Glu Ser Ile Ser His Leu Ile Asp
                65                  70                  75

His His Leu Gln Asn Pro Ile Val Ala Ala Glu Ser Glu Leu His
                80                  85                  90

Leu Arg Gly Val Val Ser Arg Glu Pro
                95                  99

<210> SEQ ID NO 18
<211> LENGTH: 115
<212> TYPE: PRT
<213> ORGANISM: Homo sapiens

<400> SEQUENCE: 18

Lys Pro Leu His Glu Gln Leu Trp Tyr His Gly Ala Ile Pro Arg
 1               5                  10                  15

Ala Glu Val Ala Glu Leu Leu Val His Ser Gly Asp Phe Leu Val
                20                  25                  30

Arg Glu Ser Gln Gly Lys Gln Glu Tyr Val Val Leu Trp Asp Gly
                35                  40                  45

Leu Pro Arg His Phe Ile Ile Gln Ser Leu Asp Asn Leu Tyr Arg
                50                  55                  60

Leu Glu Gly Glu Gly Phe Pro Ser Ile Pro Leu Leu Ile Asp His
                65                  70                  75

Leu Leu Ser Thr Pro Leu Thr Lys Lys Ser Gly Val Val Leu His
                80                  85                  90

Arg Ala Val Pro Lys Asp Lys Trp Val Leu Asn His Glu Asp Leu
                95                 100                 105

Val Leu Gly Glu Gln Ile Gly Arg Gly Asn
                110                 115

<210> SEQ ID NO 19
<211> LENGTH: 8
<212> TYPE: PRT
<213> ORGANISM: Homo sapiens

<400> SEQUENCE: 19

Asp Tyr Lys Asp Asp Asp Asp Lys
 1               5               8
```

NSP MOLECULES

This is a divisional of application Ser. No. 09/065,275 filed on Apr. 23, 1998, which application is incorporated herein by reference and to which application priority is claimed under 35 USC §120.

FIELD OF THE INVENTION

The present invention relates generally to the identification and isolation of novel DNA and to the recombinant production of novel polypeptides which are characterized by the presence of novel SH2-containing proteins (Nsp's).

BACKGROUND OF THE INVENTION

Interactions between ligands and the cognate cell surface receptors are critical for a variety of biological processes including maintenance of cellular and organism homeostasis, development, and tumorigenesis. Many of these ligands can activate multiple independent pathways and the strength of the activation of different pathways can be modulated by the presence or absence of signals generated by other receptors, Hotamisligil, et al., *Proc. Nat. Acad. Sci. USA* 91: 4854–58 (1994); Kanety et al., *J. Biol. Chem.* 270: 23780–84 (1995); Luttrell et al, *J. Biol. Chem.* 272: 4637–44 (1997). Adaptor molecules may be critical in integrating multiple signaling cascades and in determining the cell type specific response to extracellular stimuli. These adaptor proteins have no apparent catalytic activity. Rather, they contain one or more domains that mediate protein-protein or protein-lipid interactions. The most common conserved interaction domains in these adaptor molecules are Src homology (SH2), SH3, phosphotyrosine binding (PTB) and pleckstrin homology domains. [Reviewed in Pawson and Scott, *Science* 278: 2075–80 (1997)].

Signals generated by growth factors such as epidermal growth factor (EGF) or insulin growth factor-1 (IGF-1) through receptor tyrosine kinases (RTK) or by extracellular matrix components acting through the integrin receptors can induce cytoskeletal changes, Leventhal, el al.,*J. Biol. Chem.* 272: 5214–18 (1997); Ojaniemi & Vuori, *J Biol. Chem.* 272: 25993–25998 (1996). There are also indications that RTKs can modulate integrin signals and vice versa, Doerr & Jones, *J. Biol. Chem.* 271: 2443–47 (1996); Jones et al., *Proc. Natl. Acad Sci. USA* 93: 2482–87 (1996); Knight et al., *J. Biol. Chem.* 270: 10199–203 (1995); Matsumoto et al., *Cancer Metas. Rev.* 14: 205–17 (1995). However the details of how RTKs signal to the cytoskeletal components have not been fully resolved. Further, while some adaptor proteins have a limited pattern of expression [Liu & Roth, *Proc. Natl. Acad. Sci. USA* 92: 10287–91 (1995); Nakamura et al., *Oncogene* 13: 1111–21 (1996)], many are ubiquitously expressed [Araki et al., *Diabetes* 42: 1041–54 (1993); Frantz et al., *J Bio. Chem.* 272: 2659–67 (1997)]. Thus, it is not clear how biologically relevant outputs are modulated as cells differentiate.

SUMMARY OF THE INVENTION

Applicants have identified cDNA clone (DNA30676 (SEQ ID NO:2), DNA40575 (SEQ ID NO:4), DNA61601 (SEQ ID NO:6)) that encodes a novel polypeptide, designated in the present application as "PRO201, PRO 308, PRO309," respectively.

In one embodiment, the invention provides an isolated nucleic acid molecule having at least about 80% sequence identity to (a) a DNA molecule encoding a polypeptide comprising the sequence of amino acids 1 to 576 of FIG. 1 (SEQ ID NO: 1), amino acids 1 to 501 of FIG. 2 (SEQ ID NO: 3) or amino acids 1 to 703 of FIG. 3 (SEQ ID NO: 5); or (b) the complement of the DNA molecule of (a). The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 1 to 576 of FIG. 1 (SEQ ID NO: 1), 1 to 501 of FIG. 2, (SEQ ID NO: 3), and 1 to 703 of FIG. 3 (SEQ ID NO: 5). Preferably, the greatest degree of identity occurs in the serine/proline rich domain (i.e., amino acid residues 145–299 of SEQ ID NO: 1, amino acid residues 28–210 of SEQ ID NO: 3 and amino acids 181–415 of SEQ ID NO: 5). Alternatively, the greatest degree of identity occurs in the SH2 domain (i.e., amino acid residues 1–118 of SEQ ID NO:1 and amino acid residues 50–166 of SEQ ID NO: 5) In a further embodiment, the isolated nucleic acid molecule comprises DNA encoding a Nsp polypeptide having amino acid residues: (a) 1 to 576 of FIG. 1 (SEQ ID NO: 1), (b) 1 to 501 of FIG. 2 (SEQ ID NO: 3), or (c) 1 to 703 of FIG. 3 (SEQ ID NO: 5); or is complementary to such encoding nucleic acid sequence, and remains stably bound to it under at least moderate, and optionally, under high stringency conditions. In another aspect, the invention provides a nucleic acid of the full length protein of clones DNA30676-1223 (SEQ ID NO:2), DNA40575-1223 (SEQ ID NO: 4) and DNA61601-1223 (SEQ ID NO:6), deposited with the ATCC under accession number ATCC 209567, ATCC 209565 and ATCC 209713, respectively, alternatively the coding sequence of clones DNA30676-1223, DNA40575-1223 and DNA61601-1223, deposited under accession number ATCC 209567, ATCC 209565 and ATTC 209713, respectively.

In yet another embodiment, the invention provides a vector comprising DNA encoding a PRO201, PRO 308, or PRO309 polypeptide. A host cell comprising such a vector is also provided. By way of example, the host cells may be CHO cells, *E. col,* or yeast. A process for producing PRO201, PRO308 or PRO309 polypeptides is further provided and comprises culturing host cells under conditions suitable for expression of PRO201, PRO308 or PRO309 and recovering the same from the cell culture.

In yet another embodiment, the invention provides isolated PRO201, PRO308 or PRO309 polypeptide. In particular, the invention provides isolated native sequence PRO201, PRO308 OR PRO309 polypeptide, which in one embodiment, includes an amino acid sequence comprising residues 1 to 576 of FIG. 1 (SEQ ID NO: 1); 1 to 501 of FIG. 2 (SEQ ID NO: 3) or 1 to 703 of FIG. 3 (SEQ ID NO: 5). Native PRO201, PRO308 or PRO309 polypeptides with or without the initiating methionine are specifically included. Alternatively, the invention provides a PRO201, PRO308 or PRO309 polypeptide encoded by the nucleic acid deposited under accession number ATCC 209567, ATCC 209565 and ATTC209713, respectively.

In yet another embodiment, the invention provides chimeric molecules comprising a PRO201, PRO308 or PRO309 polypeptide fused to a heterologous polypeptide or amino acid sequence. An example of such a chimeric molecule comprises a PRO201, PRO308 OR PRO309 polypeptide fused to an epitope tag sequence or an Fc region of an immunoglobulin.

In yet another embodiment, the invention provides an antibody which specifically binds to PRO201, PRO308 or PRO309 polypeptide. Optionally, the antibody is a monoclonal antibody.

In yet another embodiment, the invention provides for compounds and methods for developing antagonists against and agonists promoting the Nsp1, Nsp2 and/or Nsp3 modulated cellular signaling. In particular, an antagonist of Nsp 1, Nsp2 and/or Nsp3 which blocks, inhibits and/or neutralizes the normal functioning of the latter compounds in cellular signaling., including both small bioorganic molecules and antisense nucleotides.

In yet another embodiment, the invention provides for alternatively spliced variants of PRO201, 308 or PRO309.

BRIEF DESCRIPTION OF THE DRAWINGS

FIGS. 1A–1C shows both the nucleic acid sequence of DNA30676 (SEQ ID NO:2) as well as the encoded amino acid sequence of a native sequence PRO201 polypeptide (SEQ ID NO: 1).

FIGS. 2A–2C shows both the nucleic acid sequence of DNA40575 (SEQ ID NO:4) as well as the encoded amino acid sequence of a native sequence PRO308 polypeptide (SEQ ID NO: 3).

FIGS. 3A–3C show both the nucleic acid sequence of DNA61601 (SEQ ID NO:6)as well as the encoded amino acid sequence of a native sequence PRO309 polypeptide (SEQ ID NO:5).

FIGS. 4A–C shows the sequences of 1328938, 104191 and 1651811 (SEQ ID NOS:13–15), respectively, of the (LIFESEQ™ database, Incyte Pharmaceuticals, Palo Alto, Calif.), which were used to isolate the full length DNA30676, DNA40575 and DNA61601 nucleic acid sequences of the invention.

FIG. 5A shows the oligonucleotide sequences (SEQ ID NO: 7, SEQ ID NO: 8) which were used in the isolation of DNA30676. FIG. 5B shows the oligonucleotide sequences (SEQ ID NO: 9, SEQ ID NO: 10) which were used in the isolation of DNA40575. FIG. 5C shows the oligonucleotide sequences (SEQ ID NO: 11, SEQ ID NO: 12) which were used in the isolation of DNA61601.

FIG. 6A shows a figurative illustrative comparison of the various domains between a native sequence Nsp1 (SEQ ID NO:1), a native sequence Nsp2 (SEQ ID NO:3) and a native sequence Nsp3 (SEQ ID NO:5);

FIG. 6B show an actual comparison between the 3 sequences themselves introducing gaps, as necessary in order to maximize the overall degree of identity between the three sequences.

FIG. 7 shows the sequence of a native sequence Nsp1 (SEQ ID NO:1) wherein the SH2 regions is identified by overscore and the prolines and serines of the P/S region are indicated in single and double underline, respectively.

FIG. 8 shows a comparison of a native sequence Nsp1 (SEQ ID NO:1) with human Shc (SEQ ID NO:16), Sck (SEQ ID NO:17) and Fes (SEQ ID NO:18) proteins.

DETAILED DESCRIPTION OF THE PREFERRED EMBODIMENTS

1. Definitions

Figure 9A:
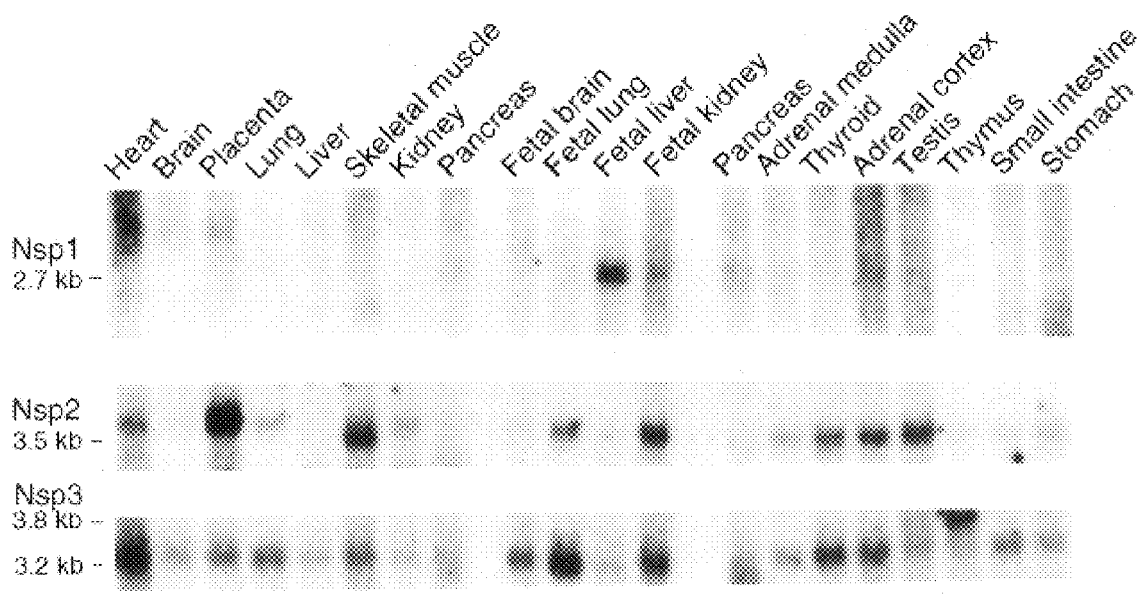
FIG. 9A is a northern blot showing significant expression of a native sequence Nsp1 (SEQ ID NO:1) in human fetal liver, while a native sequence Nsp2 (SEQ ID NO:3) and a native sequence Nsp3 (SEQ ID NO:5) were more widely expressed.

The terms "PRO201, PRO308 or PRO309," "PRO201, PRO308 or PRO309 polypeptide" and "Nsp1, Nsp2 or Nsp3," respectively, when used herein encompass native sequence PRO201, PRO308 or PRO309, respectively, and PRO201, PRO308 or PRO309 variants, respectively, (which are further defined herein). The may be isolated from a variety of sources, such as from human tissue types or from another source, or prepared by recombinant or synthetic methods.

Figure 1A:
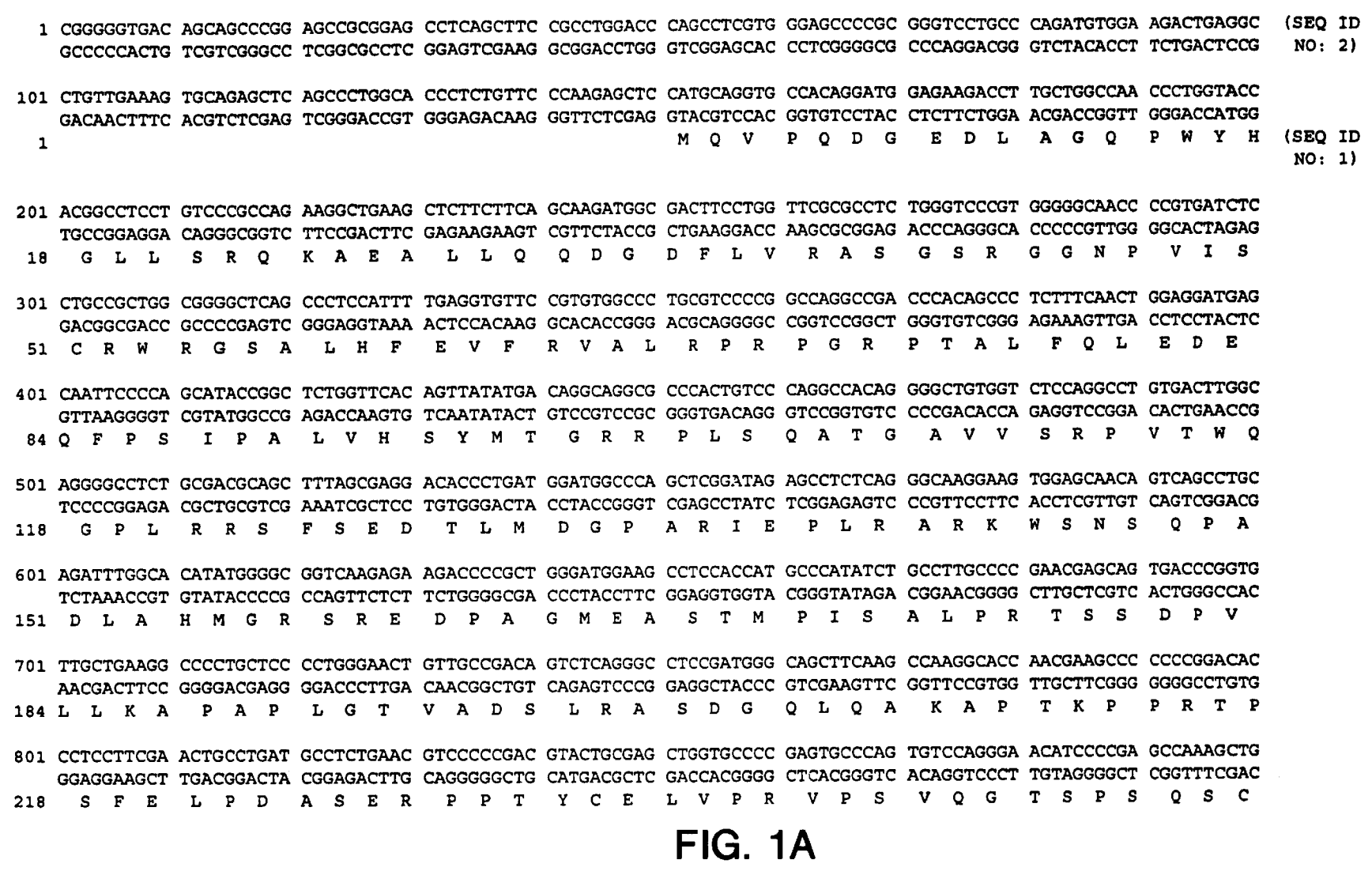

A "native sequence PRO201, PRO308 or PRO309" comprises a polypeptide having the same amino acid sequence as a PRO201, PRO308 or PRO309 derived from nature. Such native sequence PRO201, PRO308 or PRO309 can be isolated from nature or can be produced by recombinant or synthetic means. The term "native sequence PRO201, PRO308 or PRO309" specifically encompasses naturally-occurring truncated or secreted forms of PRO201, PRO308 or PRO309 (e.g., an extracellular domain sequence), naturally-occurring variant forms (e.g., alternatively spliced forms) and naturally-occurring allelic variants of PRO201, PRO308 or PRO309. In one embodiment of the invention, the native sequence PRO201, PRO308 or PRO309 is a mature or full-length native sequence PRO201, PRO308 or PRO309 comprising: (a) amino acids 1 to 576 of FIG. 1 (SEQ ID NO: 1); (b) amino acids 1 to 501 of FIG. 2 (SEQ ID NO: 3) and (c) amino acids 1 to 703 of FIG. 3 (SEQ ID NO: 5), respectively, with or without the N-terminal signal sequence, and with or without the initiating methionine at position 1.

"PRO201, PRO308 or PRO309 variant" means an active PRO201, PRO308 or PRO309 as defined below having at least about 80% amino acid sequence identity to: (a) a DNA molecule encoding a PRO201, PRO308 or PRO309 polypeptide, with or without its native signal sequence, or (b) the complement of the DNA molecule of (a). In a particular embodiment, the PRO201, PRO308 or PRO309 variant has at least about 80% amino acid sequence homology with the PRO201, PRO308 or PRO309 having the deduced amino acid sequence shown in FIG. 1 (SEQ ID NO: 1, FIG. 2 (SEQ ID NO: 3) or FIG. 3 (SEQ ID NO: 5) respectively for a full-length native sequence PRO201, PRO308 or PRO309. Such PRO201, PRO308 or PRO309 variants include, for instance, PRO201, PRO308 or PRO309 polypeptides wherein one or more amino acid residues are added, or deleted, at the N- or C-termninus of the sequence of FIG. 1 (SEQ ID NO:1), FIG. 2 (SEQ ID NO: 3) or FIG. 3 (SEQ ID NO: 5) respectively. Preferably, the nucleic acid or amino acid sequence identity is at least about 85%, more preferably at least about 90%, and even more preferably at least about 95%.

"Percent (%) amino acid sequence identity" with respect to the PRO201, PRO308 or PRO309 sequences identified herein is defined as the percentage of amino acid residues in a candidate sequence that are identical with the amino acid residues in the PRO201, PRO308 or PRO309 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST-2 software set to the default parameters. Those skilled in the art can determine appropriate parameters for measuring alignment, including any algorithms needed to achieve maximal alignment over the full length of the sequences being compared.

"Percent (%) nucleic acid sequence identity" with respect to the PRO201, PRO308 or PRO309 sequences identified herein is defined as the percentage of nucleotides in a candidate sequence that is identical with the nucleotides in the PRO201, PRO308 or PRO309 sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST-2 software set the default parameters. Those skilled in the art can determine appropriate parameters for measuring alignment, including any algorithms needed to achieve maximal alignment over the full length of the sequences being compared.

"Isolated," when used to describe the various polypeptides disclosed herein, means polypeptide that has been identified and separated and/or recovered from a component of its natural environment Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO201, PRO308 or PRO309 natural environment will not be present. Ordinarily, however, isolated polypeptide will be prepared by at least one purification step.

An "isolated" DNA30676 (SEQ ID NO:2), DNA40575 (SEQ ID NO:4) or DNA61601 (SEQ ID NO:6) nucleic acid molecule is a nucleic acid molecule that is identified and separated from at least one contaminant nucleic acid molecule with which it is ordinarily associated in the natural source of the DNA30676, DNA40575 or DNA61601 nucleic acid. An isolated DNA30676 SEQ ID NO:2, DNA40575 or DNA61601 nucleic acid molecule is other than in the form or setting in which it is found in nature. Isolated DNA30676, DNA40575 or DNA61601 nucleic acid molecules therefore are distinguished from the DNA30676, DNA40575 or DNA61601 nucleic acid molecule as it exists in natural cells. However, an isolated DNA30676, DNA40575 or DNA61601 nucleic acid molecule includes DNA30676, DNA40575 or DNA61601 nucleic acid molecules contained in cells that ordinarily express DNA30676, DNA40575 or DNA61601 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-PRO201, anti-PRO308 or anti-PRO309 monoclonal antibodies (including agonist, antagonist, and neutralizing antibodies) and anti-PRO201, anti-PRO308 or anti-PRO309 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" for the purposes herein refers to form(s) of PRO201, PRO308 or PRO309 which retain the biologic and/or immunologic activities of native or naturally-occurring PRO201, PRO308 or PRO309. A preferred activity is the ability to bind to and affect, e.g., block or otherwise modulate, an activity of cellular response to external signaling. The activity preferably involves the regulation of tumorigenesis and response to stimulation by integrin receptors and by epidermal growth factor (EGF), insulin growth factor (IGF) and through other receptor tyrosine (RTK) ligands.

The term "modulate" means to affect (eg., either upregulate, downregulate or otherwise control) the level of a signaling pathway. Cellular processes under the control of signal transduction include, but are not limited to, transcription of specific genes, normal cellular functions, such as metabolism, proliferation, differentiation, adhesion, apoptosis and survival, as well as abnormal processes, such as transformation, blocking of differentiation and metastasis.

The term "antagonist" is used herein in the broadest sense to include any molecule which blocks, prevents, inhibits, or neutralizes the process by which the Nsp1, Nsp2 and Nsp3 molecules of the invention that interferes with the interaction of any of the protein domains of Nsp1, Nsp2 and Nsp3 with various target proteins. Such interactions can generally occur with the C-terminal end of Nsp1, Nsp2, Nsp3, or specifically the SH2 and/or proline/serine (P/S) rich regions with phosphotyrosyl residues and polyproline motifs with a target binding site. In a similar manner, the term "agonist" is used herein to include any molecule which promotes, enhances or stimulates the interaction of the protein domains of Nsp1, Nsp2 and Nsp3 including the SH2 and/or proline/serine (P/S) rich regions with phosphotyrosyl residues and polyproline motifs, respectively on various target proteins. Suitable molecules that affect the interaction of the SH2 and/or P/S regions of Nsp1, Nsp2, Nsp3 and the phosphotyrosyl residues and polyproline motifs, respectively or target proteins include fragments of the latter or small bioorganic molecules, e.g., peptidomimetics, which will prevent or enhance, as the case may be, the interaction. Non-limiting examples include proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Another preferred form of antagonist includes antisense nucleotides that inhibit the Nsp1, Nsp2 or Nsp3 modulated signaling. Preferred forms bind to specific regions on either Nsp1, Nsp2 or Nsp3 or the targets with which Nsp 1, Nsp2 or Nsp3 interact.

II. Compositions and Methods of the Invention

A. Full-length Nsp1, Nsp2 or Nsp3

The present invention provides newly identified and isolated nucleotide sequences encoding polypeptides referred to in the present application as PRO201 (Nsp1), PRO308 (Nsp2) or PRO309 (Nsp3). In particular, Applicants have identified and isolated cDNA encoding a PRO201, PRO308 and PRO309 polypeptide, as disclosed in further detail in the Examples below. Using the BLAST-2 sequence alignment computer program set to the default parameters, Applicants found that a full-length native sequence PRO201 and PRO309 (shown in FIGS. 6A & 6B and SEQ ID NO: 1–6) have regions of SH2 homology and PRO201, PRO308 and PRO309 have a proline/serine rich (P/S) region homology. SH2 domains are known to bind specific phosphotyrosyl residues, while the P/S region could be a potential SH3 interaction domain. Accordingly, it is presently believed that PRO201, PRO308 and PRO309 disclosed in the present application are newly identified family of adaptor proteins and may possess properties which modulate intracellular signaling pathways.

B. PRO201, PRO308 or PRO309 Variants

In addition to the full-length native sequence PRO201, PRO308 and PRO309 described herein, it is contemplated that PRO201, PRO308 and PRO309 variants can be prepared. PRO201, PRO308 and PRO309 variants can be prepared by introducing appropriate nucleotide changes into the PRO201, PRO308 or PRO309 DNA, or by synthesis of the desired PRO201, PRO308 or PRO309 polypeptides. Those skilled in the art will appreciate that amino acid changes may alter post-translational processes of the PRO201, PRO308 or PRO309, such as changing the number or position of glycosylation sites or altering the membrane anchoring characteristics.

Variations in the native full-length sequence PRO201, PRO308 or PRO309 or in various domains of the PRO201, PRO308 or PRO309 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO201, PRO308 or PRO309 that results in a change in the amino acid sequence of the PRO201, PRO308 or PRO309 as compared with the native sequence PRO201, PRO308 or PRO309. Optionally the variation is by substitution of at least one amino acid with any other amino acid in one or more of the domains of the PRO201, PRO308 or PRO309. Guidance in determining which amino acid residue may be inserted, substituted or deleted without adversely affecting the desired activity may be found by comparing the sequence of the PRO201, PRO308 or PRO309 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA.* 317:415 (1986)] or other known techniques can be performed on the cloned DNA to produce the PRO201, PRO308 or PRO309 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins,* (W.H. Freeman & Co., N.Y.); Chothia, *J. Mol. Biol.* 150:1 (1976)]. If alanine substitution does not yield adequate amounts of variant, an isoteric amino acid can be used.

C. Modifications of PRO201. PRO308 OR PRO309

Covalent modifications of PRO201, PRO308 or PRO309 are included within the scope of this invention. One type of covalent modification includes reacting targeted amino acid residues of the PRO201, PRO308 or PRO309 with an organic derivatizing agent that is capable of reacting with selected side chains or the N- or C-terminal residues of the PRO201, PRO308 or PRO309. Derivatization with bifunctional agents is useful, for instance, for crosslinking PRO201, PRO308 or PRO309 to a water-insoluble support matrix or surface for use in the method for purifying anti-PRO201, PRO308 or PRO309 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the PRO201, PRO308 or PRO309 polypeptide included within the scope of this invention comprises altering the native glycosylation pattern of the polypeptide. "Altering the native glycosylation pattern" is intended for purposes herein to mean deleting one or more carbohydrate moieties found in native sequence PRO201, PRO308 or PRO309, and/or adding one or more glycosylation sites that are not present in the native sequence PRO201, PRO308 or PRO309, and/or alteration of the ratio and/or composition of the sugar residues attached to the glycosylation site(s).

Addition of glycosylation sites to the PRO201, PRO308 or PRO309 polypeptide may be accomplished by altering the amino acid sequence. The alteration may be made, for example, by the addition of, or substitution by, one or more serine or threonine residues to the native sequence PRO201, PRO308 or PRO309 (for O-linked glycosylation sites). The PRO201, PRO308 or PRO309 amino acid sequence may optionally be altered through changes at the DNA level, particularly by mutating the DNA encoding the PRO201, PRO308 or PRO309 polypeptide at preselected bases such that codons are generated that will translate into the desired amino acids.

Another means of increasing the number of carbohydrate moieties on the PRO201, PRO308 or PRO309 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259–306 (1981).

Removal of carbohydrate moieties present on the PRO201, PRO308 or PRO309 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO201, PRO308 or PRO309 comprises linking the PRO201, PRO308 or PRO309 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The PRO201, PRO308 or PRO309 of the present invention may also be modified in a way to form a chimeric molecule comprising PRO201, PRO308 or PRO309 fused to another, heterologous polypeptide or amino acid sequence. In one embodiment, such a chimeric molecule comprises a fusion of the PRO201, PRO308 or PRO309 with a tag polypeptide which provides an epitope to which an anti-tag antibody can selectively bind. The epitope tag is generally placed at the amino- or carboxyl- terminus of the PRO201, PRO308 or PRO309. The presence of such epitope-tagged forms of the PRO201, PRO308 or PRO309 can be detected using an antibody against the tag polypeptide. Also, provision of the epitope tag enables the PRO201, PRO308 or PRO309 to be readily purified by affinity purification using an anti-tag antibody or another type of affinity matrix that binds to the epitope tag. In an alternative embodiment, the chimeric molecule may comprise a fusion of the PRO201, PRO308 or PRO309 with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

D. Preparation of PRO201 PRO308 OR PRO309

The description below relates primarily to production of PRO201, PRO308 OR PRO309 by culturing cell transformed or transfected with a vector containing PRO201, PRO308 OR PRO309 nucleic acid. It is, of course, contemplated that alternative methods, which are well known in the art, may be employed to prepare PRO201, PRO308 or PRO309. For instance, the PRO201, PRO308 or PRO309 sequence, or portions thereof, may be produced by direct peptide synthesis using solid-phase techniques [see, e.g., Stewart et al., *Solid-Phase Peptide Synthesis* W.H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO201, PRO308 or PRO309 may be chemically synthesized separately and combined using chemical or enzymatic methods to produce the full-length PRO201, PRO308 or PRO309.

1. Isolation of DNA Encoding PRO201, PRO308 or PRO309

DNA encoding PRO201, PRO308 or PRO309 may be obtained from a cDNA library prepared from tissue believed to possess the PRO201, PRO308 or PRO309 mRNA and to express it at a detectable level. Accordingly, human PRO201, PRO308 or PRO309 DNA can be conveniently obtained from a cDNA library prepared from human tissue, such as described in the Examples. The PRO201, PRO308 or PRO309-encoding gene may also be obtained from a genomic library or by oligonucleotide synthesis.

Libraries can be screened with probes (such as antibodies to the PRO201, PRO308 or PRO309 or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO201, PRO308 or PRO309 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO201, PRO308 OR PRO309 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, CaPO4 and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterizim tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact.* 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1 776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for PRO201, PRO308 OR PRO309-encoding vectors. *Saccharomnyces cerevisiae* is a commonly used lower eukaryotic host microorganism.

Suitable host cells for the expression of glycosylated PRO201, PRO308 OR PRO309 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Renlicable Vector

The nucleic acid (e.g., cDNA or genomic DNA) encoding PRO201, PRO308 OR PRO309 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO201, PRO308 or PRO309 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO201, PRO308 or PRO309 DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the C. albicans glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, eg., the gene encoding D-alanine racemase for Bacilli.

An example of suitable selectable markers for mammalian cells are those that enable the identification of cells competent to take up the PRO201, PRO308 or PRO309 nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trpl gene present in the yeast plasmid YRp7 [Stinchcomb et al., Nature, 282:39 (1979); Kingsman et al., Gene, 2:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 [Jones, Genetics, 85:12 (1977)].

Expression and cloning vectors usually contain a promoter operably linked to the PRO201, PRO308 or PRO309 nucleic acid sequence to direct mRNA synthesis. Promoters recognized by a variety of potential host cells are well known. Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21–25 (1983)]. Promoters for use in bacterial systems also will contain a Shine-Dalgarno (S.D.) sequence operably linked to the DNA encoding PRO201, PRO308 or PRO309.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO201, PRO308 or PRO309 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO201, PRO308 or PRO309 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO201, PRO308 or PRO309 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO201, PRO308 or PRO309.

Still other methods, vectors, and host cells suitable for adaptation to the synthesis of PRO201, PRO308 or PRO309 in recombinant vertebrate cell culture are described in Gething et al., Nature 293:620–625 (1981); Mantei et al., Nature, 281:4046 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO201, PRO308 or PRO309 polypeptide or against a synthetic peptide based on the DNA sequences provided herein or against exogenous sequence fused to PRO201, PRO308 or PRO309 DNA and encoding a specific antibody epitope.

5. Purification of Polypeptide

Forms of PRO201, PRO308 or PRO309 may be recovered from culture medium or from host cell lysates. If membrane-bound, it can be released from the membrane using a suitable detergent solution (eg. Triton-X 100) or by enymatic cleavage. Cells employed in expression of PRO201, PRO308 or PRO309 can be disrupted by various physical or chemical means, such as freeze-thaw cycling, sonication, mechanical disruption, or cell lysing agents.

It may be desired to purify PRO201, PRO308 or PRO309 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO201, PRO308 or PRO309. Various methods of protein purification may be employed and such methods are known in the art and described for example in Deutscher, Methods in Enzymology, 182 (1990); Scopes, *Protein Purification: Principles and Practice*, Springer-Verlag, New York (1982). The purification step(s) selected will depend, for example, on the nature of the production process used and the particular PRO201, PRO308 or PRO309 produced.

E. Uses for PRO201, PRO308 OR PRO309

Nucleotide sequences (or their complement) encoding PRO201, PRO308 or PRO309 have various applications in the art of molecular biology, including uses as hybridization probes, in chromosome and gene mapping and in the generation of anti-sense RNA and DNA. PRO201, PRO308 or PRO309 nucleic acid will also be useful for the preparation of PRO201, PRO308 or PRO309 polypeptides by the recombinant techniques described herein.

Figure 3A:
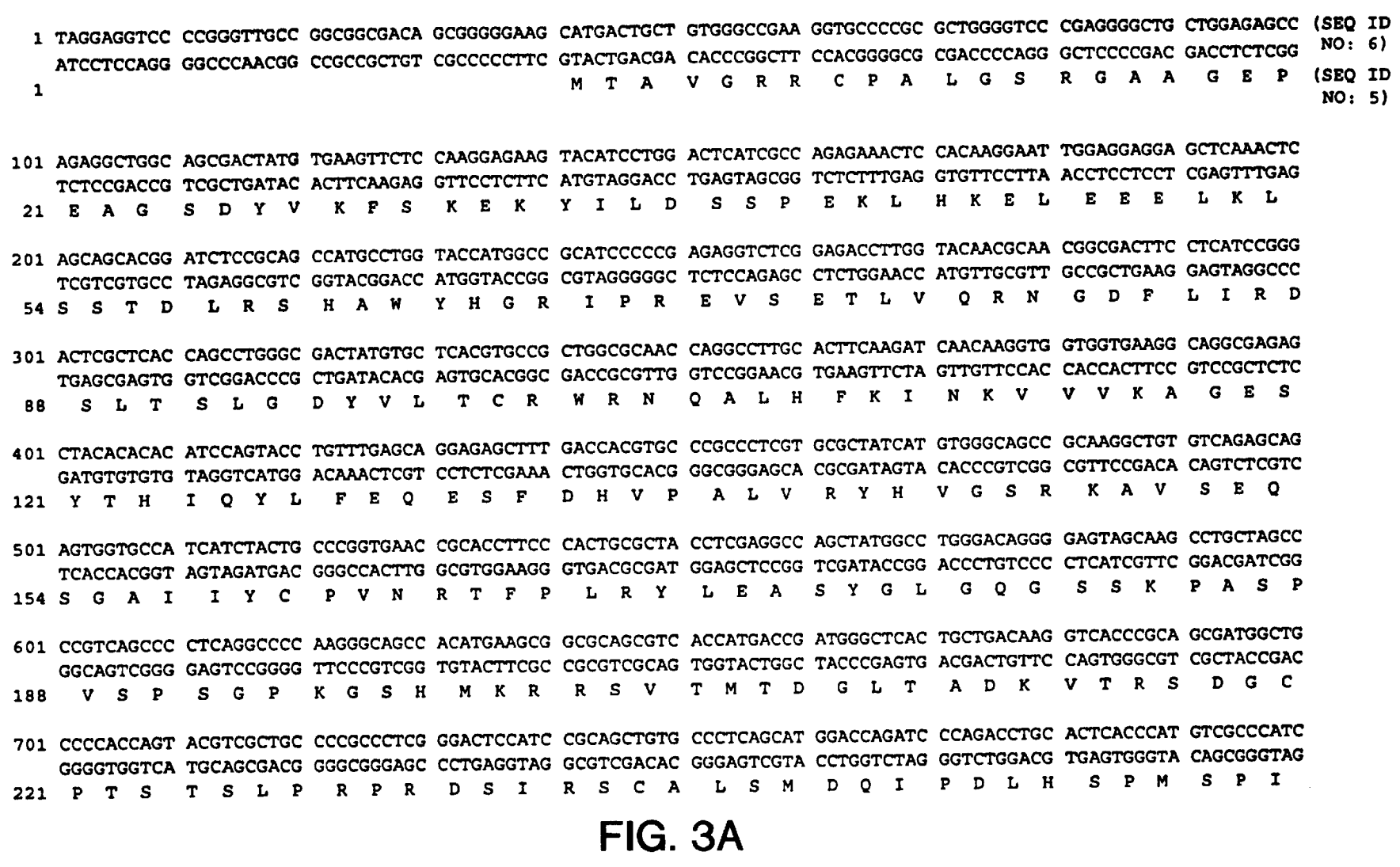

The full-length native sequence PRO201, PRO308 or PRO309 (SEQ ID NO:1, 3 & 5) gene, or portions thereof, may be used as hybridization probes for a cDNA library to isolate the full-length gene or to isolate still other genes (for instance, those encoding naturally-occurring variants of PRO201, PRO308 or PRO309 or PRO201, PRO308 or PRO309 from other species) which have a desired sequence identity to the PRO201, PRO308 or PRO309 sequence disclosed in FIG. 1–3 (SEQ ID NO: 1, 3 & 5). Optionally, the length of the probes will be about 20 to about 50 bases. The hybridization probes may be derived from the nucleotide sequence of SEQ ID NO: 1, 3 or 5 or from genomic sequences including promoters, enhancer elements and introns of native sequence PRO201, PRO308 or PRO309. By way of example, a screening method will comprise isolating the coding region of the PRO201, PRO308 or PRO309 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidintbiotin coupling systems. Labeled probes having a sequence complementary to that of the PRO201, PRO308 or PRO309 gene of the present invention can be used to screen libraries of human cDNA, genomic DNA or mRNA to determine which members of such libraries the probe hybridizes to. Hybridization techniques are described in further detail in the Examples below.

The probes may also be employed in PCR techniques to generate a pool of sequences for identification of closely related PRO201, PRO308 or PRO309 sequences.

Nucleotide sequences encoding a PRO201, PRO308 or PRO309 can also be used to construct hybridization probes for mapping the gene which encodes that PRO201, PRO308 or PRO309 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO201, PRO308 or PRO309 encode a protein which binds to another protein (example, where the PRO201, PRO308 or PRO309 is a receptor), the PRO201, PRO308 or PRO309 can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO201, PRO308 or PRO309 can be used to isolate correlative ligand(s). Screening assays can be designed to find lead compounds that mimic the biological activity of a native PRO201, PRO308 or PRO309 or a receptor for PRO201, PRO308 or PRO309. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO201, PRO308 or PRO09 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO201, PRO308 or PRO309 can be used to clone genomic DNA encoding PRO201, PRO308 or PRO309 in accordance with established techniques and the genomic sequences used to generate transgenic animals that contain cells which express DNA encoding PRO201, PRO308 or PRO309. Methods for generating transgenic animals, particularly animals such as mice or rats, have become conventional in the art and are described, for example, in U.S. Pat. Nos. 4,736,866 and 4,870,009. Typically, particular cells would be targeted for PRO201, PRO308 or PRO309 transgene incorporation with tissue-specific enhancers. Transgenic animals that include a copy of a transgene encoding PRO201, PRO308 or PRO309 introduced into the germ line of the animal at an embryonic stage can be used to examine the effect of increased expression of DNA encoding PRO201, PRO308 or PRO309. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Non-human homologues of PRO201, PRO308 or PRO309 can be used to construct a PRO201, PRO308 or PRO309 "knock out" animal which has a defective or altered gene encoding PRO201, PRO308 or PRO309 as a result of homologous recombination between the endogenous gene encoding PRO201, PRO308 or PRO309 and altered genomic DNA encoding PRO201, PRO308 or PRO309 introduced into an embryonic cell of the animal. For example, cDNA encoding PRO201, PRO308 or PRO309 can be used to clone genomic DNA encoding PRO201, PRO308 or PRO309 in accordance with established techniques. A portion of the genomic DNA encoding PRO201, PRO308 or PRO309 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO201, PRO308 or PRO309 polypeptide.

DNA30676 contains a single long open reading frame which can encode a 576 amino acid protein, herein termed Nsp1 (novel SH2 containing protein) (FIG. 1, SEQ ID NO: 2). Nsp1 is related to Sck and Shc (See FIG. 8) as determined by the indicated N-terminal homology. Nsp1 also contains a proline-serine rich domain (P/S) in the middle of the protein that may function as an SH3 interaction domain. The C terminus of the protein has no obviously relevant homology to any known mammalian proteins. Nsp1, Nsp2 and Nsp3 share an overall homology between 33 and 47%. Nsp3 has an SH2 domain and a potential SH3 interaction domain, while Nsp2 lacks the SH2 domain but does have a potential SH3 interaction domain. The absence of the SH2 domain in Nsp2 is suggestive that this protein could act as a dominant negative regulator of the other two Nsps. The lack of any apparent kinase or phosphatase domain suggests that they represent a novel family of adaptor proteins.

Adapter proteins are believed to play a significant role integrating multiple signaling cascades and in determining specific response to extracellular stimuli. Signals generated by growth factors such as EGF or IGF-1 through receptor tyrosine kinases or by extracellular matrix components acting through the integrin receptors can induce cytoskeletal changes. Applicants have shown that the EGF receptor coimmunoprecipitates with Nsp1 and is phosphorylated in response to EGF signaling. Thus, antagonists of Nsp1 would be expected to be useful to inhibit cellular response attributed to stimulation by growth factors such as EGF or IGF-1 (e.g., tumorigenesis).

Several characteristics suggest that Nsp1 could play an important role in modulating the response to external stimuli. Nsp1 is phosphorylated in response to EGF stimulation and forms a complex that includes the EGF receptor, PI3 kinase and Cas. The Nsp1/Cas complex also responds to signaling through the fibronectin receptor. However, the stoichiometry of the interaction and the phosphorylation status of the components differs between the two stimuli. The implication is that that biological outcome in response to these extracellular signals could be quite distinct in the presence or absence of Nsp1. For example, FAK associates with the SH3 region of Cas via a PXXP region at the C-terminus of FAK (P(715)SRP - mouse nomenclature (Harte et al., *J. Biol. Chem.* 271: 13649–55 (1996). There are six PXXP signatures in Nsp1. This raises the possibility that Nsp1 could compete for the SH3 region on Cas and decrease the amount of Fak that is bound to Cas and so alter Fak dependent events. The data also point to an EGF mediated decrease in the extent of phosphorylation of the Cas that is associated with Nsp1. This complex then is likely to have a decrease in the number of proteins associated with the phosphorylated tyrosines of the Cas and so lead to changes in downstream events. As Nsp1 expression is highest in fetal tissues this protein could potentially have an important role in mediating the developmental readout of extracellular signals.

F. Anti-PRO201, PRO308 or PRO309 Antibodies

The present invention further provides anti-PRO201, anti-PRO308 or anti-PRO309 antibodies. Exemplary antibodies include polyclonal, monoclonal, humanized, bispecific, and heteroconjugate antibodies.

1. Polyclonal Antibodies

The anti-PRO201, anti-PRO308 or anti-PRO309 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO201, PRO308 or PRO309 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO201, anti-PRO308 or anti-PRO309 antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO201, PRO308 or PRO309 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51–63].

The culture medium in which the hybridoma cells are cultured can then be assayed for the presence of monoclonal antibodies directed against PRO201, PRO308 or PRO309. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinkinga.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-PRO201, PRO308 or PRO309 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522–525 (1986); Riechmann et al., *Nature,* 332:323–329 (1988); and Presta, *Curr. Op. Struct. Biol.,* 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and coworkers [Jones et al., *Nature,* 321:522–525 (1986); Riechmann et al., *Nature,* 332:323–327 (1988); Verhoeyen et al., *Science* 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al. and Boerner et al. are also available for the preparation of human monoclonal antibodies (Cole et al., *Monoclonal Antibodies and Cancer Therapy,* Alan R. Liss, p. 77 (1985) and Boerner et al., *J. Immunol.,* 147(1):86–95 (1991)].

4. Bispecific Antibodies

Bispecific antibodies are monoclonal, preferably human or humanized, antibodies that have binding specificities for at least two different antigens. In the present case, one of the binding specificities is for the PRO201, PRO308 or PRO309, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Trauneckeret al., *EMBO J.,* 10:3655–3659(1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl4-mercaptobutyrimidate and those disclosed, for example, in U.S. Pat. No. 4,676,980.

G. Uses for anti-PRO201, PRO308 or PRO309 Antibodies

The anti-PRO201, anti-PRO308 or anti-PRO309 antibodies of the invention have various utilities. For example, anti-PRO201, anti-PRO308 or anti-PRO309 antibodies may be used in diagnostic assays for PRO201, PRO308 or PRO309, eg., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques,* CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^{3}$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-PRO201, anti-PRO308 or anti-PRO309 antibodies also are useful for the affinity purification of PRO201, PRO308 or PRO309 from recombinant cell culture or natural sources. In this process, the antibodies against PRO201, PRO308 or PRO309 are immobilized on a suitable support, such a Sephadex resin or filter paper, using methods well known in the art. The immobilized antibody then is contacted with a sample containing the PRO201, PRO308 or PRO309 to be purified, and thereafter the support is washed with a suitable solvent that will remove substantially all the material in the sample except the PRO201, PRO308 or PRO309, which is bound to the immobilized antibody. Finally, the support is washed with another suitable solvent that will release the PRO201, PRO308 or PRO309 from the antibody.

Anti-PRO201, anti-PRO308 or anti-PRO309 would also have similar utilities to those articulated under uses for PRO201, PRO308 and PRO309 polypeptides.

H. PRO201, PRO308 and PRO309 Antagonists

Several approaches may be suitably employed to create the antagonist and agonist compounds of the present invention. Any approach where the antagonist molecule can be targeted to the interior of the cell, which interferes or prevents wild type PRO201, PRO308 or PRO309 from normal operation is suitable. Additional properties of such antagonist or agonist molecules are readily determninable by one of ordinary skill, such as size, charge and hydrophobicity suitable for transmembrane transport.

Where mimics or other mammalian homologues of PRO201, PRO308 or PRO309 are to be identified or evaluated, the cells are exposed to the test compound and compared to positive controls which are exposed only to PRO201, PRO308 or PRO309 and to negative controls which were not exposed to either the compound or the natural ligand. Where antagonists or agonists of PRO201, PRO308 or PRO309 signal modulation are to be identified or evaluated, the cells are exposed to the compound of the invention in the presence of the natural ligand and compared to controls which are not exposed to the test compound.

Detection assays may by employed as a primary screen to evaluate the phosphatase inhibition/enhancing activity of the antagonist/agonist compounds of the invention. The assays may also be used to assess the relative potency of a compound by testing a range of concentrations, in a range from 100 mM to 1 pM, for example, and computing the concentration at which the amount of phosphorylation or signal transduction is reduced or increased by 50% ($IC_{50}$) compared to controls.

Assays can be performed to identify compounds that affect phosphorylation of PRO201, PRO308 or PRO309 substrates. Specifically, assays can be performed to identify compounds that increase the phosphorylation activity of PRO201, PRO308 or PRO309 or assays can be performed to identify compounds that decrease the phosphorylation of PRO201, PRO308 or PRO309 substrates. These assays can be performed either on whole cells themselves or on cell extracts. The assays can be performed in a variety of formats, including protein-protein binding assays, biochemical screening assays, immunoassays, cell based assays, etc. Such assay formats are well known in the art.

The screening assays of the present invention are amenable to high-throughput screening of chemical libraries, and are particularly suitable for identifying small molecule drug candidates.

(1) Antagonist and agonist molecules

To screen for antagonists and/or agonists of PRO201, PRO308 or PRO309 signaling, the assay mixture is incubated under conditions whereby, but for the presence of the candidate pharmacological agent, PRO201, PRO308 or PRO309 induces intracellular signaling (for example, association of Nsp1 with the EGF receptor) with a reference activity. The mixture components can be added in any order that provides for the requisite activity. Incubation may be performed at any temperature that facilitates optimal binding, typically between about 4° and 40° C., more commonly between about 15° and 40° C. Incubation periods are likewise selected for optimal binding but also minimized to facilitate rapid, high-throughput screening, and are typically between about 0.1 and 10 hours, preferably less than 5 hours, more preferably less than 2 hours. After incubation, the effect of the candidate pharmacological agent on the PRO201, PRO308 or PRO309 signaling is determined in any convenient way. For cell-free binding-type assays, a separation step is often used to separate bound and unbound components. Separation may, for example, be effected by precipitation (e.g. TCA precipitation, immunoprecipitation, etc.), immobilization (e.g. on a solid substrate), followed by washing. The bound protein is conveniently detected by taking advantage of a detectable label attached to it, e.g. by measuring radioactive emission, optical or electron density, or by indirect detection using, e.g. antibody conjugates.

Suitable molecules that affect the protein-protein interaction of PRO201, PRO308 or PRO309 and its binding proteins include fragments of the latter or small molecules, e.g., peptidomimetics, which will prevent interaction and proper complex formation. Such small molecules, which are usually less than 10 K molecular weight, are preferable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Many pharmaceutical companies have extensive libraries of such molecules, which can be conveniently screened by using the assays of the present invention. Non-limiting examples include proteins, peptides, glycoproteins, glycopeptides, glycolipids, polysaccharides, oligosacchardies, nucleic acids, bioorganic molecules, peptidomimetics, pharmacological agents and their metabolites, transcriptional and translation control sequences, and the like.

A preferred technique for identifying molecules which bind to PRO201, PRO308 or PRO309 utilizes a chimeric substrate (e.g., epitope-tagged fused or fused immunoadhesin) attached to a solid phase, such as the well of an assay plate. The binding of the candidate molecules, which are optionally labeled (e.g., radiolabeled), to the immobilized receptor can be measured. Alternatively, competition for interaction of Nsp1 with the binding proteins can be assayed. Further yet, molecules may be screened which affect the tumorigenicity of PRO201, PRO308 or PRO309 in NIH3T3 cells in nude mice. In screening for antagonists and/or agonists, PRO201, PRO308 or PRO309 can be exposed to a PRO201, PRO308 or PRO309 substrate followed by the putative antagonist and/or agonist, or the PRO201, PRO308 or PRO309 binding protein and antagonist and/or agonist can be added simultaneously, and the ability of the antagonist and/or agonist to block PRO201, PRO308 or PRO309 activation can be evaluated.

(2) Detection assays

The PRO201, PRO308 or PRO309 polypeptides are useful in assays for identifying lead compounds for therapeutically active agents that modulate PRO201, PRO308 or PRO309 signaling. Specifically, lead compounds that either prevent the formation of PRO201, PRO308 or PRO309 signaling complexes or prevent or attenuate PRO201, PRO308 or PRO309 modulated can be conveniently identified.

(a) Biochemical detection techniques

Biochemical analysis techniques can be evaluated by a variety of techniques. One typical assay mixture which can be used with the present invention contains PRO201, PRO308 or PRO309 and a protein with which PRO201, PRO308 or PRO309 is normally directly or indirectly associated (e.g. Cas), usually in an isolated, partially pure or pure form. One or both of these components may be PRO201, PRO308 or PRO309 bound to another peptide or polypeptide, which may, for example, provide or enhance protein-protein binding, improve stability under assay conditions, etc. In addition, one of the components usually comprises or is coupled to a detectable label. The label may provide for direct detection by measuring radioactivity, luminescence, optical or electron density, etc., or indirect detection such as an epitope tag, an enzyme, etc. The assay mixture can additionally comprise a candidate pharmacological agent, and optionally a variety of other components, such as salts, buffers, carrier proteins, e.g. albumin, detergents, protease inhibitors, nuclease inhibitors, antimicrobial agents, etc., which facilitate binding, increase stability, reduce non-specific or background interactions, or othervise improve the efficiency or sensitivity of the assay.

The following detection methods may also be used in a cell-free system wherein cell lysate containing the signal transducing substrate molecule and PRO201, PRO308 or PRO309 is mixed with a compound of the invention.

(i) Whole cell detection

A common technique involves incubating cells with vertebrate PRO201, PRO308 or PRO309 and radiolabeled phosphate, lysing the cells, separating cellular protein components of the lysate using an SDS-polyacrylamide gel (SDS-PAGE) technique, in either one or two dimensions, and detecting the presence of phosphorylated proteins by exposing X-ray film. Detection can also be effected without using radioactive labeling. In such a technique, the protein components (e.g., separated by SDS-PAGE) are transferred to a nitrocellulose membrane where the presence of phosphorylated tyrosine is detected using an antiphosphotyrosine antibody (anti-pTyr).

Alternatively, the anti-pTyr can be conjugated with an enzyme, such as horseradish peroxidase, and detected by subsequent addition of a colorimetric substrate for the enzyme. A further alternative involves detecting the anti-pTyr by reacting with a second antibody that recognizes the anti-pTyr, this second antibody being labeled with either a radioactive moiety or an enzyme as previously described. Examples of these and similar techniques are described in Hansen et al., *Electrophoresis* 14: 112–126 (1993); Campbell et al., *J. Biol. Chem.* 268: 7427–7434 (1993); Donato et al., *Cell Growth Diff.* 3: 258–268 (1992); Katagiri et al., *J. Immunol.* 150: 585–593 (1993). Additionally, the anti-pTyr can be detected by labeling it with a radioactive substance, followed by scanning the labeled nitrocellulose to detect radioactivity or exposure of X-ray film.

(b) Biological detection techniques:

The ability of the antagonistlagonist compounds of the invention to modulate the activity PRO201, PRO308 or PRO309, which itself modulates intracellular signaling, may also be measured by scoring for morphological or functional changes associated with ligand binding. Any qualitative or quantitative technique known in the art may be applied for observing and measuring cellular processes which comes under the control of PRO201, PRO308 or PRO309. For example, expression of native sequence Nsp1 (SEQ ID NO:2) in NIH3T. cells causes morphologically transformation of the cells. The presence and or number of these foci can be used as an indicator of biological efficacy of antagonists of agonists of Nsp1 signaling.

The data obtained from these cell culture assays and animal studies can be used in formulating a range of dosages for use in humans. The dosage of the compounds of the invention should lie within a range of circulating concentrations with little or no toxicity. The dosage may vary within this range depending on the dosage form employed and the route of administration.

(2) Antisense nucleotides

Another preferred class of antagonists involves the use of gene therapy techniques, include the administration of antisense nucleotides. Applicable gene therapy techniques include single or multiple administrations of therapeutically effective DNA or mRNA. Antisense RNAs and DNAs can be used as therapeutic agents for blocking the expression of certain genes in vivo. Short antisense oligonucleotides can be imported into cells where they act as inhibitors, despite their low intracellular concentrations caused by restricted uptake by the cell membrane, Zamecnik et al., *Proc. Natl. Acad. Sci. USA* 83: 4143–4146 (1986). The oligonucleotides can be modified to enhance their uptake, e.g., by substituting their negatively charged phophodiester groups by uncharged groups.

There are a variety of techniques known for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection, Dzau et al., *Trends Biotech.* 11: 205–210 (1993). In some situations it is desirable to provide the nucleic acid source with an agent that targets the target cells, such as an antibody specific for a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262: 4429–4432 (1987); Wagner et al., *Proc. Natl. Acad. Sci. USA* 87: 3410–3414 (1990). For a review of known gene marking and gene therapy protocols, see Anderson et al., Science 256: 808–813 (1992).

In one embodiment, PRO201, PRO308 or PRO309 antagonist and/or agonist molecules may be used to bind endogenous ligand in the cell, thereby causing the cell to be unresponsive to PRO201, PRO308 or PRO309 wild type, especially when the levels of PRO201, PRO308 or PRO309 in the cell exceed normal physiological levels. Also, it may be beneficial to bind endogenous PRO201, PRO308 or PRO309 substrates or complexing agents that are activating undesired cellular responses (such as proliferation of tumor cells).

In a further embodiment of the invention, PRO201, PRO308 or PRO309 expression may be reduced by providing PRO201-, PRO308- or PRO309-expressing cells with an amount of PRO201, PRO308 or PRO309 antisense RNA or DNA effective to reduce expression of the PRO201, PRO308 or PRO309 protein.

In a further embodiment of the invention, the expression of binding partners of PRO201, PRO308 or PRO309 may be reduced by providing PRO201, PRO308 or PRO309 expressing cells with an amount of antisense RNA or DNA effective for reduced expression of the binding partners of PRO201, PRO308 or PRO309.

I. Diagnostic Uses

Another use of the compounds of the invention (e.g., PRO201, PRO308 or PRO309, PRO201-, PRO308- or PRO309-variants and anti-PRO201, anti-PRO308 or anti-PRO309 antibodies) described herein is to help diagnose whether a disorder is driven, to some extent, by PRO201, PRO308 or PRO309 modulated signaling.

A diagnostic assay to determine whether a particular disorder is driven by Nsp1, Nsp2 or Nsp3 signaling, can be carried out using the following steps: (1) culturing test cells or tissues; (2) administering a compound which can inhibit Nsp1, Nsp2 or Nsp3 modulated signaling; and (3) measuring the degree of phosphorylation on the PRO201, PRO308 or PRO309 substrate in cell lysates or Nsp1, Nsp2 or Nsp3 mediated phenotypic effects in the test cells. The steps can be carried out using standard techniques in light of the present disclosure. For example, standard techniques can be used to isolate cells or tissues and culturing or in vivo.

Compounds of varying degree of selectivity are useful for diagnosing the role of PRO201, PRO308 or PRO309. For example, compounds which inhibit Nsp 1, Nsp2 or Nsp3 in addition to another form of adaptor molecule can be used as an initial test compound to determine if one of several adaptor molecules drive the disorder. The selective compounds can then be used to further eliminate the possible role of the other adaptor proteins in driving the disorder. Test compounds should be more potent in inhibiting intracellular signaling activity than in exerting a cytotoxic effect (e.g., an $IC_{50}/LD_{50}$ of greater than one). The $IC_{50}$ and $LD_{50}$ can be measured by stand techniques, such as an MTT assay, or by measuring the amount of LDH released. The degree of $IC_{50}/LD_{50}$ of a compound should be taken into account in evaluating the diagnostic assay. Generally, the larger the ratio the more relative the information. Appropriate controls take into account the possible cytotoxic effect of a compound of a compound, such as treating cells not associated with a cell proliferative disorder (e.g., control cells) with a test compound, can also be used as part of the diagnostic assay. The diagnostic methods of the invention involve the screening for agents that modulate the effects of fused upon hedgehog signaling. Exemplary detection techniques include radioactive labeling and immunoprecipitating (U.S. Pat. No. 5,385,915).

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manessas, Va.

Example 1

Isolation of cDNA clones Encoding Human PRO201, PRO308 OR PRO309

An expressed sequence tag (EST) DNA database (LIFESEQTM, Incyte Pharmaceuticals, Palo Alto, Calif.) was searched and an EST was identified (1328938, DNA28710, FIG. 4A (SEQ ID NO:13)) which was in a fetal pancreas library which shared significant identity which the adaptor protein Shc. A full length cDNA corresponding to the isolated EST was cloned from a human fetal kidney library using an in vivo cloning technique (DNA30676, Nsp1 (SEQ ID NO:2)) in pRK5. There is a single long open reading frame which encodes a 576 amino acid protein. This native sequence Nsp1 also is related to Sck and Shc (FIG. 8 (SEQ ID NO:17–18, respectively), which is apparent in the SH2 region that appears at the N-terminus of Nsp1. This native sequence Nsp1 also contains a proline-serine rich domain (PS) in the middle of the protein that may function as an SH3 interaction domain. The C-terminus of this native sequence Nsp1 has no significant identity to any known mammalian proteins. This C-terminal sequence was then used to rescreen the EST database, wherein was found two additional fragments (104191)(DNA38653)(FIG. 4B) and (1651811)(DNA38654)(FIG. 4C (SEQ ID NO:14–15, respectively)). From these sequences were constructed cloning and enrichment primers, and the corresponding full length sequences were isolated for native sequence Nsp2 (SEQ ID NO:3) and native sequence Nsp3 (SEQ ID NO:5) respectively, using an in vivo cloning technique from a human placenta library in pRK5. The probes used for the cloning of the full length sequences were the following:

```
native sequence Nsp1:
Cloning: (SEQ ID NO:7)              ACTGAGGCCTGTTGAAAGTGCAGAGCTCAG
Enrichment Primer: (SEQ ID NO:8)    GCTGAAGAAGAGCTTCAG native sequence Nsp2:
Cloning: (SEQ ID NO:9)              CAATGCCGATGGCCATTGTGTTGTGTCTTTCAATTATGTCCAGGCGCA
Enrichment Primer: (SEQ ID NO:10)   ATCCCAGAATGTCCACTG native sequence Nsp3:
Cloning: (SEQ ID NO:11)             GGCCAGCATGATGGACATGGTGTGGAACCTTTCCAGCAGGTCTAGGCGTA
Enrichment Primer: (SEQ ID NO:12)   GGTGCAGCCCAGGATGTC
```

The three native sequence proteins (Nsp1, Nsp2, Nsp3 (SEQ ID NOS:1, 3, 5, respectively) share an overall identity of between 33% and 47% (FIG. 6B). Native Sequence Nsp3 (SEQ ID NO:5) has an SH2 domain and a potential SH3 interaction domain (PS region). Native sequence Nsp2 (SEQ ID NO:3) Nsp2 lacks the SH2 domain but does have a potential SH3 interaction domain. The absence of the SH2 domain in native sequence Nsp2 (SEQ ID NO:3) raises the possibility that this protein could act as a dominant negative regulator of the other two Nsps. All three proteins lack apparent kinase or phosphatase domains.

Native sequence cDNA clones Nsp1, Nsp2 and Nsp3 were sequenced in their entirety. The entire nucleotide sequence of DNA30676, DNA40575 and DNA61601 is shown in FIG. 1 (SEQ ID NO: 2), FIG. 2 (SEQ ID NO: 4) and FIG. 3 (SEQ ID NO: 6), respectively. Clones DNA30676-1223, DNA40575-1223 and DNA61601-1223 h been deposited with ATCC and are assigned ATCC deposit numbers 209567, 209565 and 209713. Moreover, clones DNA40556-1223 and DNA40554-1223 have also been deposited with the ATCC and are assigned ATCC deposit numbers 209566 and 2096564.

Example 2

Northern Blot Analysis

Expression of PRO201, PRO308 OR PRO309 mRNA in human tissues was examined by northern blot analysis. Human RNA blots were hybridized to an $^{32}$P-endlabelled DNA probe complementary to the nucleotide encoding amino acids: (a) 90–102 in DNA30676; (b) 270–284 in DNA40575 or (c) 475–491 in DNA6 Endocrine and fetal II (Clontech) were hybridized in ExpressHyb® hybridization solution (Clontech) in accordance with the manufacturer's instructions. Blots were incubated with the probes in hybridization buffer (5X SSPE; 2X Denhardt's solution; 100 mg|mL denatured sheared salmon sperm DNA; 50% formamide; 2% SDS) for 16 hours at 42° C. The blots were washed several times in 2X SSC; 0.05% SDS for 1 hour at room temperature, followed by a 30 minute wash in 0.1X SSC; 0.1% SDS at 50° C. The blots were developed after overnight exposure by phosphorimager analysis (Fuji).

Figure 9B:
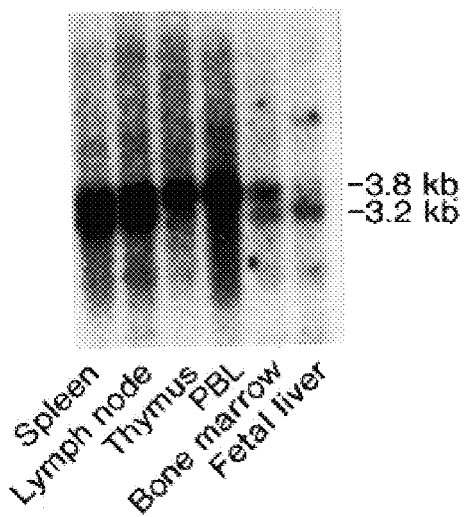
FIG. 9B shows the expression of two Nsp3 transcripts in hematopoietic tissues.

As shown in FIG. 9A, significant expression of native sequence Nsp2 (SEQ ID NO:3) was only detected in human fetal liver and may be expressed in other fetal tissues (e.g., fetal kidney). This pattern of expression suggests a role for Nsp1 in coordinating signaling pathways important for fetal development. In contrast, native sequence Nsp2 DNA (SEQ ID NO:4) and native sequence Nsp3 DNA (SEQ ID NO:6) were more widely expressed in many tissues. In hematopoietic tissues, two Nsp2 transcripts (3.8 Kb and 3.2 Kb) were detected (FIG. 9B).

Example 3

Figure 10A:
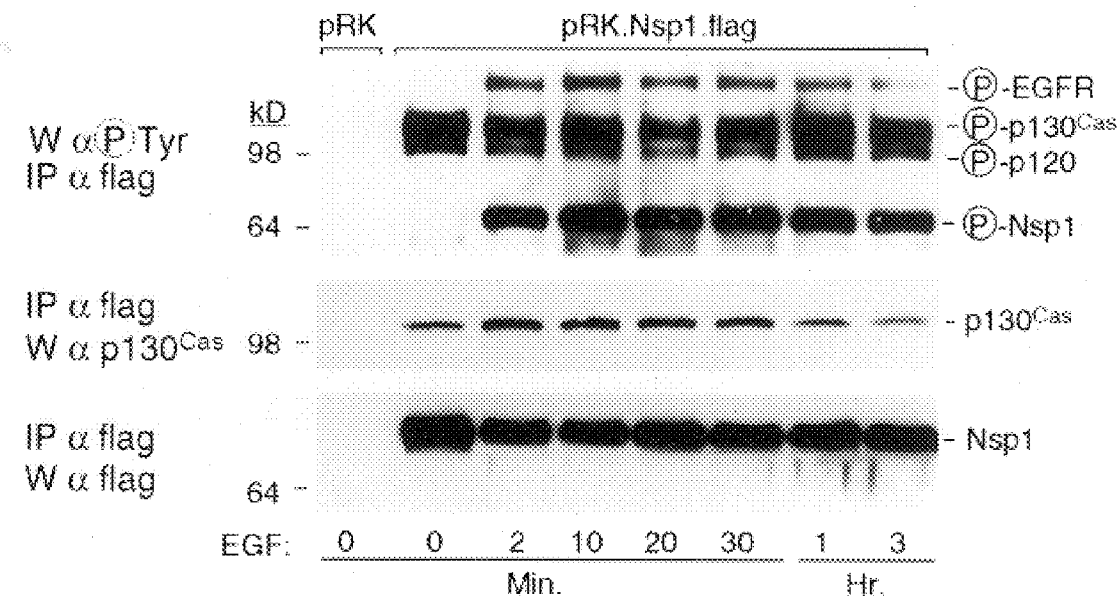
FIGS. 10A and 10C are western blots wherein anti-flag immunoprecipitates were blotted with anti-flag, anti-(P)Tyr or anti-Cas antibodies as indicated.
Figure 10B:
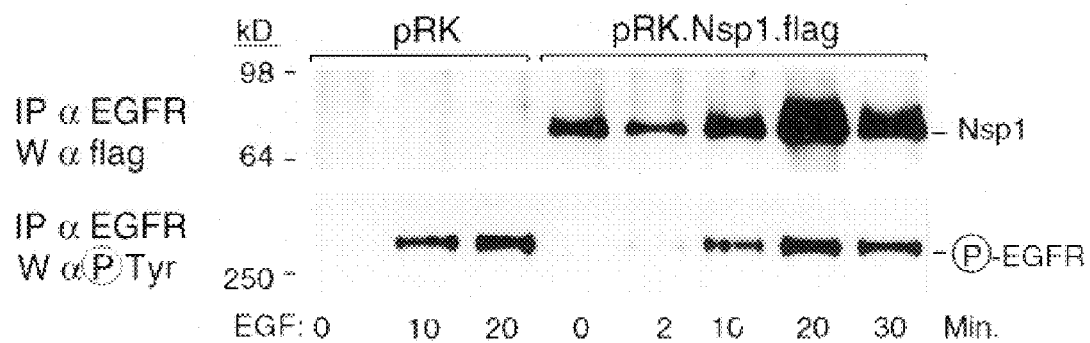
In FIG. 10B, anti-EGF receptor (CalBiochem) immunoprecipitates were blotted with anti-flag or anti-(P)Tyr antibodies as indicated.
Figure 10C:
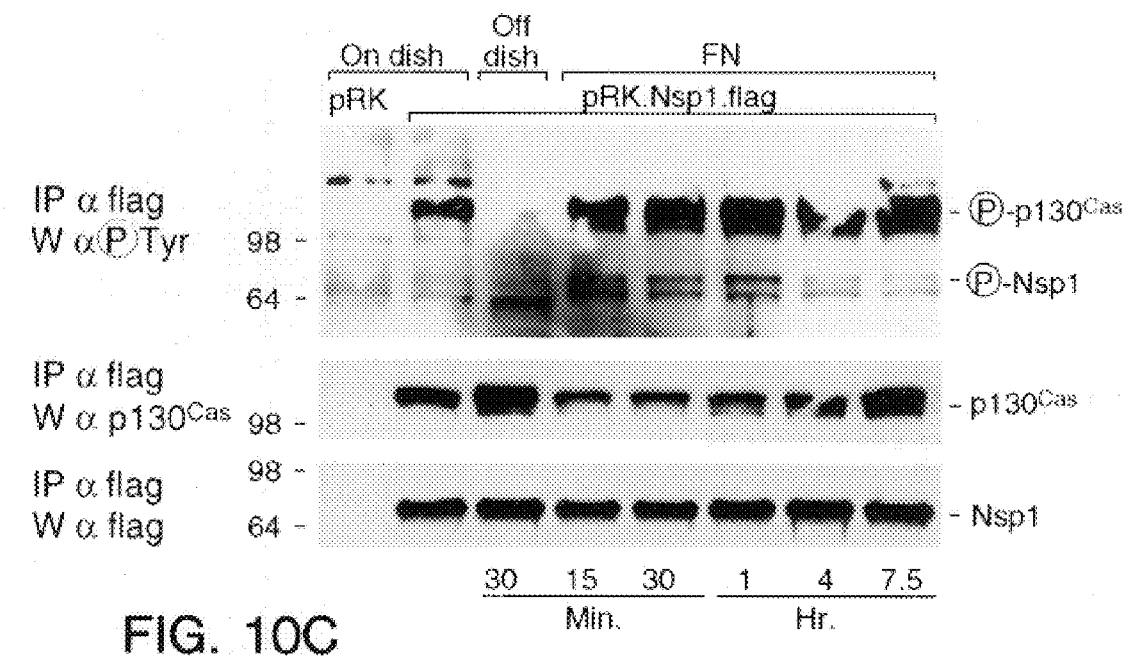

EGF, Insulin and Fibronectin induced Nsp1 Phosohorylation and complex formation with p130$^{Cas}$ As native sequence Nsp1 (SEQ ID NO:1) has three potentially phosphorylatable tyrosines, a study was undertaken to determine whether Nsp1 could be phosphorylated in response to a variety of extracellular stimuli. Treatment with EGF induced a rapid tyrosine phosphorylation of native sequence Nsp1 (SEQ ID NO:1) which occurred in 2 minutes or less (FIG. 10A). Native sequence Nsp1 (SEQ ID NO:1) is also phosphorylated in response to insulin, IGF-1 and heregulin (not shown). In contrast, fibronectin (FN) stimulated only weak Nsp1 phosphorylation (FIG. 10C).

In order to trace the pathway(s) impacted by Nsp1, Applicants have identified proteins associated with Nsp1 in vivo by way of co-immunoprecipitation experiments. Treatment with EGF lead to an association between Nsp1 and a tyrosine phosphorylated protein with a molecular mass of approximately 170 kD. This protein is rapidly tyrosine phosphorylated in response to EGF and can be detected with a mAB directed against the EGF receptor. Further, Nsp1 can be detected by western blotting following immunoprecipitation of the EGF receptors (FIG. 10B). There is residual Nsp1/EGF receptor interaction prior to EGF treatment, but the extent of the interaction significantly increases following exposure to EGF.

The coimmunoprecipitation experiments also revealed that Nsp1 interacts with a 130 kD protein (p130). In serum starved cells p130 was phosphorylated to a moderate level (FIG. 10A), whereas loss of cell attachment lead to a complete p130 dephosphorylation (FIG. 10C). By western blotting analysis this p130 was found to the adaptor protein p130$^{Cas}$. In FIG. 10A, anti-(P)Tyr antibody detected two bands at approximately 130 kD, while anti-Cas antibody recognizes only the bottom band. We have not yet identified the upper band. Cas was originally found as a hyperphosphorylated protein following induced expression of viral Crk (v-Crk) [Sakai et al., *EMBO J.* 13: 3748–56 (1994)] and is phosphorylated in response to integrin interaction with extracellular matrix as well as a number of other stimuli. Chen et al., *J. Biol. Chem.* 272: 27401–10 (1997); Casamassima & Rozengurt, *J Biol. Chem.* 272: 9363–70 (1997); Nojima et al., *J. Biol. Chem.* 270: 15398–402 (1995). Cas directly interacts with focal adhesion kinase (FAK)[Polte & Hanks, *Proc. Nat. Acad. Sci. USA*.92: 10678–82 (1995)] and appears to be a critical component by which extracellular events influence cell motility morphology and survival. Daniel & Reynolds, *Mol. & Cell. Biol.* 15: 4819–24 (1995); Mo & Reynolds, *Cancer Res.* 56: 2633–40 (1996); Nakamoto et al., *Mol. Cell. Biol.* 17:3884–97(1997).

The phosphorylation status of Nsp1 and Cas and the relative amount of Cas associated with Nsp1 is dependent on the signaling through either the EGF or integrin receptors. EGF increases Nsp1 phosphorylation but dephosphorylation of both total (data not shown) and Nsp1 associated Cas (FIG. 10A). There is also an increase in the amount of Cas associated with Nsp1 after EGF treatment (FIG. 10A). In contrast, fibronectin had only a small effect on Nsp1 phosphorylation but increased the phosphorylation of Cas that is associated with Nsp1 and at the same time lead to a transient decrease in the amount of Cas that is associated with Nsp1 (FIG. 10C). An increase in Cas phosphorylation in response to integrins has been previously reported. Nojima et al., *J. Biol. Chem.* 270: 15398–402 (1995). This decrease in the Nsp1/Cas complex reached a nadir at approximately 30 minutes and then returned toward baseline conditions at around 4 hours.

Figure 11:
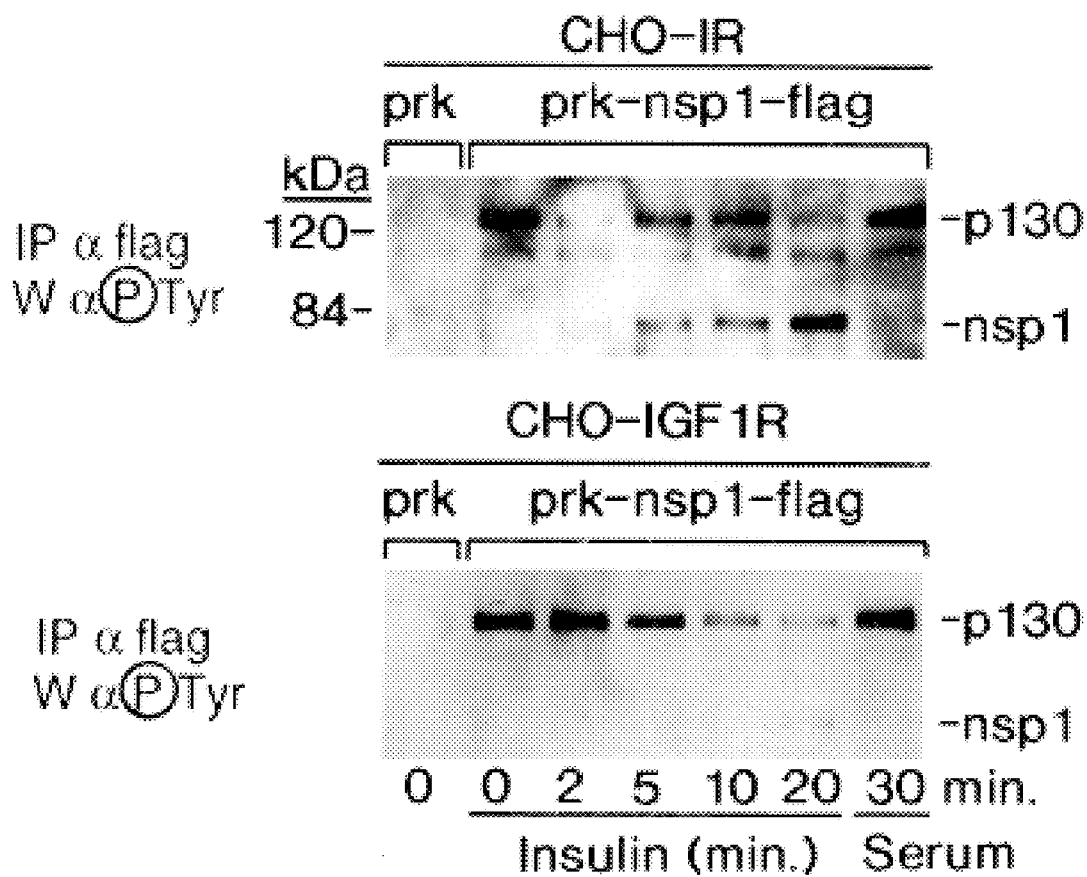
FIG. 11 is a western blot showing immunoprecipitates with anti-Flag or anti-p130$^{Cas}$ and blotting with anti-(P)Tyr Ab PY-20 or anti-p130$^{Cas}$.

In FIG. 11 it is demonstrated that insulin stimulated Nsp1 phosphorylation peaked at 2 hours, and then decreased after 14.5 hours. The same blot was reprobed with anti-FLAG antibody to show the equal loading . In FIG. 11 it is demonstrated that IGF-1 also stimulates the phosphorylation of Nsp1 although the level of phosphorylation in response to IGF-1 is less than that seen in response to insulin.

Figure 12A:
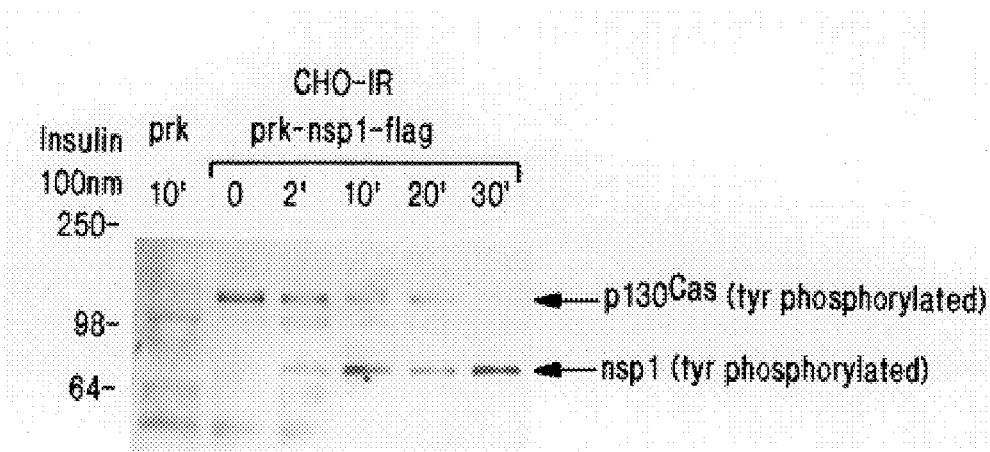
FIG. 12A is a western blot showing reduced phosphorylation of Nsp1 upon treatment with insulin.
Figure 12B:
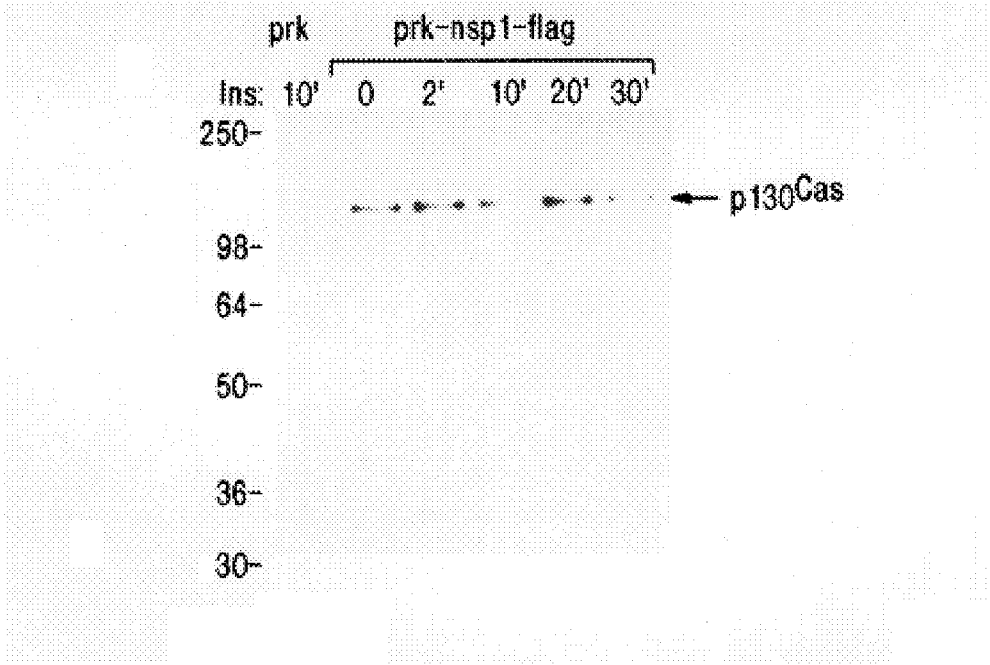
FIG. 12B is western blot created by stripping the blot in FIG. 12A which was reprobed with anti-p130$^{Cas}$ to confirm that the 130 kD protein was in fact p130$^{Cas}$.
Figure 13:
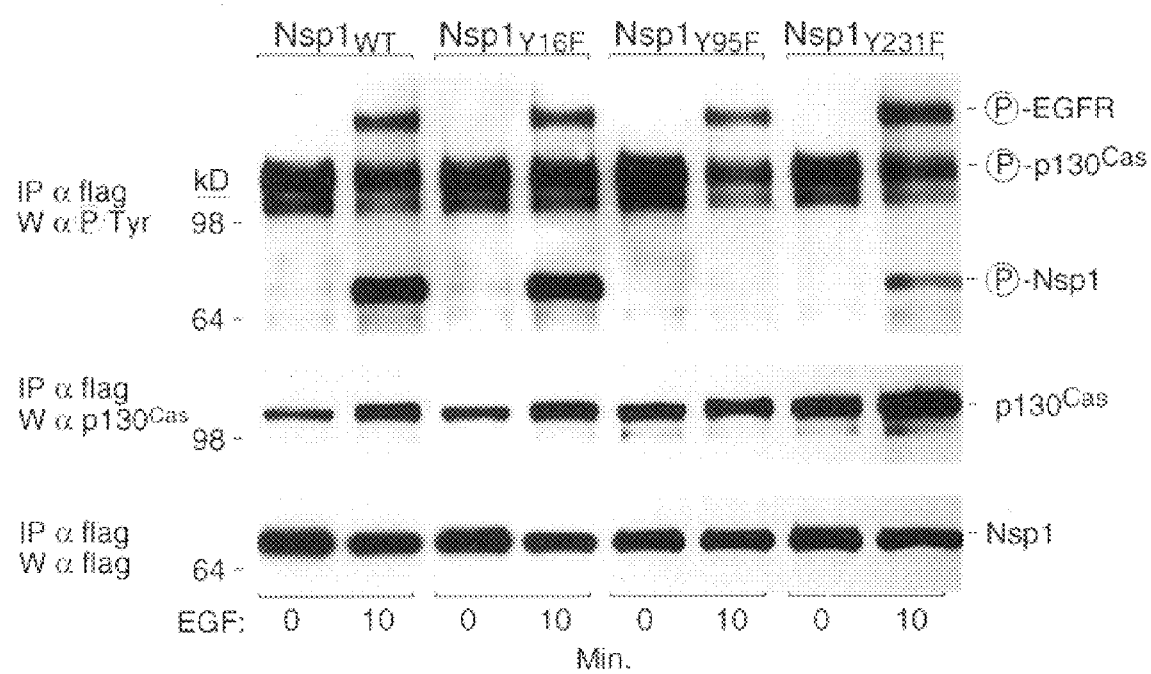
FIG. 13 is a western blot of various Nsp1 mutants which have been transfected into COS cells and treated with EGF, and the cell lysates immunoprecipitated with anti-flag Ab and Western blotted with either anti-(P)Tyr, anti-p130$^{Cas}$ or the anti-flag Ab.

IGF-1 results:

In the absence of insulin (FIG. 13) or EGF (not shown) Nsp1 is associated with Cas. The phosphorylaion of Cas was observed to decrease after insulin treatment. This is indicated both in FIG. 12 and FIG. 13A. The membrane of the tested samples in FIG. 13A was stripped and reprobed with anti-p130$^{Cas}$ antibody to also demonstrate that the amount of Cas associated with Nsp1 decreases following insulin treatment.

Materials and Methods:

EGF/fibronectin:

Transfected and serum starved COS (A,B) were either treated with 25 ng/ml EGF for the times indicated or left untreated. Transfected and serum starved 293 cells were either attached to plastic (on dish), held in suspension (off dish) or replated onto 10 mg/ml FN-coated dishes for the times indicated FIG. 10C(C). In FIGS. 10A and 10C anti-flag immunoprecipitates were blotted with anti-flag, anti-(P) Tyr or anti-Cas antibodies as indicated. In FIG. 10B, anti-EGF receptor (CalBiochem) immunoprecipitates were blotted with anti-flag or anti-(P)Tyr antibodies as indicated. Transfected cells were lysed in coimmunoprecipitation assay (CoIPA) buffer (20 mM Tris, pH 7.5, 100 mM NaCl, 1% Triton X-100, 2 mM EDTA, 10 mM sodium pyrophosphate, 10 mM sodium fluoride, 2 mM orthovanadate) containing freshly added protease inhibitors (lmM AEBSF, 10 mM leupeptin, 2 mg/ml aprotinin, 1 mM pepstatin). Anti-flag (Kodak, IBI immunoprecipitates and the associated proteins were visualized by anti-(P)Tyr antibody PY20 (Transduction Lab). The same blots were striped and reblotted with anti-p130$^{Cas}$ (Transduction Lab) or anti-flag antibody and detected with the ECL system (Pierce). The Flap epitope (DYKDDDDK) (SEQ ID NO:19) was added in frame to the N-terminus of the Nsp1 cDNA construct using in vitro mutagenesis to reate pRK.Nsp1.FLAG.

Insulin:

The FLAG epitope (DYKDDDDK) (SEQ ID NO:19) was inserted into the N-terminus of the Nsp1 cDNA construct using a standard in vitro mutagenesis to create pRK.Nsp-.FLAG. CHO cells overexpressing insulin receptor (CHO-IR) were cultured in F12-DMEM containing 10% serum, 2 mM L-glutamine, 100 units/ml penicillin, and 100 $\mu$g/ml streptomycin. Liposome-mediated transfection methods using DOSPER (Boehringer Mannheim) or superfect (Qiagen) were carried out on CHO cells in accordance with the manufacturers instructions. CHO-JR cells were transiently transfected with either the empty vector pRK or with pRK.Nsp1.FLAG and serum starved for 16 hours. Cells were treated with or without 100 nM insulin for different times and then lysed on ice for one hour in 1 ml of immunoprecipitation assay (IPA) buffer (10 mM Tris, pH7.5, 150 mM CaCl, 0.1% SDS, 1% Triton X-100, 1% deoxycholate, 5 mM EGTA, 10 mM sodium pyrophosphate, 10 mM sodium fluoride, 2 mM orthovanadate) containing fresh added protease inhibitors (1 mM AEBSF, 10 $\mu$M leupeptin, 2 $\mu$g/ml aprotinin, 1 $\mu$M pepstatin). Samples were immunoprecipitated with an anti-FLAG affinity gel (IBI, Kodak). Following SDS-polyacrylamide gel electrophoresis, proteins were transferred onto nitrocellulose membrane (Novex), western blotted with the anti-phosphotyrosine antibody PY-20 (Transduction Lab) or anti-FLAG antibodies and detected with the ECL system (Pierce).

IGF-1 pRK or pRK.Nsp1.FLAG transfected with CHO-IR or CHO-IGF1R (IGF-1 receptor) cells were serum starved, treated with 100 nM insulin or 100 ng/ml IGF-1 and lysed in coimmunoprecipitation assay (CoIPA) buffer (20 mM Tris, pH 7.5, 100 mM NaCI, 1% Triton X-100, 2 mM EDTA, 10 mM sodium pyrophosphate, 10 mM sodium fluoride, 2 mM orthovanadate) containing protease inhibitors. Samples were immunoprecipitated with anti-FLAG or anti-p130$^{Cas}$ and Western blotted with the anti-phosphotyrosine antibody PY-20 or anti-p130$^{Cas}$ (Santa Cruz Biotechnology).

Example 4

Mapping of Phosphorylated Tyrosine Residues in Nsp1

In order to map the phosphorylated residues in native sequence Nsp1 (SEQ ID NO:1), Applicants have independently changed each of the three tyrosine in Nsp1 (SEQ ID NO:1) to phenylalanine. Transfected cells were then stimulated with EGF and the Nsp1 (SEQ ID NO:1) immunoprecipitated. In all three cases the non-phosphorylated Nsp1 (SEQ ID NO:1) immunoprecipitated from non-stimulated cells was associated with both Cas and the EGF receptor. These results demonstrate that the amino acid changes were not grossly deleterious to the overall protein structure. While mutant Nsp1$_{Y61F}$ was phosphorylated normally in response to EGF, phosphorylation of Nsp1$_{Y95F}$ was not detected and Nsp1$_{Y231F}$ was weakly phosphorylated. This data suggests that there is first a phosphorylation of Y95 followed by the phosphorylation of Y231. Y16 may or may not be phosphorylated, but is not required for phosphorylation of either Y95 or Y231. Further, as the amount of EGF receptor coimmunoprecipitated with native sequence Nsp1 (SEQ ID NO:1) is increased by receptor phosphorylation but largely independent of Nsp1 phosphorylation, it would appear that Nsp1 association with Cas is independent of both Nsp1 and Cas phosphorylation status (FIG. 10), this interaction may be mediated through the SH3 domain of Cas and SH3 interaction domain of Nsp1.

Materials and Methods:

All three tyrosine residues in Nsp1 were changed to phenylalanine using a standard in vitro mutagenesis technique. Mutants (Y16F, Y95F and Y231F) and wild type native sequence Nsp1 (SEQ ID NO:1) were transfected into COS cells and treated with 25 ng/ml of EGF for 10 min. or left untreated. Cell lysates were immunoprecipitated with the anti-flag antibody and Western blotted with either the anti-P(Tyr) antibody, the anti-p 1 $_{30}$cr antibody or the anti-flag antibody.

Example 5

Transformation and Tumorigenicity in Nude Mice

Intro:

Since Cas has been implicated in c-src mediated events [Sakai et al., *EMBO J.* 13: 3748–56 (1994); Sakai et al., *Oncogene* 14: 1419–26 (1997)], Applicants examined the effect of native sequence Nsp1 (SEQ ID NO:1) in an NIH3T3 transformation assay. The NIH3T3 is a cell line which normally grow in monolayer even when the cells are overconfluent. They may be used to determine whether or not a candidate gene has the potential for oncogenicity when the candidate is transfected via retroviral mediated infection in vector MSCV. The transfected cells are allowed to generate into foci, picked and cultured to 10 million cells and injected into nude mice. It the transfected gene is oncogenic, it will grow on uninhibited by the deficient immune system of the nude mouse and form a tumor. See Winograd et al., In Vivo 1 (1): 1–13 (1987).

Figure 14A:
FIG. 14A is a micrograph of an ultrathin section of retroviral-infected vector MSCV NIH3T3 cells, while FIG. 14B show Nsp1 transfected NIH3T3 cells.

Discussion and Results:

More than one hundred foci of morphologically transformed cells were observed on one 100 mm plate of NIH3T3 cells following transfection with a retrovirus expressing native sequence Nsp1 (SEQ ID NO:1) and G418 selection, but none appeared in control (neo) vector. The transformed cells (FIG. 14B) were more rounded and compacted in comparison to the normal elongated fibroblast shape of the control transfected NIH3T3 cells (FIG. 14A). To investigate whether the transformned native sequence Nsp1 (SEQ ID NO:1) expressing cells were also tumorigenic, three independent foci were picked and expanded to generate NIH3T3-MSCV.Nsp1-.sub1, -.sub2 and -.sub3. Controls consisted of cell lines expressing neo only (NIH3T3-neo) and a pool of transfected cells that expressed lower levels of native sequence Nsp1 (SEQ ID NO:1) but was not transformed (NIH3T3-Nsp1.non-trans). The native sequence Nsp1 (SEQ ID NO:1) expressing, non-transformed cells were derived by infecting NIH3T3 cells with the Nsp1 expressing retroviral vector. These bulk cultures were selected for neomycin resistance, but were not allowed to proceed through the postconfluent growth that selects for foci formation.

Figure 14B:
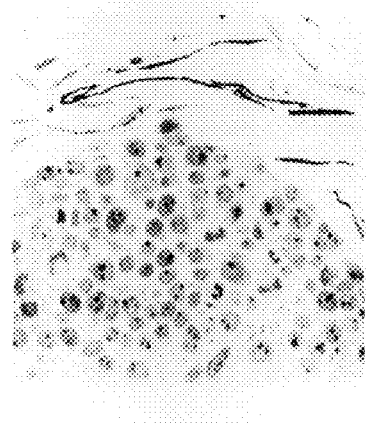
FIG. 14C is a micrograph of an ultrathin section of four week tumors which were fixed, blocked and sections stained with hematoxylin and eosin.
Figure 14C:
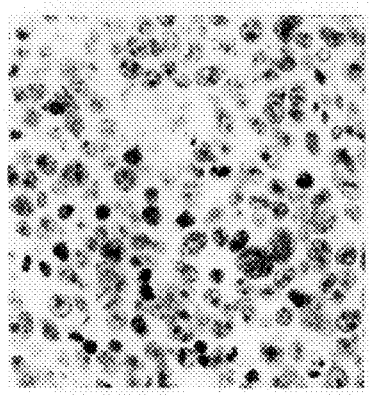

Each cell line was injected into five mice. No tumor growth was observed in any mice injected with neo control cells or NIH3T3-Nsp1.non-trans. cells. All five mice in each group injected with NIH3T3-MSCV.Nsp1-.sub1, -.sub2, -.sub3 grew obvious tumors within three weeks. Histological analysis indicated that the tumors consisted of large, irregular, moderately anaplastic epithelioid cells with a high mitotic index (FIG. 14C). There was no evidence of metastasis.

The tumors which formed were well circumscribed, locally expansile masses composed primarily of larger, irregular, moderately anaplastic epitheloid cells with a high mitotic index, interspersed, peripherally by small areas of spindle-cell proliferation. (FIG. 14C).

Materials and Methods:

pRK.Nsp1.FLAG plasmid was digested with EcoRI and Sal I. The native sequence Nsp1 (SEQ ID NO:1) cDNA fragment including the FLAG epitope was purified and subcloned into the EcoRI and Xho I sites of the retroviral vector MSCVneo resulting in MSCVneo.Nsp1.FLAG. Mouse embryonic fibroblast cells (ATCC) and retroviral producer BOSC 23 cells were maintained in DMEM with 10% fetal bovine serum, 2 mM L-glutamine, 100 units/ml penicillin, and 100 $\mu$g/ml streptomycin.

The retroviral vectors MSCVneo and MSCVneo.Nsp1 FLAG were transfected into BOSC 23 cells using calcium phosphate-mediated transfection. The 72-hour supernatant was used to infect NIH3T3 cells plated on a 6-well plate. Infected cells were selected in 400 $\mu$g/ml G418 (Gibco) and pooled to generate NIH3T3-MSCV and -MSCV.Nsp1 cell lines. NIH3T3-MSCV and -MSCV.Nsp1 cells were grown until confluent for 4 days with a medium change once, split at a one to five ratio and grown until confluent for another 4 days. More than one hundred foci of morphologically transformed cells were observed on one 100 mm plate of NIH3T3 cells following infection, but none in the control (neo) vector. Foci were subjected to ultrathin section followed by Tuluidine blue staining. FIG. 14A shows ultrathin sections of either control cells (FIG. 14A), while FIG. 14B shows native sequence Nsp1 (SEQ ID NO:1) transformed foci.

Three transformed foci of NIH3T3-MSCV.Nsp1 were picked and expanded to generate sublines NIH3T3-MSCV.Nsp1-sc1, -sc2 and -sc3. $10^7$ vector transfected control cells, untransformed NIH3T3.MSCV.Nsp1 and three sublines were injected subcutaneously into the back of each nude mouse. Five mice were injected for each cell line.

Figure 15:
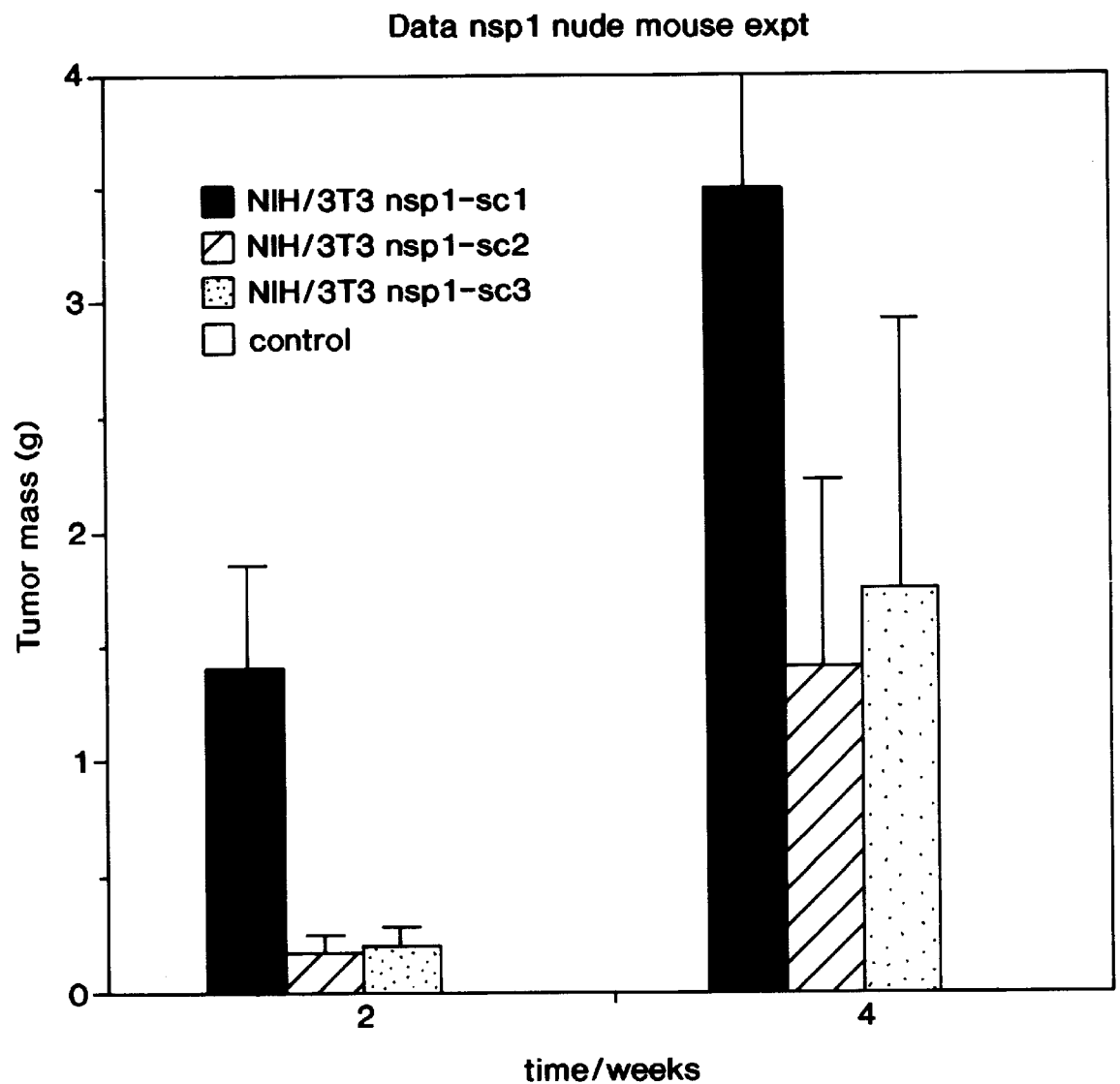
FIG. 15 is a bar graph of tumor size comparing vector control transfection and Nsp1.sc1, .sc2 and .sc3 cells.

Tumor mass was measured at two weeks and four weeks. The resultant tumors (four weeks post injection) were fixed, blocked and sections stained with hematoxylin and eosin. (FIG. 14C). No tumor growth was observed in any mouse injected with vector transfected control cells or untransformed NIH3T3-MSCV.Nsp1 cells. Every mouse injected with NIH3T3-MSCV.Nsp1-.sc1, -.sc2 or -.sc3 grew tumors. (FIG. 15).

Example 6

Apoptosis Resistance

Figure 16:
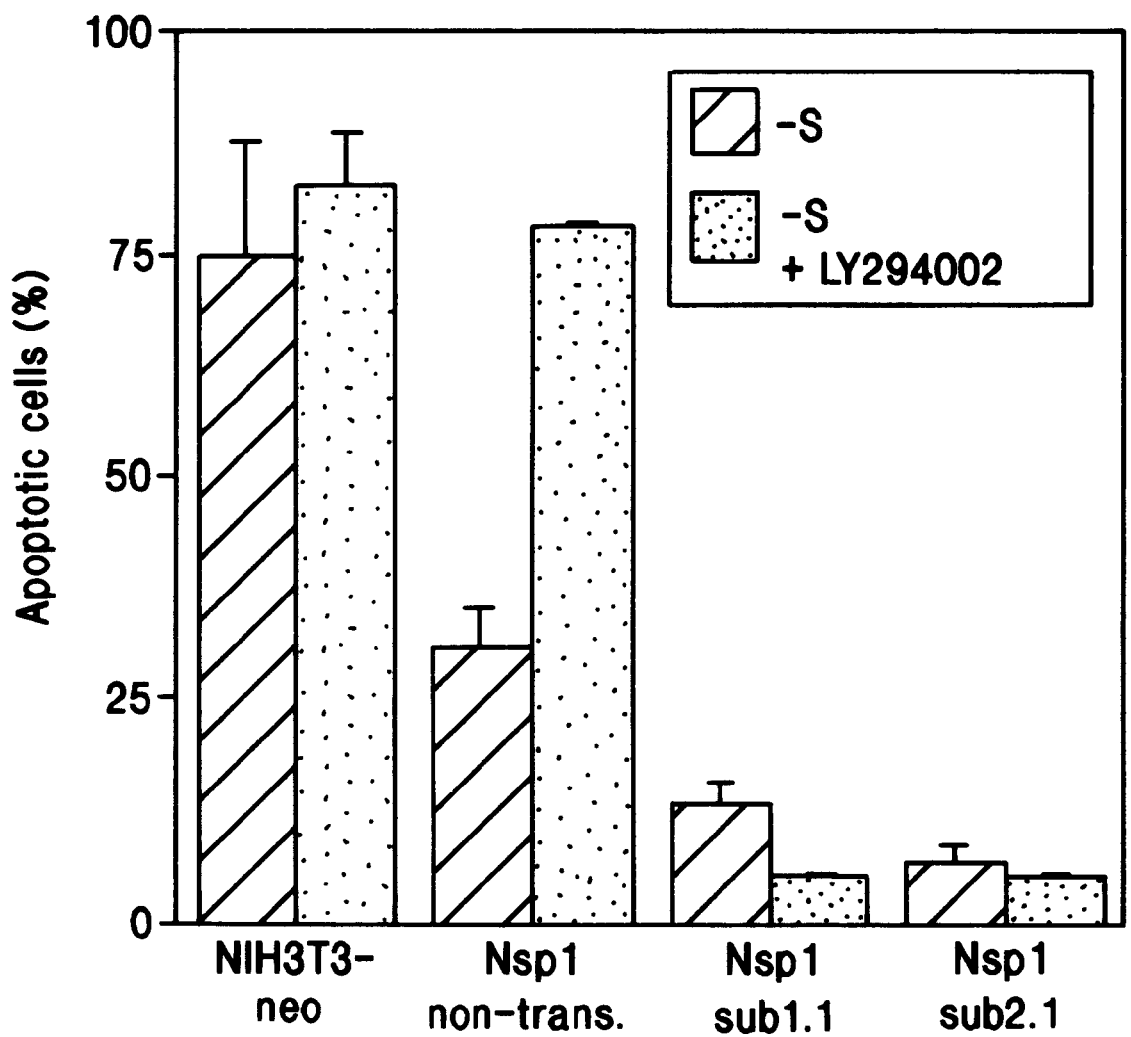
FIG. 16 is a bar graph of showing resistance to apoptosis of gronvth factor deprived NIH3T3 of transformed subclones Nsp.sub1.1, Nsp.sub.2.1, nontransformed cell culture (NIH3T3-Nsp1.non-trans) and the control cells NIH3T3-neo.
Figure 17:
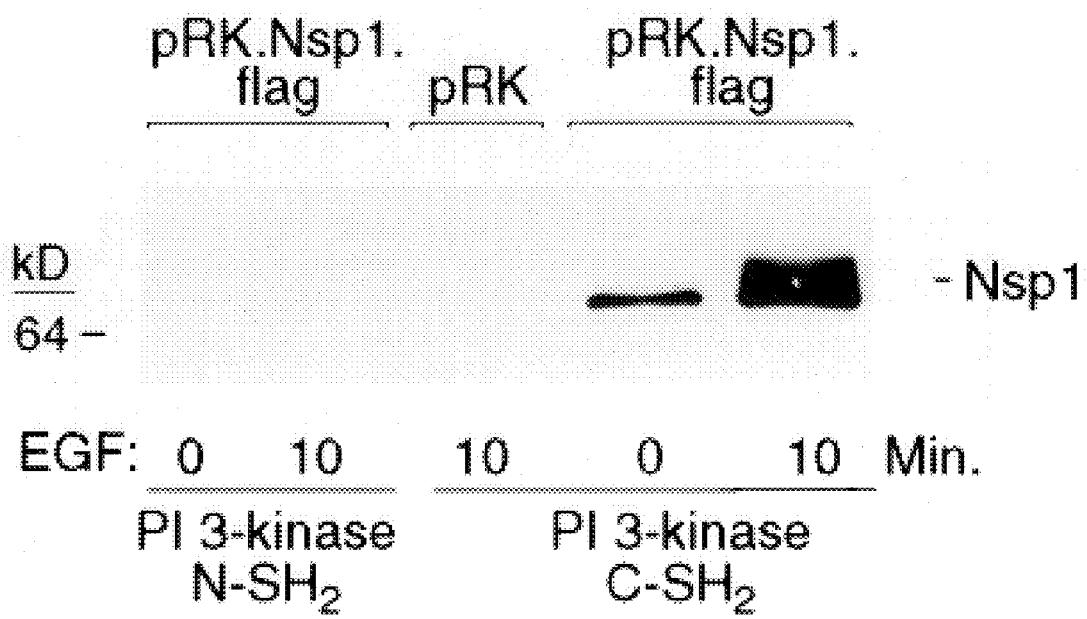
FIG. 17 is a western blot of COS cells transfected with pRK or Nsp 1, treated with EGF or no treatment, which were lysed in CoIP buffer and incubated with PI3-kinase N-terminal or C-terminal SH2 domain-GST beads (UBI). The precipitated Nsp1 was detected with anti-flag antibody.

Since the previous examples indicated that Nsp1 expression leads to NIH3T3 transformation and tumor formation, Applicants have investigated whether native sequence Nsp1 (SEQ ID NO:1) expression protects cells from apoptosis induced by removal of growth factors. Subcloned cell lines were derived from the morphologically transformed cells NIH3T3-MSCV.Nsp1-.sub1 and -.sub2 (designated Nsp1.-sub1.1 and Nsp1.sub2.1). These transformed clonal lines, the non-transformed cell culture (NIH3T3-Nsp1.non-trans.) and the control cells NIH3T3-neo were serum starved for 48 hours in the presence or absence of the PI 3-kinase inhibitor LY294002 and subjected to ANNEXIN V (Clontech) apoptosis assay (FIG. 16). Although the NIH3T3-Nsp1.non-trans. cells were morphologically normal and did not form tumors in nude mice they were more resistant to apoptosis induced by growth factor withdrawal than were the control NIH3T3-neo cells. This small but significant increase in resistance to apoptosis was abolished by the P13 kinase inhibitor LY294002. In the vector control cells which do not express native sequence Nsp1 (SEQ ID NO:1), LY294002 did not by itself induce further apoptosis. In the Nsp1 transformed sublines, there was an almost complete protection from serum starvation induced apoptosis, but this effect was not sensitive to the treatment with the PI 3-kinase inhibitor. This dependent on PI 3-kinase at lower levels of Nsp1 would place PI 3-kinase downstream of native sequence Nsp1 (SEQ ID NO:1). In contrast the observation that the growth factor independence at high Nsp1 levels is not inhibitable by LY294002 suggests that Nsp1 impacts an additional pathway that functions independently of PI 3-kinase. That PI 3-kinase is both necessary and sufficient for growth factor mediated resistance to apoptosis had been previously reported. Kulik et al., *Mol. Cell Biol.* 17: 1595–606 (1997); Parrizas et al., *J. Biol. Chem.* 272: 154–61 (1997); Vemuri et al., Development 122: 2529–37 (1996).

Material and Methods:

Control cells (NIH3T3-neo), non-transformed Nsp1 expressing cells (NIH3T3-Nsp1.non-trans.) and the transformed sublines (Nsp1.sub.1.1 and Nsp1.sub2.1) were serum starved in the presence of absence of 10 $\mu$g/ml LY294002 for 48 hours. The percent of apoptotic cells were assayed using ANNEXIN V-FITC (Clontech) on FACS according to the manufacturers directions. Each cell line was assayed in triplicate and the means and standard deviations are shown. In transformed sublines, native sequence Nsp1 (SEQ ID NO:1) protected cells from serum starvation induced apoptosis.

Example 7

PI 3-Kinase Interaction

In order to determine whether Nsp1 does interact with PI 3-kinase, a GST fusion protein containing the PI 3-kinase N-terminal or C-terminal SH2 domains were incubated with EGF treated or untreated COS cell lysate transiently expressing native sequence Nsp1 (SEQ ID NO:1) or controls (FIG. 20). The C-terminal SH2 domain GST fusion protein does interact with native sequence Nsp1 (SEQ ID NO:1). This interaction appears to be at least partially dependent on the phosphorylation status of native sequence Nsp1 (SEQ ID NO:1) as there is an increase in the amount of Nsp1 that interacts with P13 kinase following EGF stimulation. The N-terminal SH2 domain of P13 kinase does not measureably interact with native sequence Nsp1 (SEQ ID NO:1).

Material and Methods:

COS cells transfected with pRK or with native sequence Nsp1 (SEQ ID NO:1) were treated with 25 ng/ml EGF or left untreated. Cells were lysed in CoIP buffer (supra) and incubated with PI 3-kinase N-terminal or C-terminal SH2 domain-GST beads (UBI). The precipitated Nsp1 was detected with anti-flag antibody.

Example 8

Expression of PRO201, PRO308 or PRO309 in *E. coli*

This example illustrates preparation of an unglycosylated form of PRO201, PRO308 or PRO309 by recombinant expression in *E. coli*.

The DNA sequence encoding PRO201, PRO308 or PRO309 (SEQ ID NO:2, SEQ ID NO: 4, SEQ ID NO: 6) is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli;* see Bolivar et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO201, PRO308 or PRO309 coding region, lambda transcriptional terminator, and an argu gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO201, PRO308 or PRO309 protein can then be purified using a metal chelating column under conditions that allow tight binding of the protein.

Example 9

Expression of PRO201, PRO308 orPRO309 in mammalian cells

This example illustrates preparation of a glycosylated form of PRO201, PRO308 or PRO309 by recombinant expression in mammalian cells.

The vector, pRK5 (see EP 307,247, published Mar. 15, 1989), is employed as the expression vector. optionally, the PRO201, PRO308 or PRO309 DNA is ligated into pRK5 with selected restriction enzymes to allow insertion of the PRO201, PRO308 or PRO309 DNA using ligation methods such as described in Sambrook et al., supra. The resulting vector is called pRK5-PRO201, pRK5-PRO308 or pRK5-PRO309.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO201, pRK5-PRO308 or pRK5-PRO309 DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$.

To this mixture is added, dropwise, 500 μl of 50 mM HEPES (pH 7.35), 280 mM NaCl, 1.5 mM $NaPO_4$, and a precipitate is allowed to form for 10 minutes a 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO201, PRO308 or PRO309 polypeptide. The cultures containing transfected cells may undergo further incubation (in serum free medium) and the medium is tested in selected bioassays.

In an alternative technique, PRO201, PRO308 or PRO309 may be introduced into 293 cells transiently using the dextran sulfate method described by Somparyrac et al., *Proc. Natl. Acad. Sci.,* 12:7575 (1981). 293 cells are grown to maximal density in a spinner flask and 700 ug pRK5-PRO201, pRK5-PRO308 or pRK5-PRO309 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 :g/ml bovine insulin and 0.1 :g/ml bovine transferrin. After about four days, the conditioned media is centrifuged and filtered to remove cells and debris. The sample containing expressed PRO201, PRO308 or PRO309 can then be concentrated and purified by any selected method, such as dialysis and/or column chromatography.

In another embodiment, PRO201, PRO308 or PRO309 can be expressed in CHO cells. The pRK5-PRO201, PRO308 or PRO309 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO201, PRO308 or PRO309 polypeptide, the culture medium may be replaced with serum free medium. Preferably, the cultures are incubated for about 6 days, and then the conditioned medium is harvested. The medium containing the expressed PRO201, PRO308 or PRO309 can then be concentrated and purified by any selected method.

Epitope-tagged PRO201, PRO308 or PRO309 may also be expressed in host CHO cells. The PRO201, PRO308 or PRO309 may be subcloned out of the pRK5 vector. The subclone insert can undergo PCR to fuse in frame with a selected epitope tag such as a poly-his tag into a Baculovirus expression vector. The poly-his tagged PRO201, PRO308 or PRO309 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO201, PRO308 or PRO309 can then be concentrated and purified by any selected method, such as by $Ni^{2+}$-chelate affinity chromatography.

Example 10

Expression of PRO201, PRO308 or PRO309 in yeast.

The following method describes recombinant expression of PRO201, PRO308 or PRO309 in yeast.

First, yeast expression vectors are constructed for intracellular production or secretion of PRO201, PRO308 or PRO309 from the ADH2/GAPDH promoter. DNA encoding PRO201, PRO308 or PRO309, a selected signal peptide and the promoter is inserted into suitable restriction enzyme sites in the selected plasmid to direct intracellular expression of PRO201, PRO308 or PRO309. For secretion, DNA encoding PRO201, PRO308 or PRO309 can be cloned into the selected plasmid, together with DNA encoding the ADH2/GAPDH promoter, the yeast alpha-factor secretory signal/leader sequence, and linker sequences (if needed) for expression of PRO201, PRO308 or PRO309.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO201, PRO308 or PRO309 can subsequently be isolated and purified by removing the yeast cells from the fermentation medium by centriftigation and then concentrating the medium using selected cartridge filters. The concentrate containing PRO201, PRO308 or PRO309 may further be purified using selected column chromatography resins.

Example 11

Expression of PRO201, PRO308 or PRO309 in Baculovirus-Infected Insect Cells

The following method describes recombinant expression of PRO201, PRO308 or PRO309 in Baculovirus-infected insect cells.

The PRO201, PRO308 or PRO309 is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the PRO201, PRO308 or PRO309 or the desired portion of the PRO201, PRO308 or PRO309 (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoplera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged PRO201, PRO308 or PRO309 can then be purified, for example, by $Ni^{2+}$-chelate affinity chromatography as follows. Extracts are prepared from recombinant virus-infected Sf9 cells as described by Rupert et al., *Nature,* 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP40; 0.4 M KCl), and sonicated twi 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 Fm filter. A $Ni^{2+}$-agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged PRO201, PRO308 or PRO309 are pooled and dialyzed against loading buffer.

Alternatively, purification of the IgG tagged (or Fc tagged) PRO201, PRO308 or PRO309 can be performed using known chromatography techniques, including for instance, Protein A or protein G column chromatography.

Example 12

Preparation of Antibodies that Bind PRO201, PRO308 or PRO309

This example illustrates preparation of monoclonal antibodies which can specifically bind PRO201, PRO308 or PRO309.

Techniques for producing the monoclonal antibodies are known in the art and are described, for instance, in Goding, supra. Immunogens that may be employed include purified PRO201, PRO308 or PRO309, fusion proteins containing PRO201, PRO308 or PRO309, and cells expressing recombinant PRO201, PRO308 or PRO309 on the cell surface. Selection of the immunogen can be made by the skilled artisan without undue experimentation.

Mice, such as Balb/c, are immunized with the PRO201, PRO308 or PRO309 immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mt.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect PRO201, PRO308 or PRO309 antibodies.

After a suitable antibody titer has been detected, the animals "positive" for antibodies can be injected with a final intravenous injection of PRO201, PRO308 or PRO309. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO201, PRO308 or PRO309. Determination of "positive" hybridoma cells secreting the desired monoclonal antibodies against PRO201, PRO308 or PRO309 is within the skill in the art.

The positive hybridoma cells can be injected intraperitoneally into syngeneic Balb/c mice to produce ascites containing the anti-PRO201, anti-PRO308 or anti-PRO309 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Deposit of Material

The following materials have been deposited with the American Type Culture Collection, 12301 Parklawn Drive, Rockville, Md., USA (ATCC):

| Material | ATCC Dep. No. | Deposit Date |
|---|---|---|
| DNA30676-1223 | 209567 | 12/23/97 |
| DNA40575-1223 | 209565 | 12/23/97 |
| DNA40556-1223 | 209566 | 12/23/97 |
| DNA40554-1223 | 209564 | 12/23/97 |
| DNA61601-1223 | 209713 | 3/31/98 |

DNA40556 & DNA40554 may be combined to cover a full length coding sequence of an Nsp3 variant.

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. Isolated nucleic acid comprising DNA having at least a 95% sequence identity to (a) a DNA molecule encoding a PRO201 polypeptide comprising the sequence of amino acids 1 to 576 of FIG. 1 (SEQ ID NO: 1), or (b) the complement of the DNA molecule of (a) wherein percent identity is determined using BLAST-2 software with the default parameters.

2. Isolated nucleic acid comprising DNA having at least a 95% sequence identity to (a) a DNA molecule encoding a PRO308 polypeptide comprising the sequence of amino acids 1 to 501 of FIG. 2 (SEQ ID NO: 3), or (b) the complement of the DNA molecule of (a) wherein percent identity is determined using BLAST-2 software with the default parameters.

3. The isolated nucleic acid of claim 1 comprising DNA having at least a 95% sequence identity to (a) a DNA molecule encoding a PRO309 polypeptide comprising the sequence of amino acids 1 to 703 of FIG. 3 (SEQ ID NO: 5), or (b) the complement of the DNA molecule of (a) wherein percent identity is determined using BLAST-2 software with the default parameters.

4. The isolated nucleic acid of claim 1 comprising DNA encoding a PRO201 polypeptide having amino acid residues 1 to 576 of FIG. 1 (SEQ ID NO: 1).

5. The isolated nucleic acid of claim 1 comprising DNA encoding a PRO308 polypeptide having amino acid residues 1 to 501 of FIG. 2 (SEQ ID NO: 3).

6. The isolated nucleic acid of claim 1 comprising DNA encoding a PRO309 polypeptide having amino acid residues 1 to 703 of FIG. 3 (SEQ ID NO: 5).

7. An isolated nucleic acid comprising DNA having at least a 95% sequence identity to (a) a DNA molecule encoding the same mature polypeptide encoded by the cDNA in ATCC Deposit No. 209567 (designation: DNA30676-1223), or (b) the complement of the DNA molecule of (a) wherein percent identity is determined using BLAST-2 software with the default parameters.

8. An isolated nucleic acid comprising DNA having at least a 95% sequence identity to (a) a DNA molecule encoding the same mature polypeptide encoded by the cDNA in ATCC Deposit No. 209565 (designation: DNA40575-1223), or (b) the complement of the DNA molecule of (a) wherein percent identity is determined using BLAST-2 software with the default parameters.

9. An isolated nucleic acid comprising DNA having at least a 95% sequence identity to (a) a DNA molecule encoding the same mature polypeptide encoded by the cDNA in ATCC Deposit No. 209713, or (b) the complement of the DNA molecule of (a) wherein percent identity is determined using BLAST-2 software with the default parameters.

10. A vector comprising the nucleic acid of claim 1.

11. A vector comprising the nucleic acid of claim 2.

12. A vector comprising the nucleic acid of claim 3.

13. The vector of claim 10 operably linked to control sequences recognized by a host cell transformed with the vector.

14. The vector of claim 11 operably linked to control sequences recognized by a host cell transformed with the vector.

15. The vector of claim 12 operably linked to control sequences recognized by a host cell transformed with the vector.

16. A host cell comprising the vector of claim 13.

17. A host cell comprising the vector of claim 14.

18. A host cell comprising the vector of claim 15.

19. The host cell of claim 16 wherein said cell is mammalian.

20. The host cell of claim 19 wherein said cell is a CHO cell.

21. The host cell of claim 17 wherein said cell is prokaryotic.

22. The host cell of claim 21 wherein said cell is an *E. coli*.

23. The host cell of claim 18 wherein said cell is a yeast cell.

24. The host cell of claim 23 wherein said cell is *Saccharomyces cerevisiae*.

25. A process for producing PRO201, PRO308 or PRO309 polypeptides comprising culturing the host cell of claim 16, 17, or 18 under conditions suitable for expression of PRO201, PRO308 or PRO309, respectively, and recovering PRO201, PRO308 or PRO309, respectively, from the cell culture.

* * * * *